(12) United States Patent
Nadkarni

(10) Patent No.: US 11,129,535 B2
(45) Date of Patent: Sep. 28, 2021

(54) APPARATUS, DEVICES AND METHODS FOR OBTAINING OMNIDIRECTIONAL VIEWING BY A CATHETER

(71) Applicant: The General Hospital Corporation, Boston, MA (US)

(72) Inventor: Seemantini K. Nadkarni, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 941 days.

(21) Appl. No.: 15/428,012

(22) Filed: Feb. 8, 2017

(65) Prior Publication Data
US 2017/0143213 A1    May 25, 2017

Related U.S. Application Data

(63) Continuation of application No. 14/309,170, filed on Jun. 19, 2014.
(Continued)

(51) Int. Cl.
*A61B 5/00* (2006.01)
*A61B 5/02* (2006.01)
(Continued)

(52) U.S. Cl.
CPC .......... *A61B 5/0084* (2013.01); *A61B 5/0062* (2013.01); *A61B 5/02007* (2013.01);
(Continued)

(58) Field of Classification Search
CPC . A61B 5/0062; A61B 5/0084; A61B 5/02007; A61B 5/02028; A61B 5/6869;
(Continued)

(56) References Cited

U.S. PATENT DOCUMENTS 6,501,551 B1   12/2002  Tearney et al.
7,231,243 B2    6/2007  Tearney et al.
(Continued)

FOREIGN PATENT DOCUMENTS

JP     H043106 A    1/1992
JP     H0956662 A   8/1995
(Continued)

OTHER PUBLICATIONS

Arbab-Zadeh, et al., Quantification of Coronary Arterial Stenoses by Multidetector CT Angiography in Comparison with Conventional Angiography: Methods, Caveats, and Implications, JACC: Cardiovascular Imaging, 2011, 4(2):191-202.
(Continued)

*Primary Examiner* — Mark D Remaly
(74) *Attorney, Agent, or Firm* — Quarles & Brady LLP

(57) ABSTRACT

An apparatus for obtaining information regarding a biological structure(s) can include, for example a light guiding arrangement which can include a fiber through which an electromagnetic radiation(s) can be propagated, where the electromagnetic radiation can be provided to or from the structure. An at least partially reflective arrangement can have multiple surfaces, where the reflecting arrangement can be situated with respect to the optical arrangement such that the surfaces thereof each can receive a(s) beam of the electromagnetic radiations instantaneously, and a receiving arrangement(s) which can be configured to receive the reflected radiation from the surfaces which include speckle patterns.

19 Claims, 62 Drawing Sheets

Related U.S. Application Data

(60) Provisional application No. 61/934,454, filed on Jan. 31, 2014, provisional application No. 61/905,893, filed on Nov. 19, 2013, provisional application No. 61/836,716, filed on Jun. 19, 2013.

(51) Int. Cl.
| | | |
|---|---|---|
| G01N 21/47 | (2006.01) | |
| G01N 21/49 | (2006.01) | |
| F21V 8/00 | (2006.01) | |
| G02B 23/24 | (2006.01) | |
| G02B 23/26 | (2006.01) | |

(52) U.S. Cl.
CPC ........ *A61B 5/02028* (2013.01); *A61B 5/6853* (2013.01); *A61B 5/6869* (2013.01); *A61B 5/6876* (2013.01); *A61B 5/7203* (2013.01); *A61B 5/7275* (2013.01); *G01N 21/474* (2013.01); *G01N 21/4788* (2013.01); *G01N 21/49* (2013.01); *G02B 6/0005* (2013.01); *G02B 23/2453* (2013.01); *G02B 23/26* (2013.01); *G01N 2021/479* (2013.01); *G01N 2021/4742* (2013.01); *G01N 2201/0683* (2013.01); *G01N 2201/08* (2013.01); *G01N 2201/0826* (2013.01)

(58) Field of Classification Search
CPC ... A61B 5/6876; A61B 5/7203; A61B 5/7275; G01N 21/49; G01N 2201/08; G02B 6/0005
See application file for complete search history.

(56) References Cited

U.S. PATENT DOCUMENTS

| | | |
|---|---|---|
| 2004/0004746 A1 | 1/2004 | Riza |
| 2006/0044312 A1 | 3/2006 | Loop |
| 2006/0058622 A1 | 3/2006 | Tearney et al. |
| 2006/0079762 A1 | 4/2006 | Norris |
| 2007/0078500 A1 | 4/2007 | Ryan et al. |
| 2008/0097224 A1 | 4/2008 | Murphy et al. |
| 2008/0262359 A1 | 10/2008 | Tearney et al. |
| 2011/0301458 A1 | 12/2011 | Li et al. |
| 2011/0319712 A1 | 12/2011 | Kuroda |

FOREIGN PATENT DOCUMENTS

| | | |
|---|---|---|
| JP | H0815535 A | 1/1996 |
| JP | 2012504019 A | 2/2012 |
| JP | 2012052882 A | 3/2012 |
| JP | 2014514092 A | 6/2014 |
| WO | 1992019930 A1 | 11/1992 |
| WO | 9744089 A1 | 11/1997 |
| WO | 2006024015 A1 | 3/2006 |
| WO | 2009036453 A1 | 3/2009 |
| WO | 2009137701 A2 | 11/2009 |

OTHER PUBLICATIONS

Arbustini, et al., Coronary Atherosclerotic Plaques With and Without Thrombus in Ischemic Heart Syndromes: A Morphologic, Immunohistochemical, and Bochemical Study, The American Journal of Cardiology, 1991, 68(7):36B-50B.
Arroyo, et al., Mechanisms of Plaque Rupture: Mechanical and Biologic Interactions, Cardiovascular Research, 1999, 41:369-375.
Baldewsing, et al., Local Elasticity Imaging of Vulnerable Atherosclerotic Coronary Plaques, Adv. Cardiol., 2007, 44:35-61.
Bauriedel, et al., Role of Smooth Muscle Cell Death in Advanced Coronary Primary Lesions: Implications for Plaque Instability, Cardiovascular Research, 1999, 41:480-488.
Boas, et al., Laser Speckle Contrast Imaging in Biomedical Optics, Journal of Biomedical Optics, 2010, 15:011109.
Bonnema, et al., A Concentric Three Element Radial Scanning Optical Coherence Tomography Endoscope, J. of Biophotonics, 2009, 2:353-356.
Brezinski, et al., Optical Coherence Tomography for Optical Biopsy. Properties and Demonstration of Vascular Pathology, Circulation, 1996, 93:1206-1213.
Casscells, et al., Thermal Detection of Cellular Infiltrates in Living Atherosclerotic Plaques: Possible Implications for Plaque Rupture and Thrombosis, Lancet, 1996, 347(9013):1447-1451.
Chan, et al., OCT-based Arterial Elastography: Robust Estimation Exploiting Tissue Biomechanics, Optics Express, 2004, 12(19):4558-4572.
Chang, et al., Clinical Perspective of Coronary Computed Tomographic Angiography in Diagnosis of Coronary Artery Disease, Circulation Journal, 2011, 75(2):246-252.
Chau, et al., Mechanical Analysis of Atherosclerotic Plaques Based on Optical Coherence Tomography, Annals of Biomedical Engineering, 2004, 32:1494-1503.
Chau, et al., Fingerprint and High-Wavenumber Raman Spectroscopy in a Human-Swine Coronary Xenograft In Vivo, Journal of Biomedical Optics, 2008, 13:040501.
Chen, et al., Experimental and Theoretical Analysis of Core-To-Core Coupling on Fiber Bundle Imaging, Optics Express, 2008, 16:21598-21607.
Cheruvu, et al., Frequency and Distribution of Thin-Cap Fibroatheroma and Ruptured Plaques in Human Coronary Arteries, J. Am. Coll. Cardiol., 2007, 50:940-949.
Dasgupta, et al., Microheology of Cross-Linked Polyacrylamide Networks, Phys. Rev. E, 2005, 71:021504.
Desai, et al., Microfabricated Post Array Detectors (mPADs): An Approach to Isolate Mechanical Forces, Journal of Visualized Experiments, 2007, pp. 1-4.
Dubaj, et al., Optic Fibre Bundle Contact Imaging Probe Employing a Laser Scanning Confocal Microscope, Journal of Microscopy, 2002, 207:108-117.
Dunn, et al., Dynamic Imaging of Cerebral Blood Flow Using Laser Speckle, J. Cereb. Blood Flow Metab., 2001, 21:195-201.
Finet, et al., Biomechanical Interaction Between Cap Thickness, Lipid Core Composition and Blood Pressure in Vulnerable Coronary Plaque: Impact on Stability or Instability, Coronary Artery Disease, 2004, 15(1):13-20.
Finet, et al., Morphological and Biomechanical Aspects of Vulnerable Coronary Plaque, Arch. Mal. Coeur. Vaiss, 2007, 100:547-553.
Finn, et al., Concept of Vulnerable/Unstable Plaque, Arterioscler. Thromb. Vasc. Biol., 2010, 30:1282-1292.
Garcia-Garcia, et al., Tissue Characterization Using Intravascular Radiofrequency Data Analysis: Recommendations for Acquisition, Analysis Interpretation and Reporting, EuroIntervention, 2009, 5(2):177-189.
Gobel, et al., Miniaturized Two-Photon Microscope Based on a Flexible Coherent Fiber Bundle and a Gradient-Index Lens Objective, Optics Letters, 2004, 29:2521-2523.
Grube, et al., Intracoronary Imaging with Optical Coherence Tomography: A New High-Resolution Technology Providing Striking Visualization in the Coronary Artery, Circulation, 2002, 106(18):2409-2410.
Hajjarian, et al., Intravascular Laser Speckle Imaging Catheter for the Mechanical Evaluation of the Arterial Wall, J. Biomed. Optics, 2011, 16(2):026005-1-026005-7.
Hajjarian, et al., Evaluating the Viscoelastic Properties of Tissue from Laser Speckle Fluctuations, Scientific Reports, 2012, 2:316.
Han, et al., Effect of Multimodal Coupling in Imaging Microendoscopic Fiber Bundle on Optical Coherence Tomography, Appl. Phys. B, 2012, 106:635-643.
Irimia, Microfluidic Technologies for Temporal Perturbations of Chemotaxis, Annu. Rev. Biomed. Eng., 2010, 12:259-284.
Ishibashi, et al., Quantitative Colorimetry of Atherosclerotic Plaque Using the L* a* b* Color Space During Angioscopy for the Detection of Lipid Cores Underneath Thin Fibrous Caps, International Journal of Cardiovascular Imaging, 2007, 23(6):679-691.

(56) References Cited

OTHER PUBLICATIONS

Jang, et al., Visualization of Tissue Prolapse Between Coronary Stent Struts by Optical Coherence Tomography: Comparison with Intravascular Ultrasound, Circulation, 2001, 104(22):2754-2754.
Jang, et al., Visualization of Coronary Atherosclerotic Plaques in Patients Using Optical Coherence Tomography: Comparison with Intravascular Ultrasound, Journal of the American College of Cardiology, 2002, 39(4):604-609.
Jang, et al., In Vivo Characterization of Coronary Atherosclerotic Plaque by Use of Optical Coherence Tomography, Circulation, 2005, 111:1551-1555.
Juskaitis, et al., Real-Time White Light Reflection Confocal Microscopy Using a Fibre-Optic Bundle, Scanning, 1997, 19:15-19.
Kirkpatrick, et al., Optical Vortex Behavior in Dynamic Speckle Fields, J. Biomed. Opt., 2012, 17:050504.
Kolodgie, et al., The Thin-Cap Fibroatheroma: A Type of Vulnerable Plaque: The Major Precursor to Acute Coronary Syndromes, Curr. Opin. Cardiol., 2001, 16:285-292.
Kolodgie, et al., Free Cholesterol in Atherosclerotic Plaques: Where Does It Come From?, Curr. Opin. Lipidol., 2007, 18:500-507.
Koshiba, et al., Multi-Core Fiber Design and Analysis: Coupled-Mode Theory and Coupled-Power Theory, Optics Express, 2011, 19:B102-B111.
Koskinas, et al., Natural History of Experimental Coronary Atherosclerosis and Vascular Remodeling in Relation to Endothelial Shear Stress: A Serial, In Vivo Intravascular Ultrasound Study, Circulation, 2010, 121(19):2092-2101.
Lee, et al., Prediction of Mechanical Properties of Human Atherosclerotic Tissue by High-Frequency Intravascular Ultrasound Imaging. An In Vitro Study, Arteriosclerosis, Thrombosis, and Vascular Biology, 1992, 12(1):1-5.
Lee, et al., Atherosclerotic Lesion Mechanics Versus Biology, Z. KardioL, 2000, 89:80-84.
Liebson, et al., Intravascular Ultrasound in Coronary Atherosclerosis: A New Approach to Clinical Assessment, Am. Heart J., 1992, 123:1643-1660.
Loree, et al., Mechanical Properties of Model Atherosclerotic Lesion Lipid Pools, Arterioscler. Thromb., 1994, 14:230-234.
MacNeill, et al., Focal and Multi-Focal Plaque Macrophage Distributions in Patients with Acute and Stable Presentations of Coronary Artery Disease, Journal of the American College of Cardiology, 2004, 44(5):972-979.
Madjid, et al., Intracoronary Thermography for Detection of High-Risk Vulnerable Plaques, J. Am. Coll. Cardiol., 2006, 47:C80-C85.
Manka, et al., Dynamic 3-Dimensional Stress Cardiac Magnetic Resonance Perfusion Imaging: Detection of Coronary Artery Disease and Volumetry of Myocardial Hypoenhancement Before and After Coronary Stenting, Journal of the American College of Cardiology, 2611, 57(4):437-444.
Marenzi, et al., Contrast Volume During Primary Percutaneous Coronary Intervention and Subsequent Contrast-Induced Nephropathy and Mortality, Ann. Intern. Med., 2009, 150:170-177.
Mason, et al., Optical Measurements of Frequency-Dependent Linear Viscoelastic Moduli of Complex Fluids, Physical Review Letters, 1995, 74:1250-1253.
Mizukoshi, et al., Clinical Classification and Plaque Morphology Determined by Optical Coherence Tomography in Unstable Angina Pectoris, Am. J. Cardiol., 2010, 106:323-328.
Moreno, et al., Detection of Lipid Pool, Thin Fibrous Cap, and Inflammatory Cells in Human Aortic Atherosclerotic Plaques by Near-Infrared Spectroscopy, Circulation, 2002, 105(8):923-927.
Motoyama, et al., Computed Tomographic Angiography Characteristics of Altherosclerotic Plaques Subsequently Resulting in Acute Coronary Syndrome, J. Am. Coll. Cardiol., 2009, 54:49-57.
Murray, et al., Virtual Histology Imaging in Acute Coronary Syndromes: Useful or Just a Research Tool?, J. Invasive Cardiol., 2010, 22:84-91.
Nadkarni, et al., Characterization of Atherosclerotic Plaques by Laser Speckle Imaging, Circulation, 2005, 112:885-892.

Nadkarni, et al., Measurement of Fibrous Cap Thickness in Atherosclerotic Plaques by Spatiotemporal Analysis of Laser Speckle Images, J. Biomed. Opt., 2006, 11:021006.
Nadkarni, et al., Measurement of Collagen and Smooth Muscle Cell Content in Atherosclerotic Plaques Using Polarization-Sensitive Optical Coherence Tomography, Journal of the American College of Cardiology, 2007, 49(13):1474-1481.
Nadkarni, et al., Laser Speckle Imaging of Atherosclerotic Plaques Through Optical Fiber Bundles, J. BIomed. Opt., 2008, 13:054016.
Nadkarni, et al., Evaluation of Collagen in Atherosclerotic Plaques: The Use of Two Coherent Laser-Based Imaging Methods, Lasers Med. Sci., 2009, 24:439-445.
Newby, et al., Fibrous Cap Formation or Destruction—The Critical Importance of Vascular Smooth Muscle Cell Proliferation, Migration and Matrix Formation, Cardiovascular Research, 1999, 41(2):345-360.
Ohayon, et al.,Influence of Residual Stress/Strain on the Biomechanical Stability of Vulnerable Coronary Plaques: Potential Impact for Evaluating the Risk of Plaque Rupture, American Journal of Physiology—Heart and Circulatory Physiology, 2007, 293(3):H1987-H1996.
Papafaklis, et al., In-Vivo Assessment of the Natural History of Coronary Atherosclerosis: Vascular Remodeling and Endothelial Shear Stress Determine the Complexity of Atherosclerotic Disease Progression, Current Opinion in Cardiology, 2010, 25(6):627-638.
Reichenbach, et al., Numerical Analysis of Light Propagation in Image Fibers or Coherent Fiber Bundles, Optics Express, 2007, 15:2151-2165.
Rekhter, et al., Hypercholesterolemia Causes Mechanical Weakening of Rabbit Atheroma: Local Collagen Loss as a Prerequisite of Plaque Rupture, Circulation Research, 2000, 86:101-108.
Richardson, et al., Influence of Plaque Configuration and Stress Distribution on Fissuring of Coronary Atherosclerotic Plaques, Lancet, 1989, 334(8669):941-944.
Richardson, Biomechanics of Plaque Rupture: Progress, Problems and New Frontiers, Annals of Biomedical Engineering, 2002, 30:524-536.
Rogers, et al., Characterization of Signal Properties in Atherosclerotic Plaque Components by Intravascular MRI, Arterioscler. Thromb. Vasc. Biol., 2000, 20:1824-1830.
Sadat, et al., Biomechanical Structural Stresses of the Atherosclerotic Plaques, Expert Rev. Cardiovasc. Ther., 2010, 8:1469-1481.
Sangiorgi, et al., Plaque Vulnerability and Related Coronary Event Prediction by Intravascular Ultrasound with Virtual Histology: "It's a Long Way to Tipperary?", Catheterization and Cardiovascular Interventions 2007, 70(2):203-210.
Schaar, et al., Characterizing Vulnerable Plaque Features with Intravascular Elastography, Circulation, 2003, 108:2636-2641.
Schmermund, et al., Intracoronary Thermography, Herz, 2003, 28(6):505-512.
Schroeder, et al., Vulnerable and Dangerous Coronary Plques, Atherosclerosis, 1995, 188:S141-S149.
Serruys, et al., From Postmortem Characterization to the In VIvo Detection of Thin Capped Fibroatheromas: The Missking Link Toward Percutaneous Treatment: What if Diogenes Would Have Found What He Was Looking For?, Journal of the American College of Cardiology, 2007, 50(10):950-952.
Shah, et al., Mechanisms of Plaque Vulnerability and Rupture, J. Am. Coll. Cardiol., 2003, 41:S15-S22.
Skorobogatiy, et al., Full-Vectorial Coupled Mode Theory for the Evaluation of Macro-Bending Loss in Multimode Fibers, Application to the Hollow-Core Photonic Bandgap Fibers, Optics Express, 2008, 16(19):14945-14953.
Snyder, et al., Coupled-Mode Theory for Optical Fibers, Journal of the Optical Society of America, 1972, 62:1267-1277.
Song, et al., Endoscopic Laser Speckle Contrast Imaging System Using a Fibre Image Guide, In Biomedical Applications of Light Scattering V, vol. 7907, p. 79070F. International Society for Optics and Photonics, 2011.
Stone, et al., PROSPECT: An Imaging Study in Patients with Unstable Atherosclerotic Lesions, 2009, www.clinicaltrials.gov.

(56) References Cited

OTHER PUBLICATIONS

Tan, et al., Cells Lying on a Bed of Microneedles: An Approach to Isolate Mechanical Force, Proc. Natl. Acad. Sci. USA, 2003, 100:1484-1489.

Tanaka, et al., Lipid Rich Plaque and Myocardial Perfusion After Successful Stenting in Patients with Non-ST-Segment Elevation Acute Coronary Syndrome: An Optical Coherence Tomography Study, European Heart Journal, 2009, 30(11):1348-1355.

Tang, et al., Effect of a Lipid Pool on Stress/Strain Distributions in Stenotic Arteries: 3-D Fluid-Structure Interactions (FSI) Models, J. Biomech. Eng., 2004, 126:363-370.

Tearney, et al., Scanning Single Mode Fiber Optic Catheter—Endoscope for Optical Coherence Tomography, Optics Letters, 1996, 21:543-545.

Tearney, et al., Atherosclerotic Plaque Characterization by Spatial and Temporal Speckle Pattern Analysis, Optics, Letters, 2002, 27:533-535.

Tearney, et al., Quantification of Macrophage Content in Atherosclerotic Plaques by Optical Coherence Tomography, Circulation, 2003, 107:113-119.

Tearney, et al., Three-Dimensional Coronary Artery Microscopy by Intracoronary Optical Frequency Domain Imaging, JACC: Cardiovascular Imaging, 2008, 1:752-761.

Virmani, et al., Lessons from Sudden Coronary Death: A Comprehensive Morphological Classification Scheme for Atherosclerotic Lesions, Arteriosclerosis, Thrombosis, and Vascular Biology, 2000, 20(5):1262-1275.

Virmani, et al., Vulnerable Plaque: The Pathology of Unstable Coronary Lesions, J. Interv. Cardiol., 2002, 15:439-446.

Wang, et al., MCML—Monte Carlo Modeling of Light Transport in Multi-Layered Tissues, Computer Methods and Programs in Biomedicine, 1995, 47(2):131-146.

Waxman, et al., In Vivo Validation of a Catheter-Based Near-Infrared Spectroscopy System for Detection of Lipid Core Coronary Plaques: Initial Results of the SPECTACL Study, JACC: Cardiovascular Imaging, 2009, 2(7):858-868.

Williamson, et al., On the Sensitivity of Wall Stresses in Diseased Arteries to Variable Material Properties, J. Biomech. Eng., 2003, 125:147-155.

Xie, et al., Fiber-Optic-Bundle-Based Optical Coherence Tomography, Optics Letters, 2005, 30:1803-1805.

Yabushita, et al., Characterization of Human Atherosclerosis by Optical Coherence Tomography, Circulation, 2002, 106:1640-1645.

Zhang, et al., Correcting the Detrimental Effects of Nonuniform Intensity Distribution on Fiber-Transmitting Laser Speckle Imaging of Blood Flow, Optics Express, 2012, 20(1):508-517.

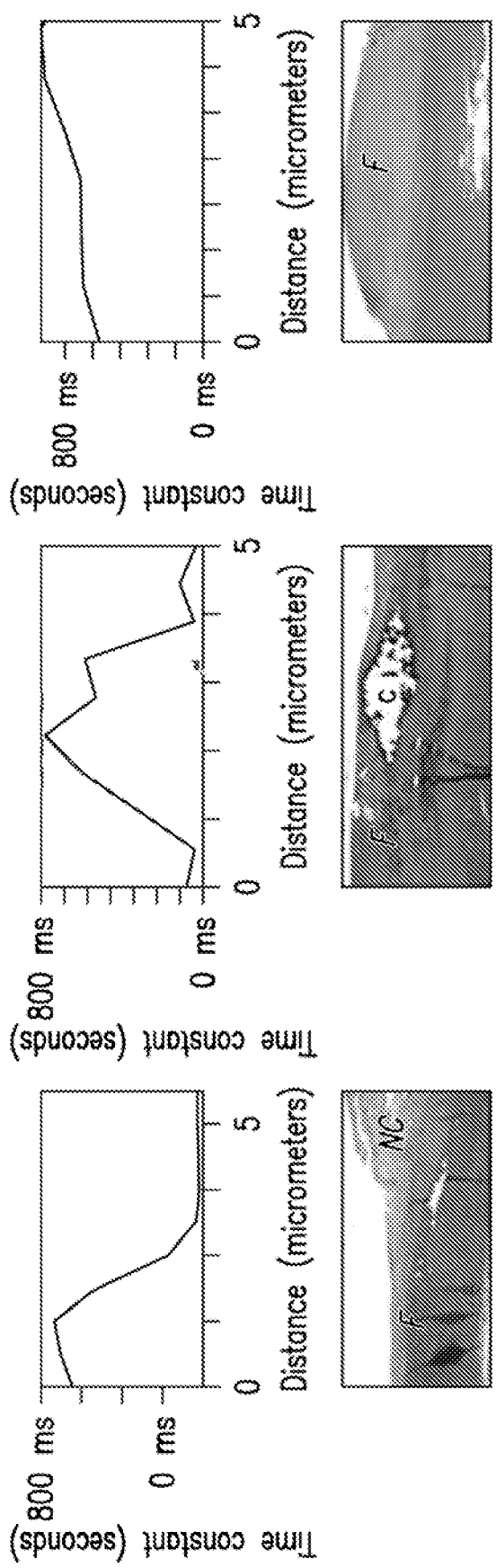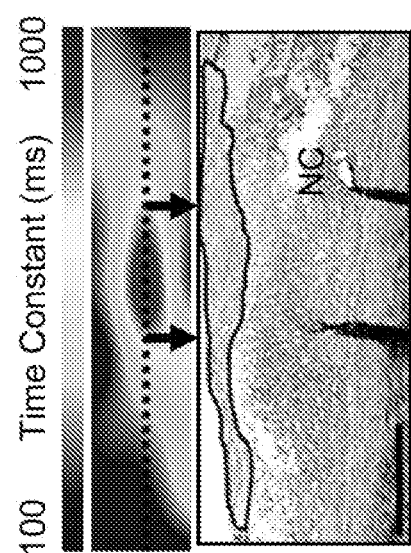
FIG. 7A  FIG. 7B  FIG. 7C
FIG. 8

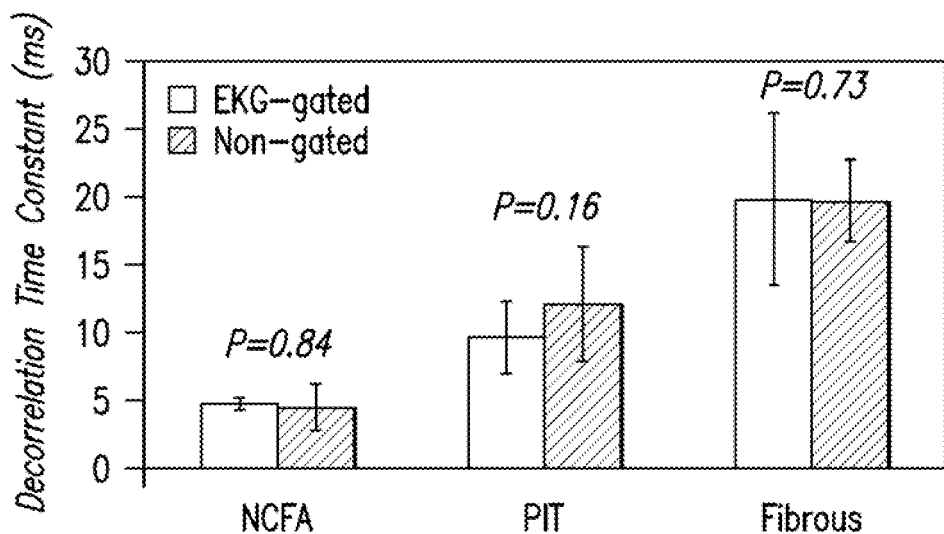
FIG.13A
FIG.13B
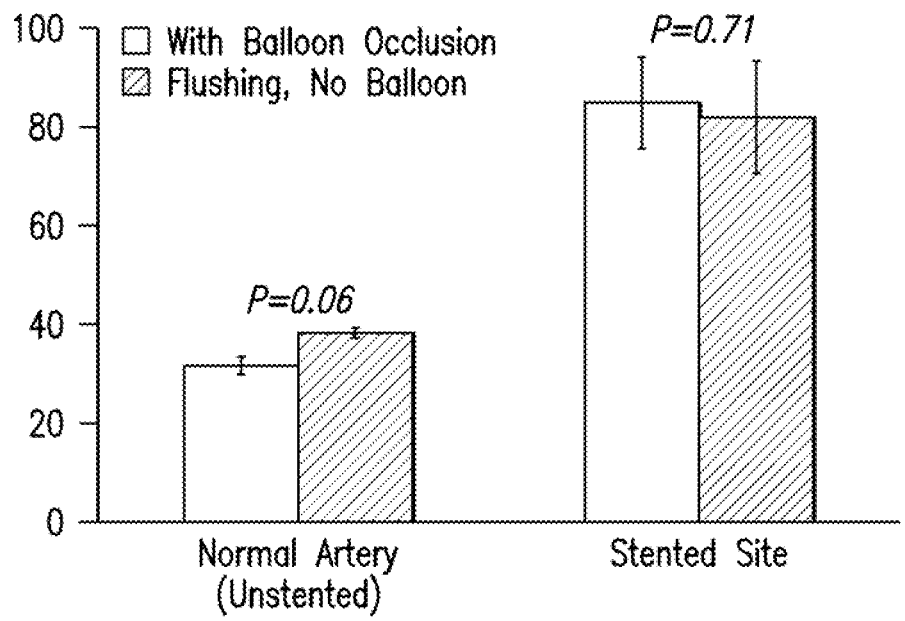
FIG.14

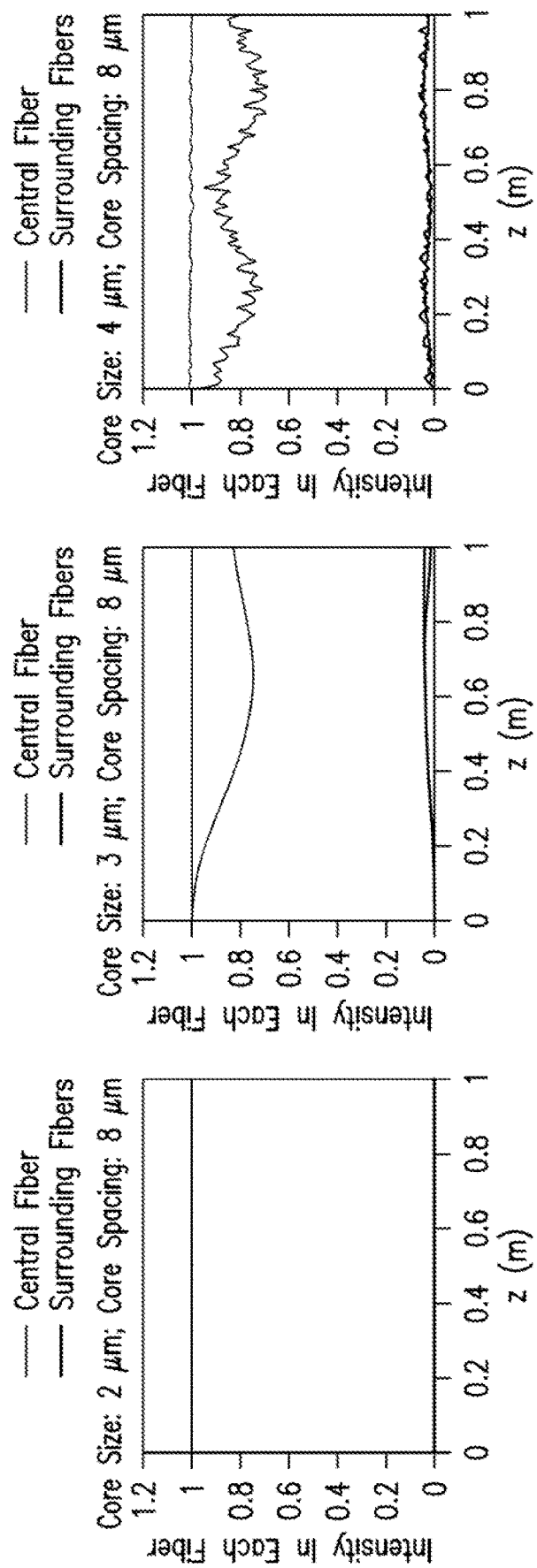

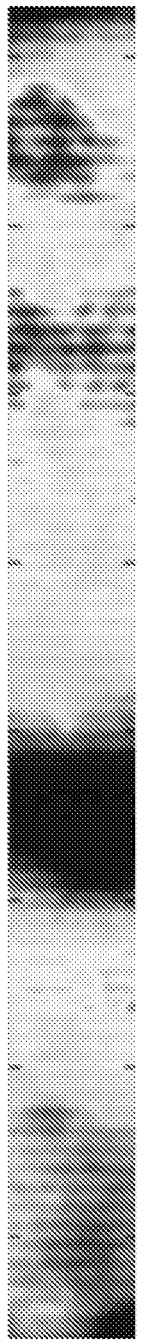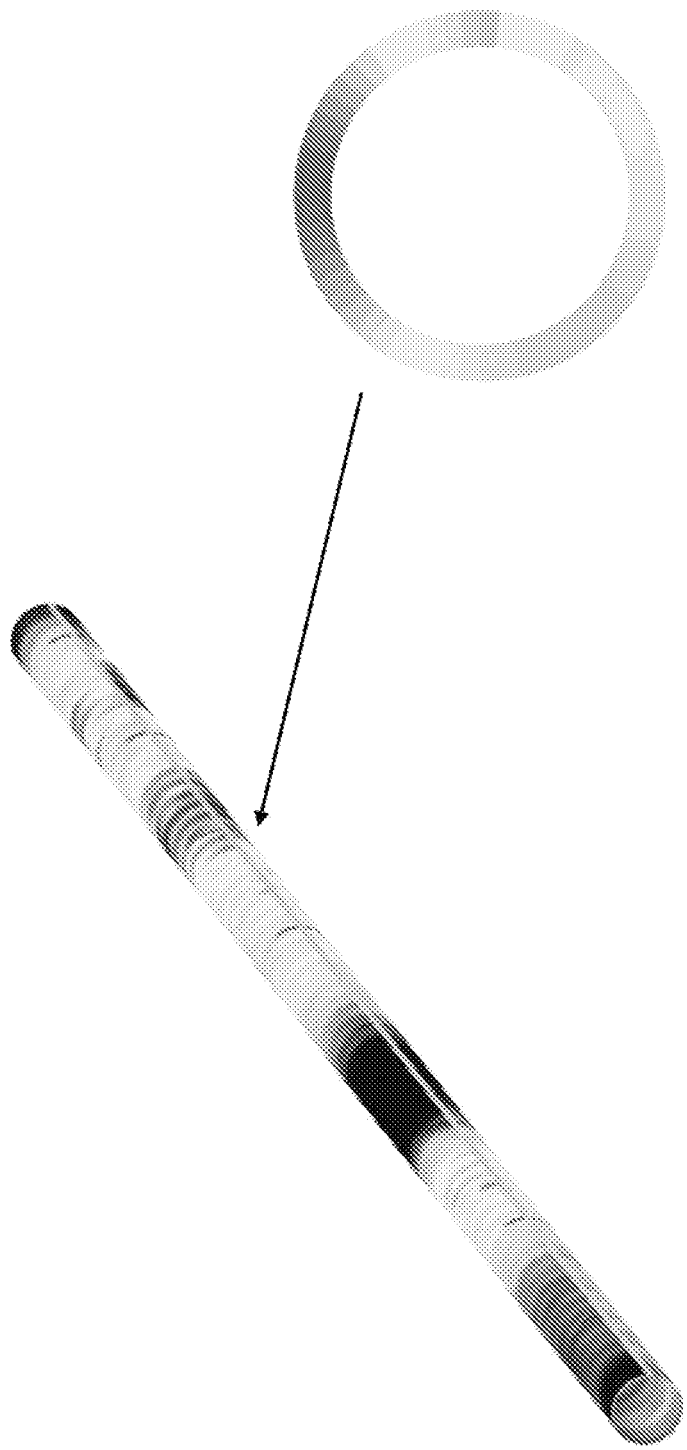
FIG. 32A
FIG. 32B
FIG. 32C

APPARATUS, DEVICES AND METHODS FOR OBTAINING OMNIDIRECTIONAL VIEWING BY A CATHETER

CROSS-REFERENCE TO RELATED APPLICATION(S)

This application relates to and claims priority from U.S. Patent Application Ser. Nos. 61/836,716 filed on Jun. 19, 2013, 61/934,454 filed on Jan. 31, 2014, and 61/905,893 filed on Nov. 19, 2013, the entire disclosures of which are incorporated herein by reference.

FIELD OF THE DISCLOSURE

The present disclosure relates generally to viewing by a catheter, and more specifically, to exemplary embodiments of exemplary devices, apparati and methods for omnidirectional (e.g., laser speckle) imaging, and viewing by a catheter.

BACKGROUND INFORMATION

Despite major advances in coronary interventions and pharmacotherapies, acute myocardial-infarction ("AMI") remains the leading cause of death, annually claiming over 10 million lives worldwide. AMI can be caused by coronary thrombosis that can frequently result from the rupture of vulnerable plaque. If vulnerable plaques could be identified and treated prior to rupture, the incidence of AMI could be substantially reduced, and tens of thousands of lives could be saved. A key challenge in realizing this preventative paradigm can be that plaques with vulnerable morphology occur at multiple sites in the coronary tree, and therefore, additional knowledge of plaque mechanical stability can be imperative in order to accurately identify plaques with the highest risk of rupture.

Laser speckle patterns (see, e.g., References 96 and 97) can be granular intensity patterns that can arise from the interference of coherent light scattered from randomly distributed light scattering particles. The scattered photons can experience different path lengths. The phase difference between partial waves can cause constructive or destructive interference, and can produce randomly distributed high or low intensity spots called speckles. The moving scatterers can introduce different phase shifts for different partial waves, and can change the interference between partial waves, which can lead to temporally varying speckle patterns. The temporal evolution of speckles can provide information of scatterers' movement (see, e.g., Reference 98), and can further the information of the media properties which can influence the scattering particles motion (e.g., viscoelasticity). (See, e.g., References 99-103). Laser speckle imaging ("LSI") techniques have been applied in medical diagnosis to retrieve information about tissue perfusion (see, e.g., References 98 and 104), and mechanical properties (see, e.g., References 99-103) of tissues from dynamic speckle patterns. To perform LSI in vivo, coherent light can be delivered via an optical fiber, and the reflected laser speckle patterns can be collected and transmitted via optical fiber bundles ("OFB") incorporated within small diameter endoscopes. (see, e.g., References 99-103 and 105-107).

Due to their small transverse dimensions and flexibility, optical fiber bundles have been widely used in medical endoscopy (see, e.g., References 108-112), and in other minimally-invasive approaches, to enable the capability of being guided through coronaries or other conduits of human body. The large numerical aperture ("NA") can compare to the common optical fiber, and high cores density give fiber bundles can have high light collection efficiency. The high compact density of cores of fiber bundles can also provide high resolution imaging. However in LSI, the light can be highly coherent unlike the white light endoscopy (see, e.g., Reference 113 in which the interference effect between cores can be neglected. The high density of cores can introduce strong coupling between adjacent fibers, which can severely affect the image quality transmitted through fiber bundles. Each fiber in the fiber bundles can support multiple guided modes, and the field of these modes can extend into the cladding, and can overlap with the mode fields of surrounding fibers. (See, e.g., Reference 114). Such overlapping can lead to the coupling, between modes, of individual fibers, and interfiber power exchange between adjacent fibers known as the optical crosstalk between fibers. Consequently, the transmitted images, or laser speckles, can be modulated by the inter-fiber crosstalk in fiber bundles due to mode coupling. During the in vivo LSI, the movement of fiber bundles due to the bulk motion of surrounding tissue can be hard to prevent. The movement of a fiber bundle can cause the core coupling changing with time, and the modulation to the transmitted speckles can be varying with time. As a result, the time-varying coupling between cores can cause erroneous speckle temporal statistics, and can reduce the accuracy of an LSI analysis. (See, e.g., Reference 100).

The coupling between fibers modes of different fibers in fiber bundles has been extensively studied based on the fiber core size, core spacing, NA and non-uniformity of cores. (See, e.g., References 115-117). However these studies mainly focused on the coupling between fundamental modes of neighboring fibers. Only a few numerical simulations (see, e.g., Reference 118) and experiments (see, e.g., References 100, 116 and 119) have been conducted to show the fiber crosstalk in multimode fiber bundles and its influence on image transmission. These numerical simulations (see, e.g., Reference 118) only simulated fields propagating a few mm along the length of bundles due to the intensive computing required. Previous experiments have demonstrated leached fiber bundles can effectively reduce the cross talk between cores, and can obtain a relatively stable temporal decorrelation function of transmitted speckles during bundles motion because of large core-to-core separation due to manufacturing processes of leached fiber bundle. (See, e.g., Reference 100). However, the effect of mode coupling between neighboring optical fibers on the transmission of laser speckles may not be well understood.

In order to conduct laser speckle imaging via a catheter, light can be guided through an optical fiber and distal optical components to illuminate a single spot on the cylindrical lumen to collect reflected speckle patterns via a single fiber or collection of optical fibers (e.g., a fiber bundle). To conduct circumferential mapping, the catheter can be rotated during pull-back. However, this can introduce motion artifacts during catheter rotation that can confound the ability to accurately analyze laser speckle patterns from tissue.

Thus, it may be beneficial to provide an exemplary device, apparatus and method for viewing by a catheter, which can overcome at least some of the deficiencies described herein above.

SUMMARY OF EXEMPLARY EMBODIMENTS

These and other objects of the present disclosure can be achieved by provision of an apparatus for obtaining information regarding a biological structure(s), which can include, for example a light guiding arrangement which can include a fiber through which an electromagnetic radiation(s) can be propagated, where the electromagnetic radiation can be provided to or from the structure. An at least partially reflective arrangement can have multiple surfaces, where the reflecting arrangement can be situated with respect to the optical arrangement such that the surfaces thereof each can receive a(s) beam of the electromagnetic radiations instantaneously, and a receiving arrangement(s) which can be configured to receive the reflected radiation from the surfaces which include speckle patterns.

In some exemplary embodiments, a polarizing arrangement(s) can be included which can receive the electromagnetic radiation, and prevent receipt of a same polarization from returning to the receiving arrangement(s). The reflective arrangement can have a portion(s) with a shape of a cone, a polygon or a pyramid. An optical arrangement can be included which can be configured to receive the electromagnetic radiation(s). The optical arrangement can include a GRIN lens, a ball lens, or an imaging lens. The number surfaces of the reflective arrangement can be 2 or more, 4 or more, or 6 or more. The light guiding arrangement can include a configuration which can split the electromagnetic radiation to further radiations having different wavelengths where the multiple surfaces can reflect the further radiations, and where the receiving arrangement(s) can be further configured to receive the reflected further radiations provided at the different wavelengths.

In another exemplary embodiment of the present disclosure can be an apparatus for obtaining information regarding a biological structure(s), which can include, for example, a catheter arrangement which can include a fiber(s) through which an electromagnetic radiation(s) can be propagated, where the electromagnetic radiation can be provided to or from the structure. A pullback arrangement can be configured to facilitate a pullback of the catheter arrangement, and a detector arrangement can includes a plurality of sensors, the sensors being coupled to a surface of a portion(s) of the catheter arrangement, and configured to move together with the pullback arrangement, and receive optical information associated with the electromagnetic radiation(s) provided from the structure so as to generate the information.

In some exemplary embodiments of the present disclosure, the sensors can be directly attached to the surface of the portion(s) of the catheter arrangement. The detector arrangement can include a CMOS sensor, a CCD sensor, a photodetector or a photodetector array. The fiber(s) can include a plurality of fibers, or a fiber bundle. For example, at an illumination wavelength between about 630-720 nm, the fiber bundle can have (i) a core diameter of 3.0 μm±0.3 μm with a fluctuation in core diameter of ±0.03 μm to ±0.3 μm, (ii) a numerical aperture of at least 0.35, and (iii) a core spacing of 8.0 urn±0.5 μm. The pullback arrangement can be controlled by a motor(s). The motor(s) can control the pullback arrangement such that the pullback arrangement can move the catheter and detector arrangements in a stepped manner. The motor(s) can control the pullback arrangement to rotate a drive shaft or distal optics. The motor(s) can be configured to keep the catheter stationary.

In some exemplary embodiments of the present disclosure, adjacent times for the movements of the catheter and detector arrangement can be between 5 msec and 100 msec. The sensors can receive the optical information that can be associated with the electromagnetic radiation provided at different wavelengths. A filter arrangement can be configured to filter the optical information based on the electromagnetic radiation provided at different wavelengths. The catheter arrangement can include a drive shaft arrangement which can hold the fiber(s) and can be directly connected to the pullback arrangement. The drive shaft arrangement can further hold distal optics. The motor(s) can control the pullback arrangement such that the pullback arrangement can move the catheter and detector arrangements continuously at a predetermined speed or a variable speed.

In another exemplary embodiment of the present disclosure is an apparatus for imaging a portion(s) of a biological structure, which can include, for example a radiation providing arrangement which can be configured to forward a first electromagnetic radiation(s) to the structure at multiple illumination locations. A detector arrangement can be is configured to receive a second electromagnetic radiation(s) from the multiple locations of the structure. A pullback arrangement which, during the forwarding of the first electromagnetic radiation, can be configured to pull back the radiation arrangement(s) of the detector arrangement. The detector arrangement can be further configured to image the portion(s) of the structure based on the second electromagnetic radiation(s), without a rotation of the radiation providing arrangement.

In some exemplary embodiments of the present disclosure, the first electromagnetic radiation(s) can be forwarded to the structure at multiple illumination locations substantially simultaneously. The second electromagnetic radiation(s) can be received from the multiple locations of the structure substantially simultaneously. The second electromagnetic radiation(s) ca provides information regarding a speckle pattern reflected from the portion(s) of the structure. The speckle pattern can have an intensity that can vary in time. The variation of the intensity of the speckle pattern can provide information regarding mechanical properties of the portion(s) of the structure, which can be determined by the detector arrangement. The pullback arrangement can be controlled by a motor(s). The motor(s) can control the pullback arrangement to rotate a drive shaft or distal optics.

In another exemplary embodiment of the present disclosure is a method for imaging portion(s) of a biological structure, which can include, for example, using a radiation providing arrangement, forwarding a first electromagnetic radiation(s) to the structure at multiple illumination locations, using a detector arrangement, receiving a second electromagnetic radiation(s) from the multiple locations of the structure, and pulling back the radiation arrangement(s) of the detector arrangement. The detector arrangement can be configured to image substantially an entire surface of the portion(s) of the structure based on the second electromagnetic radiation(s), without a rotation of the radiation providing arrangement.

In some exemplary embodiments of the present disclosure, the first electromagnetic radiation(s) can be forwarded to the structure at multiple illumination locations substantially simultaneously. The second electromagnetic(s) radiation can be received from the multiple locations of the structure substantially simultaneously.

In another embodiment of the present disclosure, a system, method and computer-accessible medium can be provided for obtaining information regarding a biological structure(s), which can include, for example, receiving information related to a radiation(s) reflected from the biological structure(s) including a speckle pattern(s), and generating an image of the biological structure(s) based on the information. Pixilation artifacts can be removed from the speckle pattern(s). A speckle intensity fluctuation of the speckle pattern(s) can be determined by, for example measuring a change of multiple mirror facets over time. A background fluctuation or a source fluctuation from can be removed from the speckle pattern(s). Non-fluctuating speckles can be filtered from the speckle pattern(s). A phase fluctuation of the reflected radiation(s) can be determined to, for example, characterize the tissue.

In another embodiment of the present disclosure, a method of reducing inter-fiber crosstalk in a fiber optic bundle can be provided, which can include, for example providing a fiber optic bundle comprising a plurality of core fibers each having a core diameter of 3.0 μm±0.3 μm with a fluctuation in core diameter of ±0.03 μm to ±0.3 μm, a numerical aperture of at least 0.35, and the fiber optic bundle having a core spacing of 8.0 urn±0.5 μm. Receiving a light into the fiber optic bundle, where the fiber optic bundle has a reduced inter-fiber crosstalk. The diameter of the core fibers can be 3.0 μm±0.2 μm. The core fibers can be 3.0 μm±0.1 μm. The fluctuation of the core diameter can be ±0.06 μm to ±0.2 μm. The fluctuation of the core diameter can be approximately ±0.1 μm. The numerical aperture can be between 0.38 and 0.41. The core spacing can be 8.0 μm±0.3 μm. The core spacing can be 8.0 μm±0.2 μm. The fiber optic bundle can have an inter-fiber crosstalk that can be at least 10% less than the inter-fiber crosstalk within a leached fiber optic image bundle defined as SCHOTT North America Type 1 at a propagation distance of 0.5 m using 690 nm radiation. The fiber optic bundle can have an inter-fiber crosstalk that can be negligible.

In another exemplary embodiment of the present disclosure is, an apparatus can be provided for laser speckle imaging that has low inter-fiber crosstalk, which can include, for example a coherent radiation source, a fiber optic bundle configured to receive radiation from the coherent radiation source including a plurality of core fibers having a core diameter, a fluctuation in core diameter, a numerical aperture, and a core spacing, where each of the core diameter, the fluctuation in core diameter, the numerical aperture, and the core spacing can be determined using coupled mode theory ("CMT"). One or more optical elements can be configured to direct coherent radiation from the fiber optic bundle to a tissue and collect radiation from the tissue. A detector can be configured to receive a speckle pattern from the one or more optical elements. The diameter of the core fibers can be 3.0 μm±0.3 μm. The diameter of the core fibers can be 3.0 μm±0.2 μm. The diameter of the core fibers can be 3.0 μm±0.1 μm. The fluctuation of the core diameter can be ±0.03 μm to ±0.3 μm. The fluctuation of the core diameter can be ±0.05 μm to ±0.2 μm. The fluctuation of the core diameter can be approximately ±0.1 μm. The numerical aperture can be at least 0.35. The numerical aperture can be between 0.38 and 0.41. The core spacing can be 8.0 μm±0.5 μm. The core spacing can be 8.0 μm±0.3 μm. The core spacing can be 8.0 μm±0.2 μm. The fiber optic bundle can include a core diameter of 3.0 μm±0.3 μm with a fluctuation in core diameter of ±0.1 μm to ±0.3 μm, and a numerical aperture of at least 0.35, and the fiber optic bundle having a core spacing of 8.0 μm±0.5 μm. The numerical aperture and the core spacing can depend on a wavelength of the coherent radiation source. The core diameter can depend on the fiber size, the core spacing or the numerical aperture.

In another exemplary embodiment of the present disclosure, a method can be provided for tissue analysis, which can include, for example illuminating a first cylindrical section(s) of a lumen wall with coherent or partially coherent light by passing the light through a facet(s) of a multiple-faceted pyramidal mirror, receiving light reflected from the first cylindrical section of a lumen wall at the mirror, illuminating a second cylindrical section(s) of a lumen wall with coherent or partially coherent light at a time different from the first illuminating step by passing the light through a second facet(s) of the multiple-faceted pyramidal mirror, receiving light reflected from the second cylindrical section of a lumen wall at the mirror, receiving light reflected from the mirror at a detector and forming series of speckle patterns, and analyzing changes in the speckle patterns at time intervals sufficient to measure changes caused by microscopic motion of objects within the tissue.

According to a still further exemplary embodiments of the present disclosure, the illumination can occur by first illuminating cylindrical section of a lumen wall through either a single facet of the pyramidal mirror at a time, or multiple facets of the pyramidal mirror at one time, where the facets are not adjacent to each other. The multiple faceted pyramidal mirror can be a four-sided mirror and the cylindrical section of a lumen wall can be illuminated through two non-adjacent facets simultaneously and then the cylindrical section of a lumen wall can be illuminated through the other two non-adjacent facets simultaneously. The multiple faceted pyramidal mirror can be a six-sided mirror and the cylindrical section of a lumen wall is illuminated through two or three non-adjacent facets simultaneously.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 7A-7C are exemplary graphs illustrating the evaluation of spatial heterogeneity by beam scanning according to an exemplary embodiment of the present disclosure;

FIG. 8 is an exemplary colormap illustrating depth imaging in a thin cap fibroatheroma according to an exemplary embodiment of the present disclosure;

FIGS. 13A and 13B is an exemplary graph illustrating average τ calculated for 3 plaque groups according to an exemplary embodiment of the present disclosure;

FIG. 14 is an exemplary graph illustrating τ calculated in a swine using exemplary PBO procedures according to an exemplary embodiment of the present disclosure;

FIGS. 22A-22C are exemplary graphs illustrating core spacing according to an exemplary embodiment of the present disclosure;

FIGS. 31B-1 and 31B-2 is a set of 8τ maps of gels A, B, B, and C from FIG. 31A according to an exemplary embodiment of the present disclosure;

FIGS. 32A-32C shows illustrations of an example of wrapping 2D time constant maps onto a cylinder to form a cylindrical view of the time constant maps according to an exemplary embodiment of the present disclosure;

Figure 1:
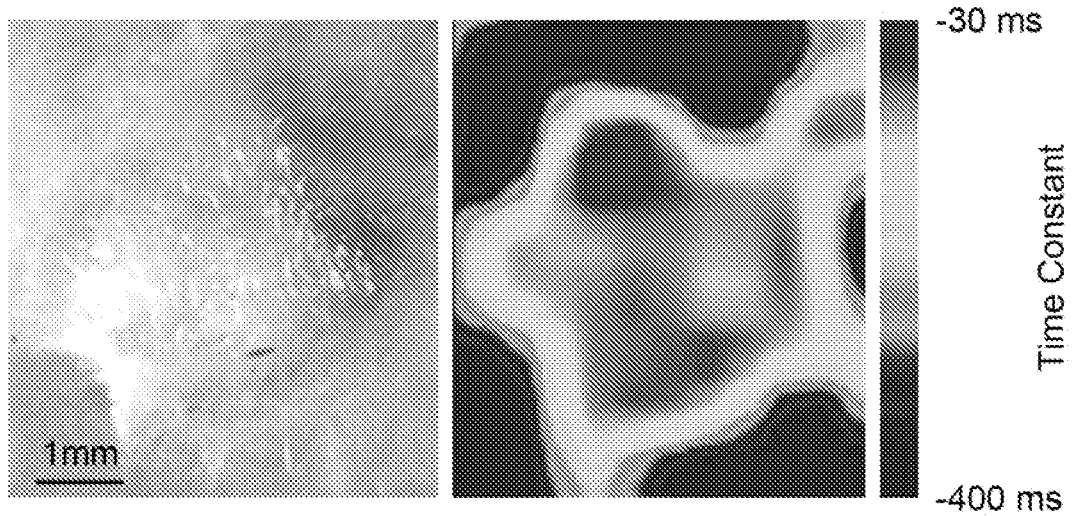
FIG. 1 is a set of exemplary images of a plaque and a color map of the plaque according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION OF EXEMPLARY EMBODIMENTS

One exemplary object of the present disclosure can be to provide, for patient use, an optical system and method that can be termed Intracoronary Laser Speckle Imaging ("ILSI"), which can evaluate plaque viscoelastic properties, known to be intimately linked with the risk of coronary plaque rupture. It has been determined that plaque rupture can occur when the atheroma, with severely compromised viscoelastic properties, can fail to withstand stresses exerted upon it. Therefore, an important ability of an ILSI exemplary system and method, according to an exemplary embodiment of the present disclosure, can be to evaluate plaque viscoelasticity, to facilitate an improved understanding of plaque stability, and advance clinical capability for the detection of vulnerable plaques with the highest risk of rupture in patients.

The exemplary ILSI technology, according to an exemplary embodiment of the present disclosure, can be based on an exemplary laser speckle approach. For example, laser speckle, a grainy pattern formed by the interference of laser light scattered from tissue, can be dynamically modulated by endogenous particular Brownian motion governed by the mechanical susceptibility of tissue. It has been previously demonstrated that the time scale of speckle modulations, defined by the speckle decorrelation time constant, can provide a highly sensitive metric of viscoelasticity that can be closely related with plaque composition and mechanical moduli. Given the potential impact of ILSI in measuring a key mechanical metric of plaque stability, it can be possible to utilize the exemplary ILSI systems and methods for evaluating coronary plaques in patients. The large size (e.g., approximately 1.5 mm), and limited point sampling capability of existing ILSI devices, however, can render it less than optimal for human use. Therefore, it can be possible to provide a miniaturized ILSI catheter for human use which can facilitate scanning of the entire circumference and length of the coronary artery to evaluate maps of arterial viscoelasticity distribution.

Exemplary Object 1: Provide ILSI Catheter and Console Suitable for Human Use The exemplary ILSI technology can utilize a miniaturized intracoronary catheter (e.g., <1.0 mm) to acquire speckle images from the arterial wall. The catheter can be interfaced with a high-speed console to facilitate helical scanning of the coronary artery. Speckle analysis and visualization procedures can be implemented to reconstruct cylindrical maps of arterial time constants over the circumference and length of coronary segments. Performance benchmarks including catheter size and mechanical characteristics, imaging time and spatial resolution can be optimized and verified in human cadaveric hearts. The exemplary ILSI catheter performance can be evaluated in living swine using a human to swine coronary graft model to facilitate imaging of human coronaries under physiologic conditions.

Exemplary Object 2: Indicate Safety and Feasibility of ILSI Technology in Patients Regulatory procedures involving catheter evaluation, biocompatibility testing, laser exposure evaluation and safety studies in living swine can be performed in preparation for hospital IRB and FDA applications to conduct clinical studies. ISO 10555 requirements can be followed to fabricate sterile, single-use catheters in a controlled, Class 10000 GLP clean room facility at the Wellman Center. Following regulatory approval, ILSI can be conducted in 20 patients undergoing percutaneous coronary intervention. Cylindrical maps of arterial mechanical properties measured by ILSI can be registered and correlated with microstructural information obtained using intracoronary OFDI.

The exemplary ILSI can provide a tool to significantly advance current scientific understanding of vulnerable plaque instability in patients. It can also provide a powerful diagnostic role within a comprehensive clinical paradigm of AMI management to facilitate an identification of plaques with the highest risk of rupture for treatment prior to adverse events in patients.

Exemplary Strategy

Exemplary Vulnerable plaque detection: AMI, frequently caused by the rupture of vulnerable coronary plaque, claims more lives worldwide than cancer, accidents and AIDS combined. Autopsy studies reveal a type of plaque, the thin cap fiutopsy stud ("TCFA") implicated at the site of culprit thrombi in >70% of patients who have succumbed to AMI. (see, e.g., References 1 and 2). TCFA's can be most frequently found within the proximal approximately 5 cm of the major coronary arteries and can be histologically hallmarked by the presence of a thin fibrous cap (e.g., <65 µm), rich in macrophages, overlying a large necrotic lipid pool. (See, e.g., References 1-5). A number of technologies such as optical coherence tomography ("OCT"), virtual histology intravascular ultrasound ("VH-IVUS"), computed tomography ("CT"), angioscopy and near infrared spectroscopy ("NIRS") have been investigated in patients to evaluate key morphologic features such as fibrous cap thickness, plaque burden, calcific nodules and lipid content. (See, e.g., References 6-26) An important challenge, however, in identifying plaques with the highest risk of rupture in patients can be that plaques with similar vulnerable morphologic features do not all possess an equal likelihood of rupture. For example, in 70% of patients dying from AMI, multiple TCFA's can be found without rupture at sites remote from the culprit plaque and in non-culprit arteries, (see, e.g., Reference 2) and can appear with similar frequency in stable patients with asymptomatic coronary artery disease ("CAD"). (See, e.g., References 2, 27-29). Moreover, in approximately 20% of cases, plaque rupture can be observed in necrotic core ("NC") lesions with thicker fibrous caps (e.g., >100 µm), intra-plaque hemorrhage or calcific nodules. (See, e.g., References 2, 28, 31). These findings call into question the current detection paradigm that relies entirely on morphologic criteria, and highlights, the need to augment morphologic findings with important surrogate metrics, such as mechanical metrics, in order to accurately evaluate the risk of plaque rupture. (See, e.g., References 1 and 2).

Knowledge of mechanical metrics can be important to accurately determine the risk of plaque rupture. The atheroma can be viscoelastic in nature, exhibiting both liquid (e.g., viscous) and solid (e.g., elastic) behavior. During the pathogenesis of atherosclerosis, from lesion initiation to rupture, the viscoelastic properties of the plaque can be altered by a complex milieu of hemodynamic and biochemical processes. The ultimate event of plaque rupture can be a biomechanical failure that can occur when a plaque with severely compromised mechanical properties can be unable to withstand loads exerted on it. (see, e.g., References 32-41). Therefore, in order to identify plaques with the highest risk of rupture, it can be important to complement morphologic information provided by current technologies with knowledge of viscoelastic properties.

Current knowledge of plaque viscoelasticity however can be limited as it can largely be derived from ex vivo mechanical testing of cadaveric and animal arteries. These measurements can provide only a retrospective snapshot of bulk properties, limiting the understanding of how mechanical metrics can be altered during the plaque remodeling in vivo. Therefore, important estimates of plaque viscoelastic properties predisposed to the final event of rupture can be currently unknown. Crucial questions remain on how current knowledge of plaque mechanical stability translates in vivo, restricting the opportunity for accurate detection of high-risk vulnerable plaques in patients. Together, these factors can highlight a important barrier in the field: the ability to detect plaques with the highest risk of rupture can be significantly hindered by the absence of tools for the mechanical characterization of coronary plaques in patients.

An exemplary embodiment of an ILSI system and method according to the present disclosure can be provided for a clinical use that can be used to evaluate the viscoelastic characteristics of coronary plaques in patients. The exemplary ILSI systems and methods can measures plaque viscoelasticity by utilizing an exemplary laser speckle approach developed in a laboratory, which can interrogate the ensemble Brownian motion dynamics of light scattering particles intimately linked with the micromechanical behavior of the atheroma. The exemplary ILSI systems and methods can measure an index of viscoelasticity defined by the speckle decorrelation time constant ($\tau$) that can be highly sensitive to minute alterations in the viscoelastic properties of the atheroma (e.g., Section C). (See, e.g., References 42-46). The exemplary ILSI systems and methods can provide an improved understanding of human CAD and advance clinical capability to detect plaques with the highest risk of rupture in patients as discussed below.

Exemplary Understanding of CAD by ILSI: The exemplary ILSI technology can provide important mechanical metrics implicated in plaque instability in animals and patients. The miniaturized ILSI catheter (e.g., <1 mm) can facilitate evaluation of small coronary vessels and flow limiting lesions. The reconstruction of 2D maps (e.g., FIG. 1) can provide knowledge of viscoelasticity distributions over the circumference and length of the coronary vessel. The capability to evaluate depth-resolved 3D information at high spatial resolutions (e.g., approximately 100 µm) can be provided to facilitate an important understanding of the mechanical properties of the lipid pool and fibrous cap in NC plaques of highest clinical relevance. The superior sensitivity of the exemplary ILSI systems and methods described herein to minute alterations in viscoelasticity can be utilized for plaque remodeling during the natural history of coronary atherosclerosis leading to rupture. It can be known that in early lesions, inflammatory processes can influence the accumulation of low viscosity lipid. (See, e.g., References 47 and 48). In advanced plaques, apoptosis of foam cells and intraplaque hemorrhage can result in large necrotic lipid pools of further reduced viscosity. (See, e.g., References 49 and 50). Furthermore, lipid pool viscosity can also be influenced by cholesterol, phospholipids and triglyceride content. (See, e.g., Reference 50). ILSI measurements of lipid pool viscosity can provide insights on the load bearing properties of the atheroma, and can offer a likely explanation for why TCFAs do not all possess the equal likelihood of rupture. The mechanical properties and morphology of the fibrous cap can be radically altered by a net reduction in collagen content that can occur due to an imbalance in collagen proteolysis by matrix metalloproteinases ("MMP") and synthesis due to apoptosis of smooth muscle cells. (See, e.g., References 51-53). ILSI can provide knowledge of important estimates of fibrous cap viscoelasticity related with the final event of plaque rupture.

Finite element ("FE") studies of coronary cross-sections derived from histology sections, or IVUS and OCT images can show that peak stresses associated with plaque rupture can be dependent on the geometry and viscoelastic properties of the fibrous cap and lipid pool, and plaque rupture can become imminent when the peak stress in the plaque surpasses an important amplitude. (See, e.g., References 32-41, 54 and 55). Precise measurement of peak stress amplitudes predisposed to rupture needs accurate estimates of the viscoelastic properties of plaque components in situ. ILSI can help address this challenge; combining FEA approaches with ILSI maps of viscoelasticity distributions can provide a powerful new method for accurate evaluation of peak stress in situ.

The spontaneous rupture of coronary plaques leading to AMI can be unique in human CAD. Because there can be no realistic animal models available that can mimic this event under physiologic conditions, many key hypotheses that relate mechanical metrics with the final event of plaque rupture can only be best studied in human patients. Exemplary embodiments of the present disclosure address this challenge by providing translating ILSI for use in patients.

The exemplary ILSI systems and methods can be used for the detection of vulnerable plaques in patients at risk for AMI. Recent clinical studies show that 10% of patients undergoing PCI and statin therapy following the first acute event develop a second adverse event due to plaque rupture within 3 years. (See, e.g., References 56 and 57). The exemplary ILSI systems and methods can be used by interventional cardiologists to detect potential plaques such that a second major adverse event can be prevented. Thus, over 100,000 people annually in the USA alone can benefit by ILSI screening.

In order to reduce mortality due to AMI in the general population, new preventative paradigms for AMI management can be realized. These exemplary paradigms can use a comprehensive screening strategy to identify at risk patients and detect high-risk vulnerable plaques in these patients such that they can be treated prior to AMI. Non-invasive imaging of the coronary tree using computed tomography ("CT") and magnetic resonance imaging ("MM") approaches can be important in identifying asymptomatic patients at highest risk of AMI. (See, e.g., References 58 and 59). These approaches, however, lack sufficient sensitivity and resolution to evaluate mechanical and morphological characteristics to detect vulnerable coronary plaques. A second level of intracoronary screening using ILSI can be used to evaluate plaques with compromised mechanical stability likely to cause AMI in asymptomatic patients at risk.

Furthermore, the exemplary ILSI systems and methods elegantly can be used for an integration with other intracoronary technologies such as optical coherence tomography ("OCT") and optical frequency domain imaging ("OFDI") or intravascular ultrasound ("IVUS"), (see, e.g., References 60-62) (see, e.g., Reference 57) to render powerful approaches that can place mechanical findings within a morphologic context for a composite evaluation of plaque stability.

Further, treatments for stabilization, including low force self-expanding and bio-absorbable stents, vascular tissue implants, stem cell and photodynamic therapy, can be developed by a number of companies and groups. These therapeutic interventions can utilize diagnostic tools for the accurate diagnosis or determination of rupture-prone coronary plaques prior to treatment.

Brief Description of Exemplary ILSI Systems and Methods

It can be important to provide a tool to evaluate the viscoelastic properties of coronary plaques in patients. IVUS-based elastography has been developed to measure plaque strains in response to intra-luminal stress. However, evaluation of plaque viscoelastic properties can be intractable using this approach. (See, e.g., References 63 and 64). While recent studies have utilized inverse methods and deformable curves to reconstruct Young's moduli from elastography strain maps, the approximation of linear elastic behavior by these methods can restrict accurate evaluation of the load bearing properties of viscoelastic tissue components and low viscosity lipid pools. It can be possible to apply elastography approaches to OCT to provide higher resolution for strain estimation relative to IVUS. Loss of OCT signal in lipid rich tissue, however, can preclude strain assessment in NC plaques, thus significantly limiting clinical utility. 65-67 There are no known techniques that can evaluate the viscoelastic properties of coronary plaques in patients.

The following benefits can be provided by the exemplary ILSI systems and methods: 1) a measurement of plaque viscoelasticity that cannot be accomplished by any other previously known technique. 2) facilitation of a clinical grade ILSI device for use in patients. 3) The use of the exemplary ILSI device in human translation.

The exemplary ILSI device can facilitate a comprehensive screening of the arterial circumference over long coronary segments to evaluate plaque viscoelasticity maps at spatial resolution approximately 100 µm. It can be possible to provide an exemplary miniaturized ILSI catheter (e.g., 2.4-3.0 F) including one or more low cross-talk fiber bundles with sufficient motion tolerance to evaluate the coronary wall in vivo. To achieve capability for helical scanning, it can be possible to provide an exemplary optical rotary junction and motor drive assembly that can couple and receive light from multiples cores of the fiber bundle while simultaneously rotating and translating the catheter during imaging. In order to facilitate a collection of arterial speckle decorrelation information, a programmable stepper motor can be utilized to encode and transmit torque to the catheter in discrete increments, which can facilitate sufficient sampling of the coronary circumference at a rotational rate of approximately 1 Hz. The exemplary ILSI device can utilize a high-speed complementary metal oxide semiconductor ("CMOS") camera (e.g., 2 kHz frame rate) to obtain τ measurements over very short time scales (e.g., 25 ms) over which the influence of low frequency arterial deformations induced by cardiac (approximately 1 Hz) or respiratory (approximately 0.2 Hz) motion can be largely mitigated. Using this exemplary approach, ILSI measurements can be accomplished without the need for electrocardiogram ("EKG") gating in vivo.

The exemplary ILSI device does not need apriori approximations on plaque geometry or loading conditions to measure viscoelasticity, therefore, automated ILSI analysis can be rapidly accomplished rendering ease of use in the catheterization suite. Cylindrical 2D maps of plaque viscoelasticity can be provided from ILSI data to measure the influence of spatial heterogeneities. Exemplary methods can be provided that can utilize a spatio-temporal speckle analysis in conjunction with Monte Carlo models of light propagation to provide a new technique for depth-resolved ILSI in NC plaques in vivo. By combining circumferential scanning with depth-resolved ILSI, the complete 3D determination of plaque viscoelasticity distributions can be achieved at selected sites to furnish information on the load bearing properties of the lipid-pool and fibrous cap. Because ILSI measurements can be based on phase shifts of multiply scattered light caused by minute scatterer displacements, this exemplary technique can be highly sensitive to small changes in plaque viscoelastic properties, and can render high precision for the evaluation of lipid pools.

It can also be possible to provide a clinical translation of the ILSI technology according to an exemplary embodiment of the present disclosure.

Exemplary Approach

Exemplary Overview of Approach: ILSI can be based on an exemplary laser speckle approach that has been developed to evaluate the viscoelastic properties of tissue. (See, e.g., References 42-45, 65 and 68-70). For example, laser speckle (e.g., FIG. 2), (see, e.g., Reference 71) a grainy intensity pattern that occurs by the interference of coherent light scattered from tissue, can be modulated by the Brownian motions of endogenous particles within tissue. In can be well known that the extent of particular Brownian motion can be intimately related with the micromechanical susceptibility of the medium, and particles can exhibit larger motions when their local environment can be less viscous.

Figure 3:
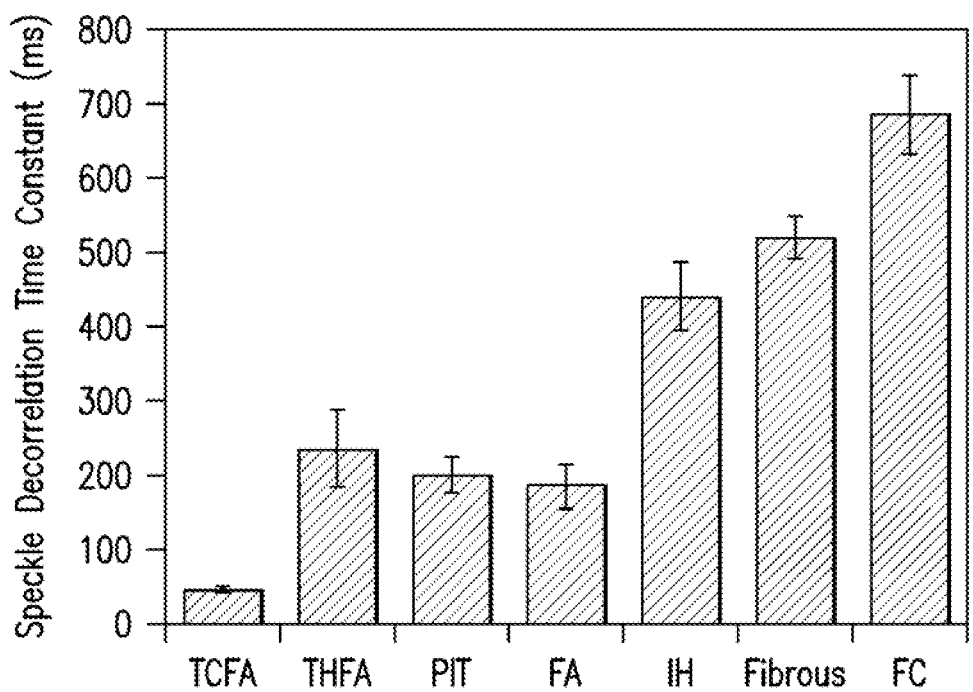
FIG. 3 is an exemplary graph illustrating g2(t) curves according to an exemplary embodiment of the present disclosure.

(See, e.g., References 72-74). Consequently, in an atheroma due to the low viscosity of lipid, scatterers can exhibit rapid Brownian motions, eliciting rapid speckle intensity fluctuations compared to stiffer fibrous regions. The extent of speckle fluctuations can be quantified from the speckle decorrelation curve, g2(t), which can be obtained by calculating the normalized cross-correlation coefficient over a time series of laser speckle patterns (e.g., FIG. 3). The rate of speckle modulation given by the speckle decorrelation time constant, $\tau$, can provide a highly precise index of plaque viscoelasticity that can be closely related to plaque composition and viscoelastic moduli. (See, e.g., References 42, 46)

Figure 4:
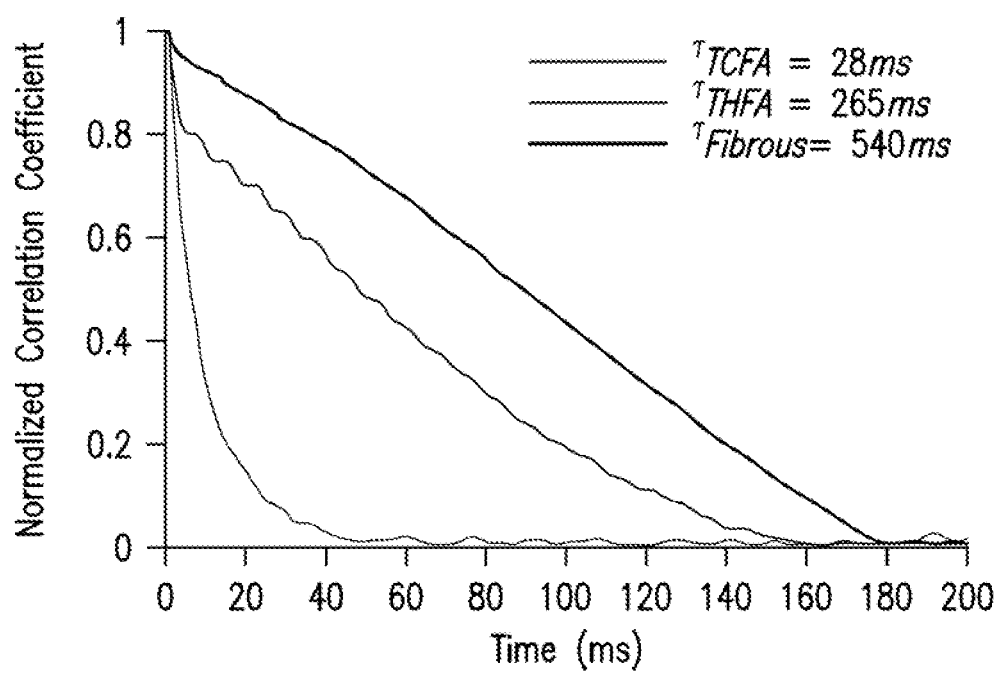
FIG. 4 is an exemplary graph illustrating mean τ for different plaque groups according to an exemplary embodiment of the present disclosure.

(i) Plaque Characterization: Studies have been conducted to demonstrate the capability of LSI for evaluating the index of viscoelasticity, $\tau$, in cadaveric plaques.[42] Time-varying speckle patterns were obtained from approximately 100 arterial samples using a Helium Neon source (e.g., 632 nm) and a CMOS camera to evaluate g2(t). The time constant, $\tau$ was measured by exponential fitting of g2(t) for each plaque (e.g., FIG. 4). Exemplary results show that $\tau$ can provide highly sensitive discrimination of plaque type (e.g., $p<0.001$). In particular, LSI can demonstrate exquisite sensitivity (e.g., 100%) and specificity (e.g., 92%) for discriminating the viscoelastic properties of TCFAs (e.g., $\tau=45$ ms) due to rapid particular Brownian motion within low viscosity lipid pool (e.g., $p<0.0001$). Similarly, stiffer fibrous and fibrocalcific lesions can elicit significantly larger $\tau$ values (e.g., $p<0.001$).

(ii) Exemplary Relationship between $\tau$ and plaque composition: Since viscoelastic properties can be highly dependent on composition, $\tau$ showed high correlation with plaque collagen content (e.g., R=0.73; $p<0.0001$) and consequently with cap thickness (e.g., R=0.87; $p<0.001$). (See, e.g., Reference 42). Given the low viscosity of lipid, a strong negative correlation (e.g., R=−0.81; $p<0.0001$) between $\tau$ and lipid content was observed. These exemplary results demonstrate that LSI can measure an index of viscoelasticity, $\tau$, closely related with compositional metrics associated with plaque stability.

(iii) $\tau$ and viscoelastic modulus: In order to demonstrate the potential of LSI in estimating the viscoelastic properties of samples, the relationship has been evaluated between the modulus of viscoelasticity, G, measured by mechanical testing and LSI time constant, $\tau$ using (a) homogeneous gels, and (b) atherosclerotic plaques. In the present disclosure, the term, 'bulk' modulus, G, can be used to define the overall modulus which integrates over the sample volume.

Figure 5:
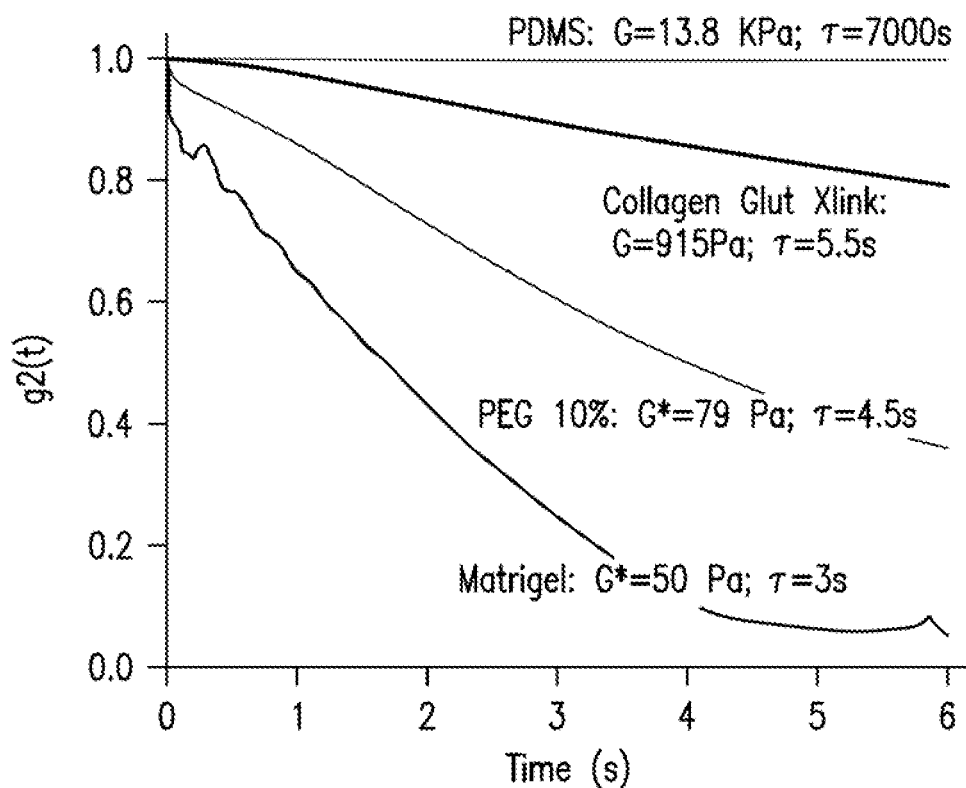
FIG. 5 is an exemplary graph illustrating τ values according to an exemplary embodiment of the present disclosure.

(a) Homogenous gels: LSI was performed on collagen, PDMS, PEG and Matrigel substrates of varying concentrations. Corresponding mechanical testing measurements were performed on all samples using a strain-controlled rheometer (e.g., ARG2, TA Instruments Inc., MA) to measure modulus G. The samples were loaded between the parallel plates of the rheometer and an oscillatory strain (e.g., 1%) was applied over a frequency range of about 0.1-5 Hz. High correlation between $\tau$ and G (e.g., R=0.92, $p<0.001$) was observed over the linear frequency range in all samples. These results confirm that $\tau$ can provide a highly accurate estimate of sample viscoelastic properties (e.g., FIG. 5). To evaluate the measurement sensitivity of LSI, time lapse measurements of $\tau$ were compared with G values measured during slow curing of PDMS gels over 24 hours. High correspondence between $\tau$ and G was observed (e.g., R=0.95, $p<0.01$), confirming the high sensitivity of the LSI approach to changes in viscoelastic properties of the sample.[75]

(b) Arterial plaque studies: LSI was conducted by averaging $\tau$ values over 3 mm disks of aortic sites, histologically confirmed as calcific, fibrous and lipid-rich. Mechanical testing was performed as above, which revealed distinct G values between plaque groups: $2.27\times10^5$ Pa (calcific), $3.65\times10^3$ Pa (fibrous) and $2.23\times10^3$ Pa (NCFA). Analysis of variance ("ANOVA") tests showed statistically significant differences in G for the plaque types (e.g., $p<0.001$). These values also correspond with previously published reports. (See, e.g., Reference 76). For all plaques, $\tau$ correlated well with G (R=0.97, $p<0.001$), establishing the close relationship between $\tau$ and plaques viscoelastic properties, and suggesting that $\tau$ can provide a key metric related to the mechanical strength of the plaque.

Exemplary Influence of Spatial Heterogeneities (i) Modeling Studies: To evaluate the influence of structural parameters on the bulk modulus, a plaque was modeled as a multilayered cylinder of thickness, L and viscoelastic modulus, G. For the purpose of this model, it can be assumed that viscoelastic modulus, G≈G' (elastic modulus), supported by previous reports. (See, e.g., References 76 and 77). Given its clinical significance, it can be possible to consider a NC plaque with a fibrous cap and NC of thicknesses L1 and L2, and moduli G1 and G2, loaded between the parallel plates of a rheometer. The twisting moment M applied by the rheometer can be determined by the distribution of shear stresses integrated across the plaque. (See, e.g., Reference 50). By equating M with the polar moment of inertia and the angular displacement of the sample, it can be possible to deduce the expression, for example:

$$G = \frac{LG_1G_2}{L_1G_2 + L_2G_1} \quad (1)$$

Eqn. (1) shows that the overall bulk modulus of the plaque can be related to the thickness and viscoelastic modulus of each layer. Eqn. (2) below can be applied to evaluate the relationship between the bulk modulus G and fibrous cap thickness in a NC plaque, using previously reported values (see, e.g., Reference 76) of G1=496 kPa, and G2=222 kPa, for fibrous and lipid rich tissue and can evaluate the influence of varying fibrous cap thickness (e.g., 0-500 µm) on bulk G (e.g., FIG. 3). This exemplary model can be also extended to include multiple layers of varying depth-dependent viscoelasticity by using the following exemplary generalized equation:

$$\frac{L}{G} = \sum_n \frac{L_i}{G_i} \quad (2)$$

Figure 6:
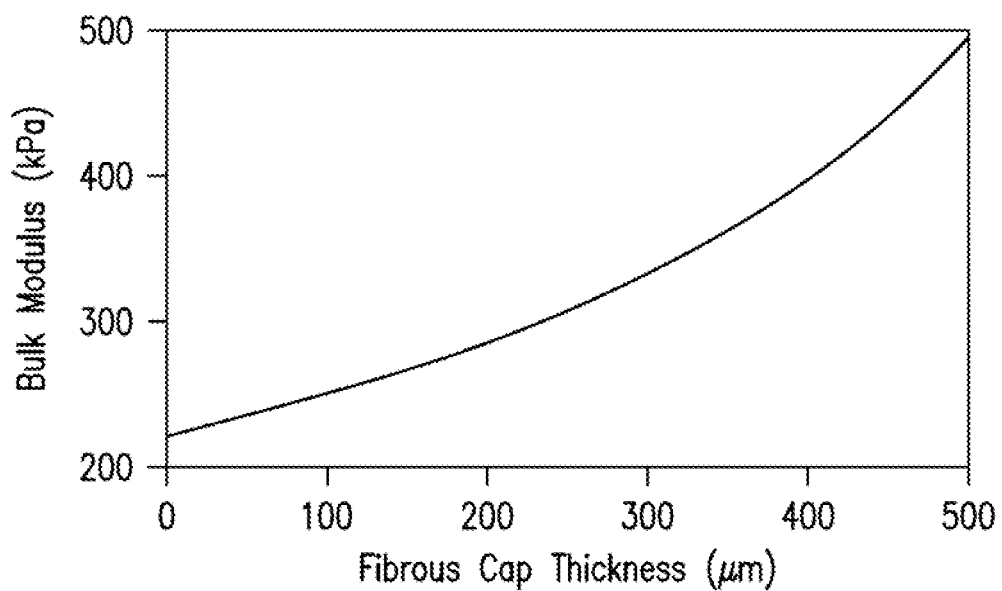
FIG. 6 is an exemplary graph illustrating an estimation of the overall bulk modulus of a necrotic core fibroatheroma as a function of fibrous cap thickness according to an exemplary embodiment of the present disclosure.

These studies indicate that the fibrous cap thickness can greatly influences the overall bulk viscoelasticity of the plaque (e.g., FIG. 6), and also indicate that the measurement of bulk viscoelastic properties can provide a key metric closely related with plaque stability.

(ii) Lateral scanning in LSI: To evaluate the capability of LSI in measuring heterogeneities, laser speckle images of plaques were obtained by scanning the He Ne spot at 300 µm increments and the spatial distribution of $\tau$ was measured. FIG. 7 demonstrates the lateral variation of $\tau$ as a function of beam location. As the beam was scanned across each lesion, τ varied significantly depending on tissue type: τ was low (e.g., 20-50 ms) in the low viscosity NC regions (e.g., FIG. 7A) and higher in the stiffer calcific (e.g., approximately 2200 ms in FIG. 7B) and fibrous (e.g., approximately 800 ms in FIG. 7C) regions. Similarly 2D maps of the spatial τ distributions were obtained by beam scanning over the region of interest ("ROI") (e.g., FIG. 1), to facilitate a detection of heterogeneities such as calcific nodules and lipid pools to facilitate comprehensive coronary screening.

(iii) Depth-dependent heterogeneities: Due to the diffusive properties of light propagation in tissue, photons returning from deeper regions have a higher probability of remittance farther away from the illumination location.[78-81] In such publications, τ was computed over the entire speckle pattern. Therefore, Brownian motion was integrated over all optical depths and information about tissue heterogeneity was lost. By combining LSI with an exemplary Monte Carlo analysis of light propagation, depth information can be obtained. (See, e.g., Reference 43). In this study, the capability to measure fibrous cap thickness was demonstrated by analyzing variation in τ as a function of radial distance, ρ, from the illumination location in each speckle image. Fibrous cap thickness estimates obtained using this method, were highly correlated with Histologic measurements (e.g., FIG. 8). These findings indicate the potential of obtaining depth information using LSI, which can be further explored for in vivo intracoronary use in the current proposal.

Exemplary Intracoronary ILSI

Figure 9:
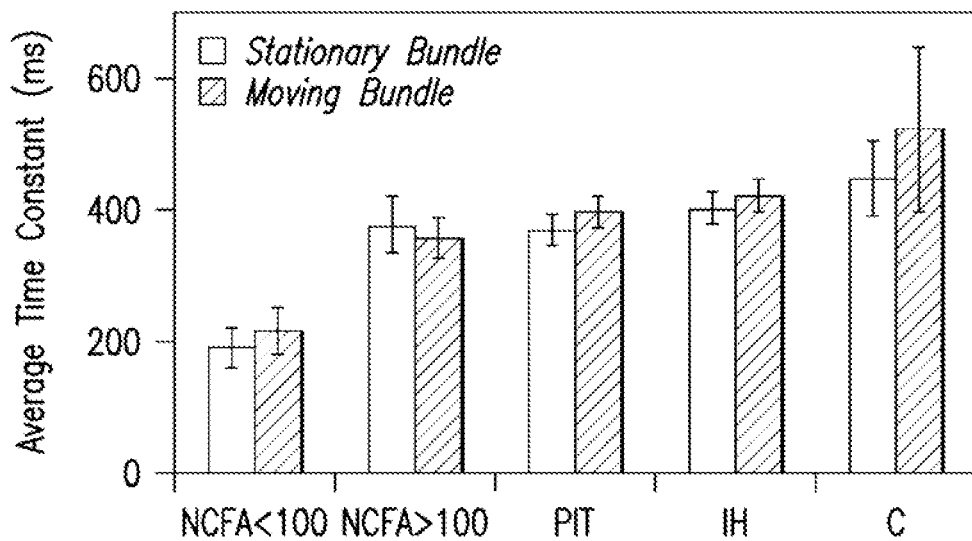
FIG. 9 is an exemplary graph illustrating average plaque τ measured via an exemplary leached fiber bundle according to an exemplary embodiment of the present disclosure.

Exemplary ILSI Catheter Construction and Testing (i) Fiber bundle selection: Optical fiber bundles form an important part of the exemplary ILSI catheter to transmit speckle patterns. One challenge can be that speckle modulation can be influenced by inter-fiber light leakage (e.g., cross-talk) which can likely be exacerbated during motion. A study[44] was performed to investigate the influence of motion on the diagnostic efficacy of fiber bundle based LSI in 75 arterial plaques, while cyclically modulating the flexible length of the bundle to mimic cardiac motion and tortuosity. A variety of fiber bundles were tested. The bundle with the highest motion tolerance was selected as having the (a) highest correlation, (b) lowest error, and (c) minimal statistically significant difference in measuring plaque ti values under stationary and moving conditions. Low cross-talk leached fiber bundles provided the best motion stability (e.g., SCHOTT, Inc.), likely due to the manufacturing (e.g., leaching) process which can result in large separations between fiber cores and reduced cross-talk. (See, e.g., Reference 44). In particular, the leached bundle with the smallest partial core size of approximately 0.36 (e.g., core area÷fiber area) provided the best results for the above three criteria (e.g., FIG. 9). Based on these findings, miniaturized leached fiber bundles with low partial core sizes (e.g., <0.4) can be incorporated in the clinical-grade ILSI catheter proposed in this grant.

Figure 10:
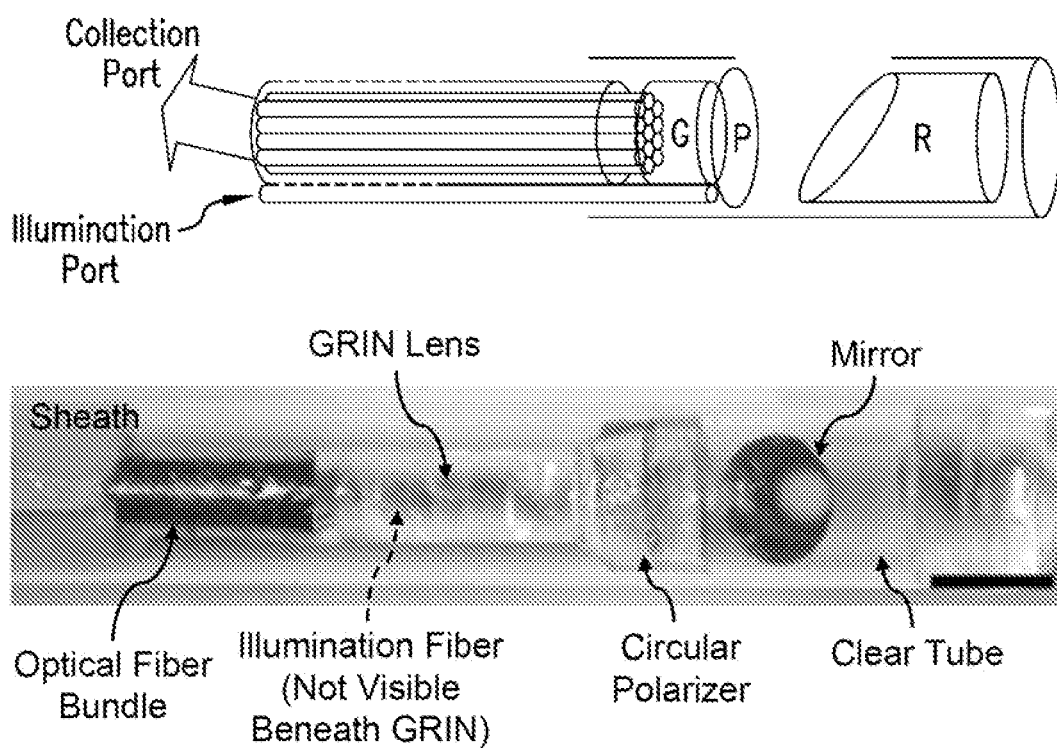
FIG. 10 is an exemplary schematic of an exemplary ILSO catheter according to an exemplary embodiment of the present disclosure.
Figure 11:
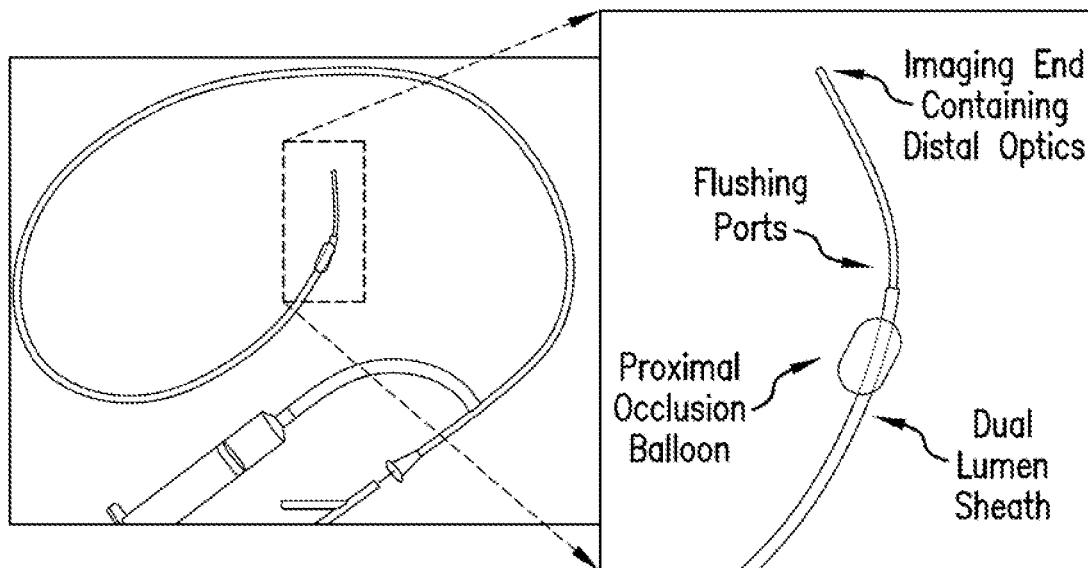
FIG. 11 is an exemplary image of an exemplary LSI catheter sheath according to an exemplary embodiment of the present disclosure.
Figure 12:
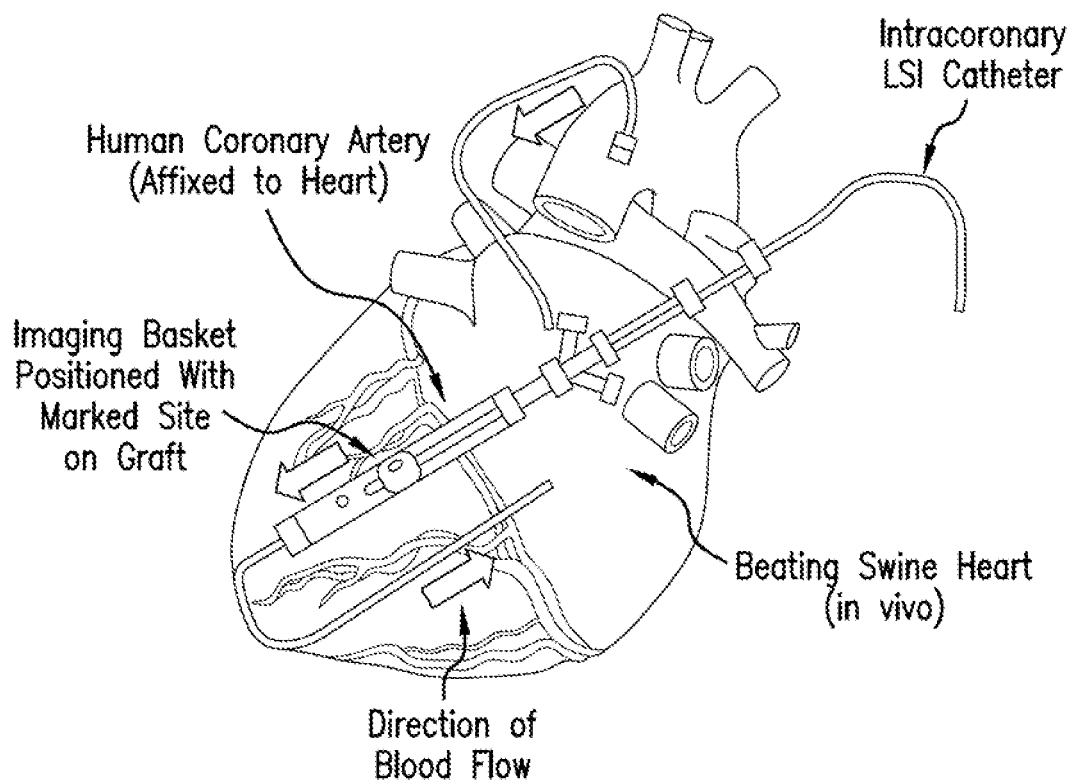
FIG. 12 is an exemplary schematic of an exemplary ILSO procedure in a swine xenograft model according to an exemplary embodiment of the present disclosure.

(ii) Exemplary ILSI catheter: An exemplary ILSI catheter (e.g., dia=1.57 mm) can be provided that can include an inner optical core and custom-designed external sheath.[46] The optical core (e.g., FIG. 10) can consist of an optical fiber to illuminate the arterial wall and a leached optical fiber bundle to collect arterial speckle patterns. The exemplary design of the catheter distal optics for light delivery and speckle image transmission was optimized using ZEMAX (e.g., ZEMAX Development Corporation) for an approximate 500 μm field of view ("FOV"). The optical elements (e.g., GRIN lens, polarizer and mirror) were assembled at the distal face of the fiber bundle within a clear tube (e.g., FIG. 10) and the proximal bundle face was imaged via an objective lens and CMOS camera. To house the optical core, it can be possible to use a double-lumen catheter sheath (e.g., FIG. 11). Since blood presents an impediment to intracoronary optical approaches, the sheath can include an occlusion balloon which can facilitate the comparison of the effectiveness of proximal balloon occlusion ("PBO") with flushing techniques during the exemplary ILSI procedure. The sheath can also have radio-opaque marker at the distal end for fluoroscopic guidance and a rapid exchange guidewire port. The catheter performance in evaluating cadaveric plaques was compared with free-space LSI: high correlation (e.g., R=0.79, p<0.01) was attained between ILSI and free space τ measurements. For in vivo testing, the catheter was interfaced with a portable console for intravascular evaluation in the aorta of a living rabbit. Distinct differences in arterial τ measured at normal aortic and stented sites confirmed in vivo feasibility. (See e.g., Reference 46).

Exemplary Feasibility of Intracoronary LSI in Living Swine

The feasibility of ILSI has been reviewed for coronary evaluation in vivo, and to determine the influence of cardiac motion, and blood displacement approaches.

(i) Human to swine coronary xenograft model: Exemplary choice of animal model can be motivated by two key requirements: (1) feasibility of ILSI can be best tested on human coronary disease, and (2) testing must be performed under conditions that mimic human cardiac physiology. This model has been previously described to test intracoronary optical technologies. (See, e.g., References 82 and 83). Cadaveric hearts (e.g., N=3) from patients who died of AMI were obtained (e.g., NDRI). LAD and RCA coronaries (e.g., proximal 5 cm) were prosecuted and side branches ligated. Coronary grafts were marked with India ink on the adventitial side to identify discrete sites for co-registration with Histopathology. In anesthetized swine (e.g., N=3), the chest was opened, the grafts were sutured on the beating swine heart, and blood flow was redirected through the graft via an aorto-atrial conduit. A total of 24 discrete sites in 6 grafts were evaluated using ILSI in 3 living swine.

(ii) Exemplary ILSI procedure: A portable console was developed, which incorporated a Helium-Neon source (e.g., 632 nm, 30 mW) and a CMOS camera to capture speckle images at frame rate approximately 1 kHz (e.g., 512×512 pixels). The ILSI catheter was manually advanced under fluoroscopic guidance over a guide wire via the left carotid and to each discrete lesion by co-registering the illumination spot with the visible India ink mark on the artery. Prior to imaging, the proximal occlusion balloon was engaged while flushing with Lactated Ringers ("LR") to ensure that blood did not re-enter the FOV. To evaluate the influence of cardiac motion, acquisition of the first speckle image was triggered on the R-wave of the swine EKG signal, followed by asynchronous acquisition of subsequent frames over approximately 5 cardiac cycles. Following the exemplary ILSI procedure, the swine were sacrificed, and the grafts explanted and processed for Histopathological evaluation. Plaques (e.g., N=24) were diagnosed as lipid pool (e.g., n=3), pathological intimal thickening ("PIT") (e.g., n=7) and fibrous (e.g., n=14) plaques. (See, e.g., Reference 1). ILSI analysis was performed as detailed below.

(iii) Influence of cardiac motion: In order to achieve clinical viability in patients, the ILSI technology can facilitate rapid coronary screening while retaining adequate motion stability over the cardiac cycle. While EKG gating can be implemented to mitigate the influence of cardiac motion, this approach can add significant time to the imaging procedure. Instead, a non-gated approach can permit rapid imaging of long coronary segments facilitating the use of the ILSI device in patients. The studies below were performed to investigate the influence of cardiac motion and compare EKG-gated versus non-gated ILSI measurements.

To evaluate the EKG gating approach to conduct ILSI, the $\tau$ value for each plaque was calculated at the mid-diastole phase of the cardiac cycle (e.g., approximately 600 ms after onset of R-wave). To evaluate the non-gated approach, the $\tau$ value for each plaque was computed at a time point during the cardiac cycle that was randomly selected by software. For both cases, $\tau$ was calculated by exponential fitting of 50 ms of the initial decorrelation of the $g_2(t)$ curve. FIG. 13A shows an exemplary illustration of the average $\tau$ computed for the plaque groups using the EKG-gated and non-gated approaches, and the results of the pairwise comparisons between plaque groups are shown in FIG. 13B. Using both approaches, differences in $\tau$ between the three plaque groups were highly significant. Demonstrating that plaque viscoelasticity could be well distinguished even under conditions of cardiac motion. This can be because sufficient motion stability can be achieved by employing rapid image acquisition rates (e.g., $\geq 1$ kHz) using a high speed CMOS detector to measure laser speckle fluctuations over very short time scales. In vivo plaque time constants were about <25 ms (e.g., FIG. 13), indicating that imaging durations of about 25 ms can sufficiently enable plaque discrimination. Given the low frequency of cardiac motion (e.g., approximately 1 Hz) relative to the high rate of speckle decorrelation over short time scales, ILSI can be conducted during the cardiac cycle without the need for EKG gating. A key result can be that differences in $\tau$ measured within the same plaque group using the two exemplary approaches were not significantly different (e.g., FIG. 13A). This can demonstrate that non-gated ILSI works just as well as EKG-gated ILSI in vivo. From the results of this study, it can be possible to infer that: (a) an imaging duration <25 ms can be sufficient to measure speckle decorrelation for plaque evaluation in vivo, and (b) ILSI can be conducted in vivo without EKG-gating.

(iv) Intracoronary flushing: Similar to other intravascular optical techniques, in ILSI the presence of blood can hinder imaging. Proximal balloon occlusion ("PBO") and purging with flushing media can be two exemplary methods routinely used in conjunction with angioscopy and OCT to displace blood during the imaging procedure. (See, e.g., References 19 and 61). While PBO can routinely be employed in Japan, the risk of ST-segment elevation can limit the widespread adoption of this method in the USA. Instead, flushing with contrast agent (e.g., Visipaque) or Lactated Ringers ("LR") solution can routinely be used as a safe alternative during imaging.[84] Therefore, in order to assess feasibility of ILSI for patient use, studies were conducted in native coronaries of living swine to compare PBO and flushing approaches as detailed below.

(a) Balloon occlusion versus flushing in living swine: A 3 mm coronary stent was deployed into the native LAD of anesthetized swine, and ILSI was conducted at normal arterial sites, and within the stent, while the proximal occlusion balloon was engaged. The balloon was then disengaged, and the sites were evaluated in conjunction with a 30 cc Visipaque flush. Using both PBO and flushing approaches, differences in $\tau$ between the normal unstented and stented sites were highly significant (e.g., p<0.01), demonstrating that ILSI can be conducted using either of the two exemplary approaches to displace blood during imaging. In addition, differences inti measured within the same location with both PBO and flushing were not significantly different (e.g., FIG. 14). This can demonstrate that ILSI can be conducted in conjunction with flushing to sufficiently displace blood during imaging.

Figure 19:
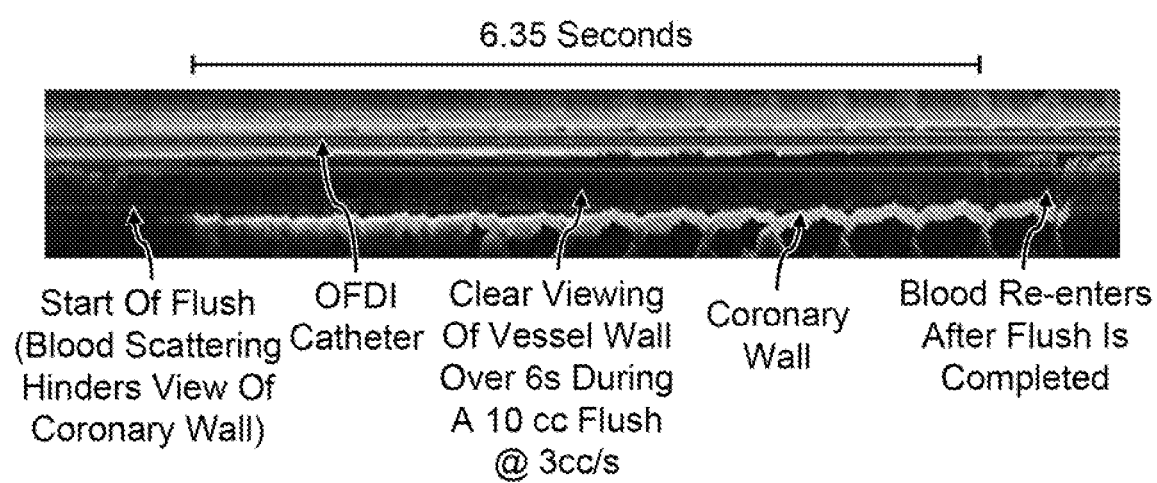
FIG. 19 is an exemplary OFDI image obtained during visipaque flushing according to an exemplary embodiment of the present disclosure.

(b) Influence of residual blood: To test the influence of residual blood cells on values, it can be possible to perform LSI on four aortic plaques within a flow cell through a 3 mm intervening layer of whole blood (e.g., HCT=30%), serially diluted using PBS. For example, $\tau$ values at HCT <0.1% were similar to those values measured without any intervening medium. Subsequently OCT imaging was performed and it was determined that at HCT >0.03%, backscattering from blood cells was clearly evident in OCT images. In clinical studies using intracoronary OCT and recent swine studies (e.g., FIG. 19) no backscattering from blood cells can be observed during flushing. Since blood does not affect LSI at a HCT <0.1% and purging in patients can apparently reduce the intracoronary HCT to <0.03%, levels of residual blood cells during flushing can be sufficiently low to conduct ILSI.

Summary of Exemplary Studies: Through certain studies, the exemplary LSI systems and methods have been developed and validated as a powerful tool to evaluate plaque viscoelastic properties. These exemplary studies have demonstrated, 1) The LSI time constant, $\tau$, can provide a metric that can intimately be linked with plaque viscoelastic properties, 2) LSI can enable highly precise differentiation of plaque type, and can have exquisite sensitivity for the evaluation of TCFAs. 3) LSI can facilitate the measurement of spatial and depth-dependent heterogeneities, 4) Intracoronary LSI can be conducted in vivo at high imaging rates in conjunction with flushing. Given the high clinical impact of measuring coronary plaque viscoelasticity and supported by the success of exemplary results in the current disclosure, it can be possible to extend LSI for intracoronary evaluation in patients. It can also be possible to provide, according to an exemplary embodiment of the present disclosure, clinical grade ILSI technology, and conduct the first in human feasibility studies as detailed below.

Exemplary Design and Methods

Overview of Exemplary design: Efforts have been directed towards developing clinical-grade ILSI catheters suitable for human use and a console to enable helical scanning over long coronary segments. Preclinical validation of the new ILSI device can be conducted to evaluate coronary plaque viscoelasticity in living swine. Further, for human clinical studies can be conducted, for example, in 20 patients to assess the safety and utility of ILSI. It can also be possible to obtain an exemplary tool that can improve an understanding of human CAD.

Exemplary Methods

The exemplary ILSI catheter described in exemplary studies above enabled the demonstration of in vivo feasibility for intracoronary evaluation. Its functionality for patient use, however, can be restricted given its large size (e.g., approximately 4.5 F/1.57 mm). In addition, the existing ILSI devices may only be permit limited point sampling of discrete sites, therefore precluding the capability for comprehensive intracoronary screening to evaluate arterial viscoelasticity distributions. Furthermore, because the exemplary device can utilize illumination over an extended beam (e.g., approximately 250 μm), and the index of viscoelasticity, τ, evaluated over the entire speckle pattern, depth-dependent information can be lost or degraded. These issues can be solved according to certain exemplary embodiments described herein below.

In order to achieve clinical utility, for example, a miniaturized exemplary ILSI catheter (e.g., approximately 2.4 F-3.0 F/0.8-1.0 mm) can be provided that can access small flow-limiting coronary arteries of patients, and can conduct rapid helical scanning of coronary segments. Speckle analysis and visualization methods can be implemented to reconstruct arterial viscoelasticity distributions. This can facilitate comprehensive circumferential screening of about 3.0-5.0 cm of the major coronary arteries with a longitudinal image spacing (e.g., pitch) of about 0.25-1.0 mm, while administering a safe total amount (e.g., <100 cc) of flushing media.

Exemplary ILSI device: Exemplary modifications of the exemplary device can be focused on certain components thereof, for example: (i) catheter, (ii) motor drive assembly for helical scanning, and (iii) console. The catheter can include an inner cable that can house the optical core. During imaging, the motor drive assembly can rotate and simultaneously pullback the inner cable within an outer stationary sheath to accomplish helical scanning (e.g., FIG. 15).

Exemplary ILSI catheter: It can be possible to provide a miniaturized leached fiber bundles (e.g., diameter approximately 250 μm, length=1 m). Utilizing a fiber size of approximately 8 μm, with a partial core area of approximately 0.4, approximately 2000 collection fibers can be incorporated to obtain a fiber bundle with sufficiently low cross-talk to transmit speckle patterns. A central light delivery fiber can be included for illumination. Micro-optical components including a focusing lens, custom polarizer and rod mirror can be optimized, tested and affixed to the distal bundle face. A variety of different lenses can be investigated, including GRIN lenses and custom-fabricated ball lenses, and optimized to provide a focused illumination spot size of approximately 20 μm and imaging FOV of approximately 500 μm. Miniaturization and fabrication of optical components can be conducted to achieve a target optical core size of approximately 300 μm. The optical core can be affixed within a driveshaft cable (e.g., Asahi Intec, CA) to convey torque from a motor to enable helical scanning. A transparent rapid-exchange sheath with a guide wire port can house the catheter cable assembly, and can be tested for optical clarity.

Figure 15:
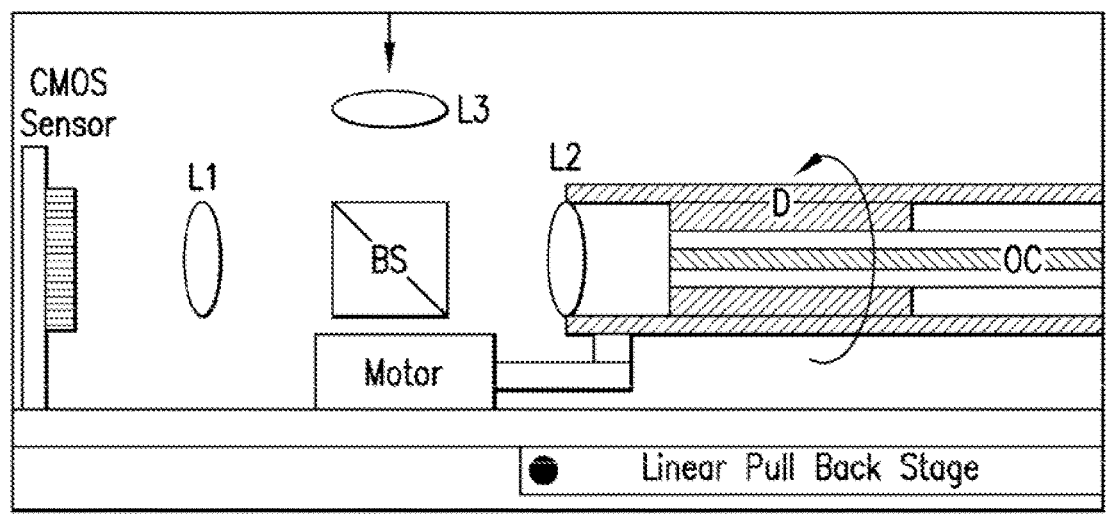
FIG. 15 is an exemplary schematic of an exemplary motor drive assembly for helical scanning according to an exemplary embodiment of the present disclosure.

(ii) Exemplary motor drive assembly can include an optical rotary junction ("ORJ") that can couple light with the rotating optical core (e.g., FIG. 15). Excellent rotational uniformity (e.g., <10% modulation) and low transmission loss (e.g., <1 dB) in can be provided with ORJs provided in the exemplary OCT/OFDI systems. (See, e.g., References 60, 61 and 85). For example, the ORJ was designed to couple with a single optical fiber within the OCT/OFDI catheter while continuously spinning at speeds of approximately 6000 rpm. The ORJ can be provided for the use with the exemplary ILSI device such that: (a) it can facilitate coupling of light with a rotating optical fiber bundle consisting of multiple optical fibers, and (b) the exemplary ILSI catheter would not spin continuously. Instead in order to permit acquisition of the speckle image time series over about 25 ms at each circumferential location (e.g., based on studies shown in FIG. 13), a stepper motor can be incorporated to rotate the optical core at discrete steps with a residence time of about 25 ms per step. The exemplary ORJ can include a collimating lens (e.g., L2) affixed at the proximal end of the optical core and a motor coupled with the driveshaft to enable rotation. A CMOS sensor (e.g., Mikrotron 1310) can be housed directly within the ORJ, and transmitted speckle patterns can be imaged via a stationary lens (e.g., L1). The rotational rate of the catheter can be 1 Hz. A linear pullback stage can facilitate a translation/pullback during imaging over speeds of about 0.25-1.0 mm/s. Rotational distortion (e.g., <10%) can be measured by comparing τ values of aortic plaques with a stationary catheter (e.g., Table. 1)

TABLE 1

Quantitative benchmarks for ILSI device in Aim 1

Figure 18A:
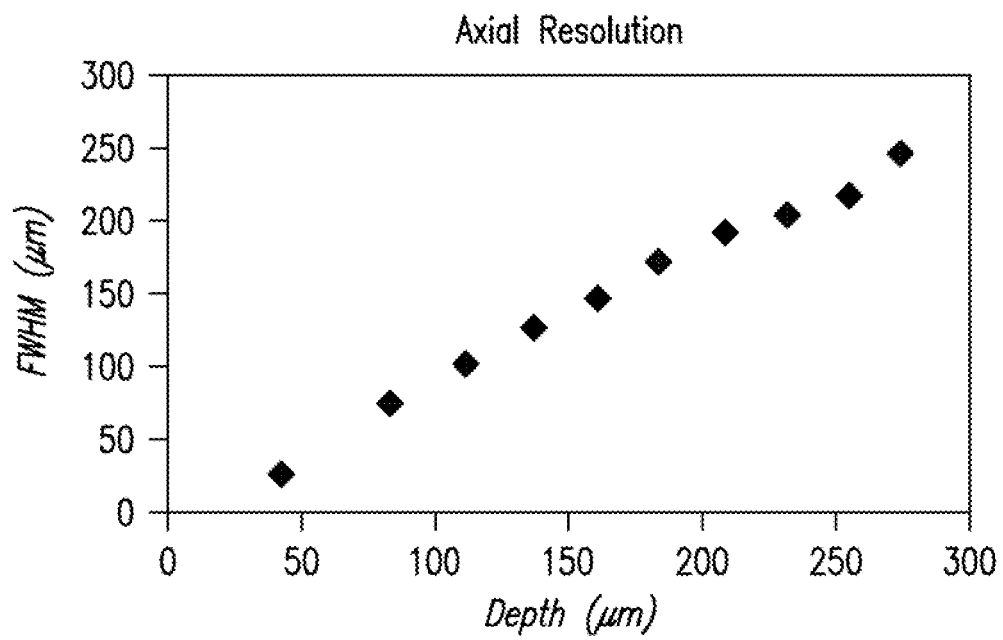
FIGS. 18A and 18B are exemplary graphs illustrating spatial resolution estimated using Monte-Carlo Ray Tracing according to an exemplary embodiment of the present disclosure.
Figure 18B:
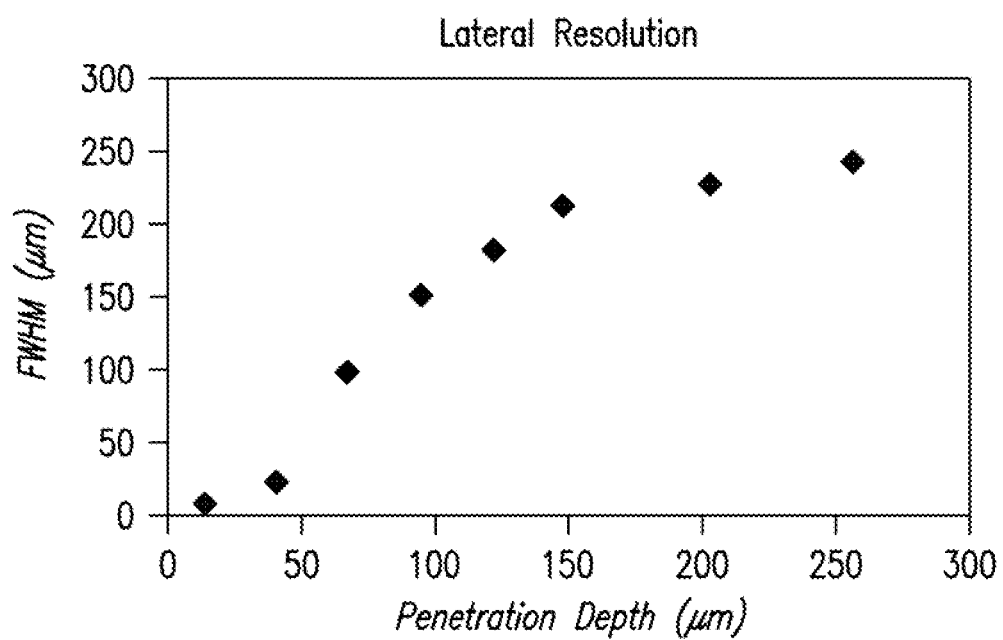

| Performance Target | Expected Value |
|---|---|
| Catheter size | 2.6-3.0 F (0.8-1.0 mm) |
| Catheter rotation rate | ~1 Hz |
| Rotational distortion | <10% |
| Lateral (circumferential) scan spacing | ~250 μm |
| Longitudinal scan pitch | 0.25-1.0 (depends on pull-back speed) |
| Dwell time per rotational increment | 25 ms |
| Field of View (FOV) | ~500 μm |
| Axial resolution | mean~100 μm (FIG. 18) |
| Lateral resolution | mena~150 μm (FIG. 18) |
| Penetration depth | ~350 μm (FIG. 19) |
| Imaging frame rate | ~2 kHz (512 × 512 pixels) |

(iii) The portable console can be modified to facilitate helical imaging and data visualization. Engineering tasks can include: a) interface to control the motor drive assembly and automated flush devices, and b) software interface design. Similar to the exemplary preliminary studies, a He Ne light source (e.g., 632 nm, 30 mW) can be used for illumination. Time-varying laser speckle images can be collected at an approximately 2 kHz frame rate (e.g., 512× 512 pixels).

Reconstruction of arterial viscoelasticity maps: To obtain sufficient spatial sampling during catheter rotation, a lateral spacing of about ≤250 μm can be utilized between rotational steps. Considering the typical coronary circumference of about 10 mm, and the catheter FOV of about 500 μm, 40 discrete steps can facilitate adequate spatial overlap for sufficient circumferential sampling at about a 1 Hz rotational rate. The longitudinal scan pitch and total imaging time can be determined by the pull-back speed (e.g., Table 1).

Exemplary 2D reconstruction: To evaluate 2D arterial viscoelasticity maps, at each site, τ can be computed over each speckle image by exponential fitting of the g2(t) curve using previously reported techniques. (See e.g., References 42 and 46). The resulting 2D array of discrete τ values can be processed using spatial filtering and bilinear image interpolation approaches to reconstruct maps corresponding to arterial viscoelasticity distributions.[86] NC plaques of high clinical relevance identified by low τ values (e.g., approximately 5-10 ms) can be selected to explore depth-resolved analysis.

Figure 16A:
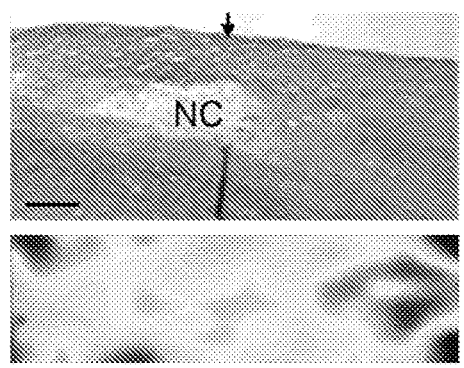
FIGS. 16A and 16B are exemplary images and color maps of τ over two NC plaques according to an exemplary embodiment of the present disclosure.
Figure 16B:
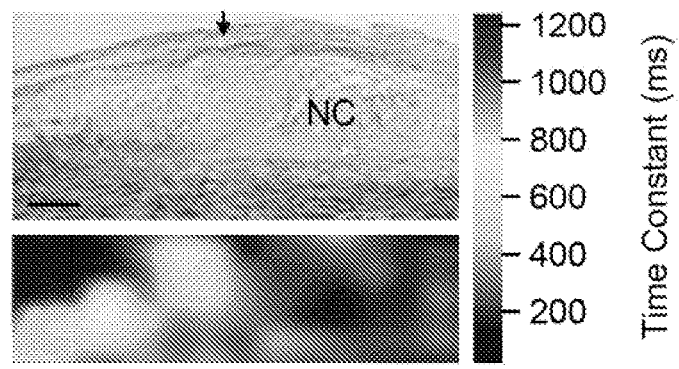
Figure 17A:
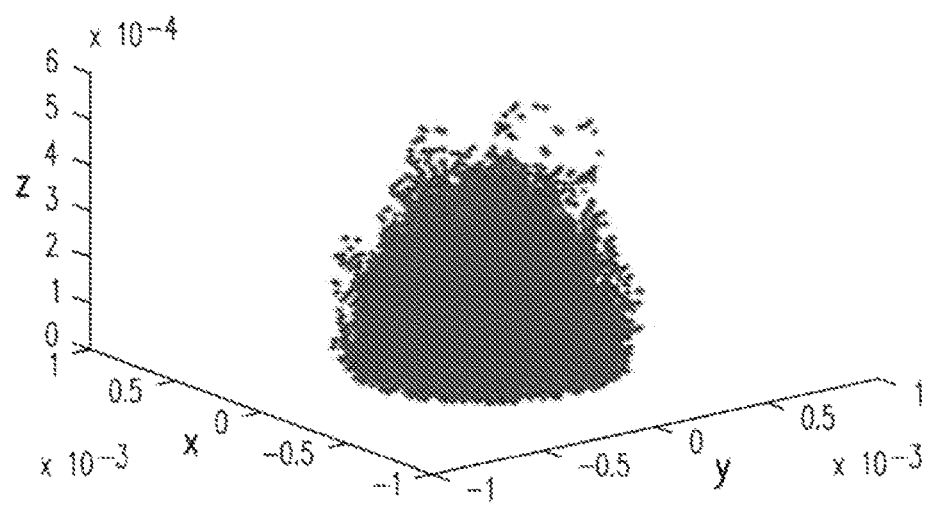
FIG. 17A is an exemplary graph illustrating a 3D distribution of mean penetration depths collected over a catheter according to an exemplary embodiment of the present disclosure.
Figure 17B:
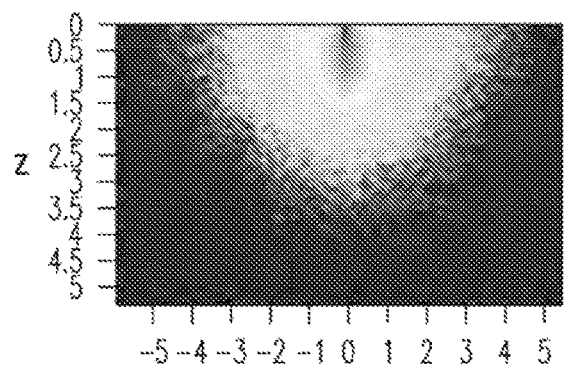
FIGS. 17B and 17C are exemplary colormaps illustrating cross-sectional distributions along x and y of FIG. 17A according to an exemplary embodiment of the present disclosure.
Figure 17C:
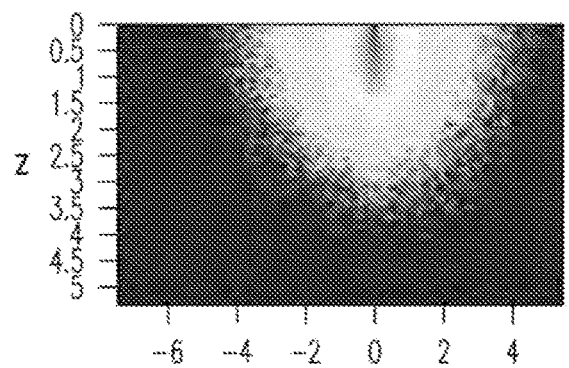

Exemplary Depth analysis: The capability of ILSI to provide 3D depth-resolved distribution of τ values in NC plaques in vivo is described below. For example, at each location (x,y) over the FOV, windowed cross-correlation can be performed over the speckle time series to obtain g2(t). To ensure sufficient ensemble averaging, g2(t) can be measured by averaging several cross-correlation functions that evolve in time over about a 25 ms imaging duration and over neighboring pixels, which can influence the measured spatial resolution for mapping. The resulting 2D distribution of τ (x,y) can be obtained (e.g., FIG. 16) by exponential fitting of g2(t) curves. Due to light transport properties, τ (x,y) farther from the beam location can be influenced by longer optical paths. Using a Monte-Carlo Ray Tracing ("MCRT") algorithm, a look up table of the 3D distribution of mean penetration depths (z) over the FOV remittance plane can be created (e.g., FIG. 17), and the corresponding depths for each τ (x,y) can be determined to provide the depth-resolved distribution of τ. The process can be repeated at each circumferential beam location to reconstruct the full 3D viscoelasticity distribution of NC plaques.

Estimated Resolution: Axial resolution can be estimated by the full width-half maximum ("FWHM") of the penetration depth distribution and the lateral resolution can be determined from the FWHM of the radial scattering PDF. Estimated values using MCRT can be plotted (e.g., FIG. 18). Spatial resolution can degrade with depth (e.g., Table 1). However, over superficial depths, the estimated spatial resolution about <100 µm can be sufficient to evaluate thin caps that can be most clinically relevant. At deeper depths (about >100 µm), resolution approximately about 100-200 µm can be sufficient to evaluate large necrotic cores of highest significance. Exemplary methods described herein can be tested on human arteries and phantoms of spatial and depth-varying properties. Axial resolution can be measured by scanning a sample of known G within scattering media using a motorized stage. Lateral resolution can be verified using a patterned PDMS resolution target.[87-89] Utilizing exemplary beam scanning in conjunction with depth-resolved LSI can provide an important understanding of the viscoelastic properties of the fibrous cap and NC layers to estimate the load bearing capabilities of clinically significant NC plaques.

ILSI Testing and validation in swine: The human to swine coronary xenograft model (e.g., preliminary studies) can be used to validate the ILSI device for coronary screening. Human coronary grafts (e.g., 2 per heart×10 hearts) can be grafted in anaesthetized swine (e.g., N=10) for ILSI validation. The distal start and end of scan locations can be marked by India ink corresponding with the visible ILSI beam for co-registration with Histology. Scanning can be performed over an approximately 5 cm pull-back in conjunction with a Visipaque flush. Following ILSI, the grafts can be evaluated using intracoronary OFDI in vivo. Histology sections can be obtained at 2 mm increments and co-registered with the corresponding ILSI cross-section. For example, a total of 500 ILSI-OFDI-Histology correlated cross-sections can be analyzed (e.g., 25 sections/artery×2 arteries×10 hearts). Plaque type can be diagnosed at approximately 250 µm spacing using both Histology and OFDI as, for example, TCFA, THFA, PIT, Fibrous or fibrocalcific, and compared with τ at each site. In NC plaques, fibrous cap thickness can be measured by depth-resolved ILSI and can be compared with Histology. Success can be determined by ANOVA tests to evaluate τ difference between groups, based on OFDI and Histology diagnosis, $p<0.05$ can be considered statistically significant.

Exemplary Alternate Embodiments

Exemplary optical rotary junction: In the unlikely event that about >10% deviation in τ can be observed during catheter rotation, an alternative approach (e.g., recently demonstrated in OCT) (see e.g., Reference 90) can be implemented in which the optical core can be maintained stationary, and torque can be conveyed to the distal mirror via a driveshaft. It can also be possible to the use of cone mirrors to conduct LSI. Assuming that cone mirrors can be sufficiently miniaturized, they can likely provide a viable option to enable omnidirectional viewing in the ILSI catheter.

Exemplary Alternate exemplary catheter designs: Exemplary ILSI procedures can be conducted in the conjunction with saline flushing. In the unlikely event that saline flushing does not sufficiently displace blood, a multi-prong contact based design can be employed that can maintain endoluminal surface contact during imaging. Similar contact based catheters can be utilized in thermography studies and can be approved for use in patients. (See, e.g. Reference 24).

Exemplary Depth-analysis: The in vivo feasibility of 3D analysis can be performed, and the performance metrics can be based on 2D maps of bulk τ measurements, based on the results of previous exemplary studies that establish the significance of bulk τ for assessing high-risk plaques.

Exemplary Methods

Optimal flushing parameters to conduct ILSI in patients: ILSI can be conducted in vivo while flushing with Visipaque to displace blood. To calculate the total imaging duration over which clear viewing of the arterial wall can be achieved, further studies have been conducted in living swine. Flushing with Visipaque was performed at flow rates of about 2-4 cc/s, commonly used in patients, and OFDI was simultaneously conducted to evaluate blood scattering within the lumen. For a single 10 cc flush at about 3 cc/s, optimal blood clearance and unobstructed viewing of the arterial wall was achieved over approximately 6 s (e.g., FIG. 19). From these results, it was inferred that to conduct ILSI in patients, 8 intermittent flushes (e.g., 10 cc/flush) of Visipaque can facilitate sufficient blood displacement to scan an approximately 5 cm long coronary segment in less than a minute (e.g., at a scan pitch=1 mm). Thus a low total volume of approximately 80 cc of Visipaque can be administered. The average volume safely administered in patients can be reported to be about 265±130 ml. (See, e.g., References 92 and 93).

Human ILSI study: Following regulatory approval, it can be possible to evaluate coronary plaque viscoelasticity using ILSI in a cohort of 20 patients with native CAD who present at the MGH cardiac catheterization laboratory for percutaneous coronary intervention ("PCI"). In order to test the feasibility of the ILSI approach in patients, intracoronary OFDI can be used to provide a microstructural context for ILSI results. Briefly, the culprit lesion can be determined from the patient's angiogram. The OFDI catheter can be advanced over a guide wire just distal to the culprit lesion. The maximum coronary length scanned can be about 5.0 cm (e.g., range: 2.0-5.0 cm, imaging/flush parameters calculated below are based on maximum length). During a 3 s, 3 cc/s flush, the OFDI catheter can be withdrawn at a pullback speed of about 20 mm/s to scan a 5 cm segment. Following the OFDI procedure, ILSI can be conducted. The ILSI catheter can be similarly advanced distal to the culprit lesion under fluoroscopic guidance. Safety can be evaluated by monitoring hemodynamic parameters, EKG and development of symptoms during the exemplary ILSI procedure. The ILSI catheter's rotational rate can be about 1.0 Hz and imaging can be conducted in conjunction with 8 intermittent flushes (e.g., 10 cc) at about 3 cc/s as detailed above to image a matching 5.0 cm length in <50 s. The total amount of Visipaque administered for the entire imaging procedure can be <100 cc. It can be expected that the exemplary procedure can add 15-20 minutes to the routine PCI procedure (e.g., typical duration of 120 minutes).

Data co-registration and analysis: To determine the feasibility of ILSI in patients, ILSI 2D viscoelasticity maps can be compared with plaque type and microstructural information obtained from OFDI. In order to accomplish accurate data comparisons, digital coronary angiography can be conducted at the start and end of both OFDI and ILSI procedures to permit data co-registration. Additional landmarks, including the guiding catheter, stent edges and side-branch vessels can be used to improve registration accuracy.11 Co-registration in the circumferential direction can be done by reading the motor encoder positions on the OFDI and ILSI rotary junctions. OFDI images can be interpreted using previously established methods to characterize coronary plaques as: TCFA, THFA, PIT, Fibrous or fibrocalcific. (See e.g., References 12, 62, 94 and 95). ILSI-OFDI correlations can be evaluated using ANOVA tests to assess the feasibility of ILSI in measuring distinct τ values based on plaque type. The feasibility of measuring depth-resolved viscoelasticity can be evaluated in NC plaques by co-registering ILSI 2D cross-sectional maps of τ distributions with corresponding OFDI cross-sections.

Exemplary Potential Problems and Alternative Strategies

Blood: Blood in the FOV can cause rapid blurring of speckle due to moving blood cells. Real-time speckle analysis can be implemented and scan repeated if τ<1 ms. An alternative solution to detect blood can be to incorporate simultaneous coronary viewing via the same catheter with a white light source and color camera.

Cardiac motion: For example, ILSI can be conducted without EKG gating. In the unlikely event that cardiac motion can be problematic, EKG gating can be utilized, and the feasibility of ILSI can be tested by evaluating discrete arterial sites predetermined by OFDI.

Nephrotoxicity: In patients with renal impairment, Lactated Ringers can be used which has provided good ILSI results in exemplary studies. In these patients imaging can be restricted to a <3.0 cm segment.

Culprit lesion: In the event that the culprit site can be inaccessible, OFDI and ILSI can be performed post-PCI.

OFDI: OFDI-ILSI comparisons can be verified. Since, no intracoronary technology exists to measure plaque viscoelasticity metrics in patients, in vivo ILSI feasibility can be tested using OFDI findings that have been well established for plaque evaluation. (See, e.g., References 12, 62, 94 and 95).

The developed by Snyder (see, e.g., Reference 120) can be applied to determine the various parameters of the fiber optic bundle as described herein. CMT can be an approximate analytical approach to study optical crosstalk between neighboring waveguides in terms of the coupling between guided modes of neighboring waveguides, to fully investigate coupling between all modes of adjacent fibers. The influence of multiple fiber bundle parameters on inter-fiber crosstalk and the modulation of transmitted laser speckles can be quantified. Furthermore, fiber bundle parameters can be defined to considerably reduce the modulation of transmitted speckle patterns caused by mode coupling between and within multi-mode cores.

TABLE 2

Specifications of two commercially available OFB

| OFB Type | Core size (μm) | Core to core spacing (μm) | NA |
|---|---|---|---|
| Type I | 4.5 | 7.4 | 0.40 |
| Type II | 3.5 | 6.5 | 0.40 |

Exemplary Devices and Methods for Achieving Omni-Directional Viewing

In an exemplary embodiment (e.g., FIG. 15) described and shown herein, the motor drive assembly can be used to conduct helical scanning of the vessel. The motor drive assembly can be modified to achieve a 360-degree rotation of the catheter, or it can be rotated over a limited, or partial angle, to illuminate and image a section or sector of the lumen circumference at one time. The exemplary design can include an optical rotary junction ("ORJ") that can couple light with the rotating optical core. In OCT catheters, the ORJ can be designed to couple light with a single optical fiber while continuously spinning at speeds of approximately 6000 rpm. The ORJ provided for the exemplary ILSI device can have two exemplary features: (i) it can facilitate coupling of light with a rotating catheter, and can include a fiber bundle with multiple optical fibers, and (ii) the ILSI catheter can be prevented from spinning continuously. In order to permit measurement of speckle decorrelation over about 25 ms at each circumferential location, a motor drive can be incorporated to rotate the optical core at discrete steps with a residence time of about 25 ms per step. The ORJ can include a collimating lens at the proximal end of the optical core to couple light into a central illumination fiber, and a motor coupled with the driveshaft to enable rotation. An exemplary CMOS sensor can be housed directly within or connected to the ORJ, and can transmit speckle patterns imaged via a stationary lens. The exemplary rotational rate of the catheter can be about 1 Hz. A linear pullback stage can facilitate translation/pullback during imaging over speeds between, but not limited to, about 0.25-1.0 mm/s. In this exemplary design, the inner optical core can be affixed within a driveshaft cable to convey torque from a motor, to facilitate helical scanning. Some or all of the inner cable (e.g., the optical fiber bundle and distal optics) can rotate.

In another exemplary embodiment of the present disclosure, the inner optical core can remain stationary, and mechanical torque can be conveyed only to the distal mirror that can be affixed to the driveshaft cable. In still another exemplary embodiment of the present disclosure, a ring of illumination fibers surrounding the collection bundle can be used to illuminate the tissue, and the distal mirror can be rotated. Via a ring of illumination fibers, the tissue can be illuminated using light with a single wavelength, or with multiple fibers illuminating the tissue using different wavelengths of light. This can facilitate a better separation and a more robust analysis of speckle patterns. There can also be no are no moving parts. Instead a multi-faceted mirror (e.g., figures described below) can be incorporated at the distal end for omnidirectional viewing of the entire circumference of the lumen (e.g., 360 degree omnidirectional viewing). The multi-faceted mirror can be a cone mirror. Alternatively, or in addition, a cone-polygon/pyramidal shaped mirror can be used in which one or more of the reflecting surfaces can include one or more flattened reflective facets. Multiple illumination fibers can illuminate different facets of surfaces of the multi-faceted mirror, and speckle images can be collected simultaneously from 2 or more facets. During image processing, images obtained from multiple facets can be unwrapped and reconstructed to visualize the entire circumference of the luminal tissue of interest as shown below.

In another exemplary embodiment of the present disclosure, the optical core can remain stationary, and a rotating galvo-mirror can be incorporated at the distal end. The mirror can be provided to fit within a less than about a 1 mm catheter sheath.

In some or all of the exemplary embodiments, an optional circular polarizer can be included to reduce the influence of back-reflections or specular reflections emanating from surfaces of the catheter sheath, or from the surface of the tissue of interest. Specular reflections can be removed using software during post-processing of speckle images. This can be achieved by, for example, thresholding the image based on the temporal statistics of speckle fluctuations where pixels with negligible speckle fluctuation can be masked out during analysis. This can ensure that only light, or other electromagnetic radiation, that has undergone multiple scattering can be analyzed to measure an index of tissue viscoelasticity.

Preventing a receipt of the same polarization from returning in the radiation (e.g., light) can be beneficial in reducing back-reflected light of the similar polarization state that has scattered only once, or a few times, from the catheter surfaces and/or surface of tissue, which can otherwise increase the strong background intensity and confound the sensitivity of the device in measuring laser speckle intensity fluctuations scattered from tissue. The polarizer can be replaced by computer software, or other methods, which can include spatial and temporal filtering that can similarly prevent back-reflections of light of the same polarization state. Filtering (e.g., to replace the polarizer) can be achieved by removing pixels in the image in which the intensity fluctuation can be zero, or negligible, over time caused by reflected light that has maintained its polarization state following a single or few scattering events. Thus, fluctuating speckles causes by depolarized light, which has undergone multiple scattering through tissue, can be analyzed to measure the mechanical properties of tissue.

Exemplary Image Processing and Visualization

Figure 33A:
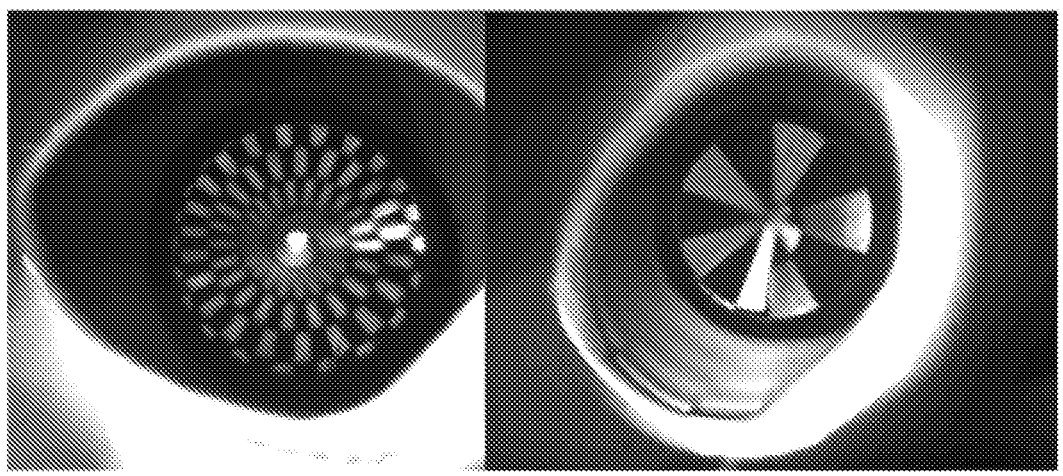
FIGS. 33A-33G are exemplary images of exemplary patterns according to an exemplary embodiment of the present disclosure.
Figure 33B:
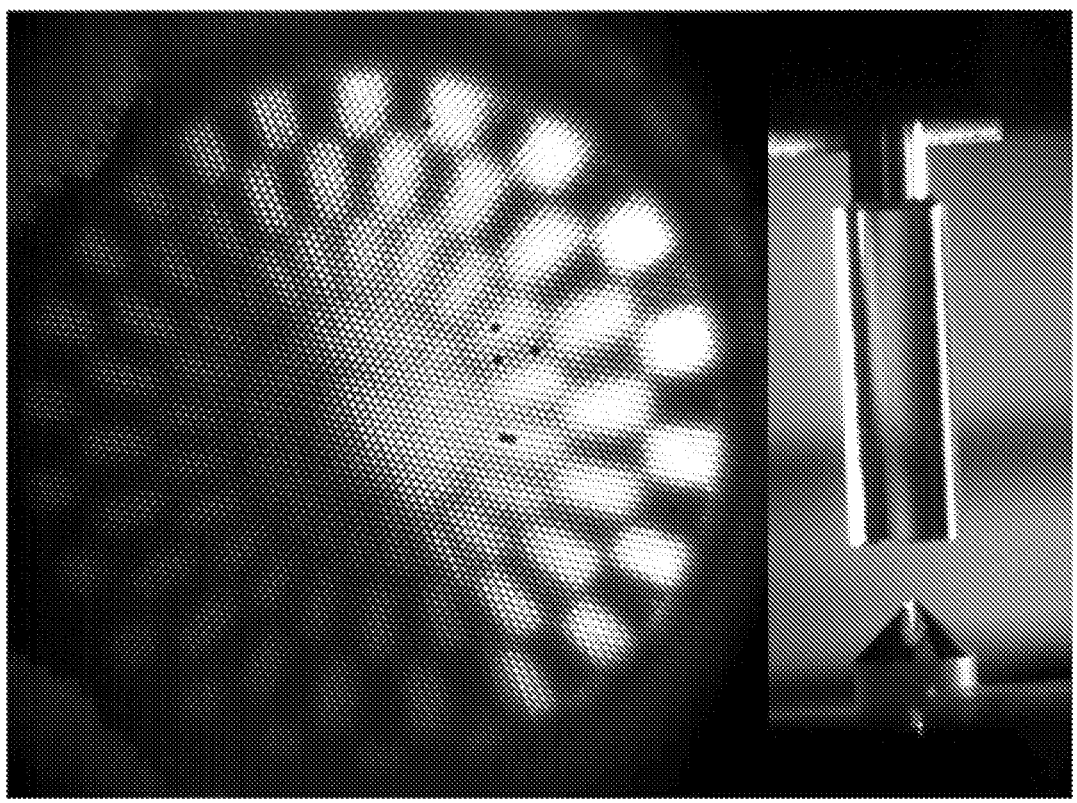
Figure 33C:
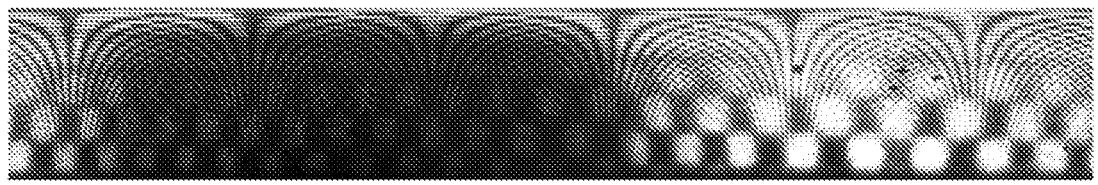
Figure 33D:
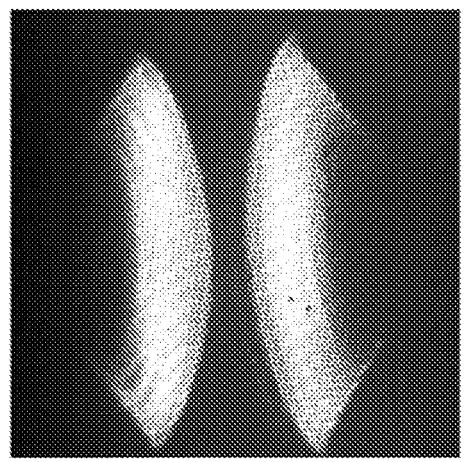
Figure 33E:
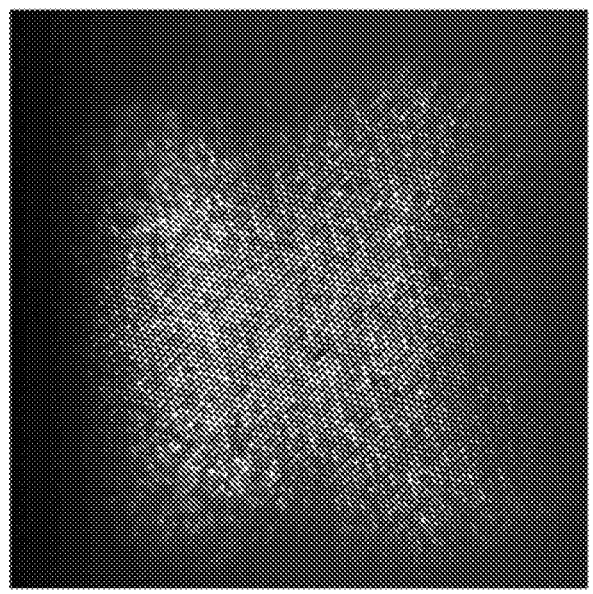
Figure 33F:
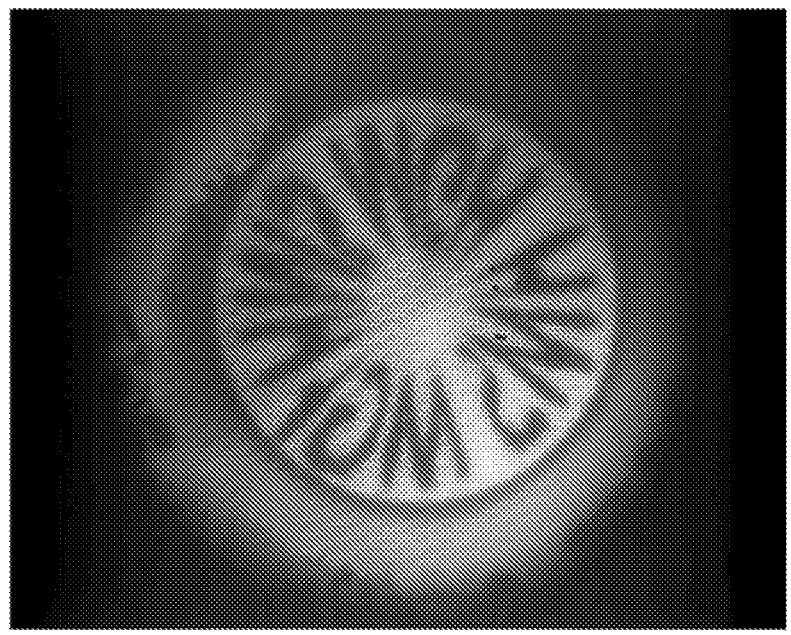
Figure 33G:
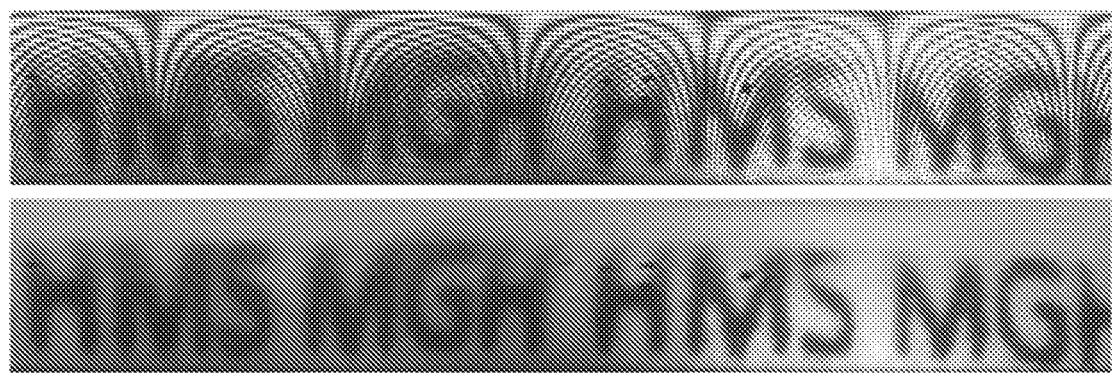
Figure 34:
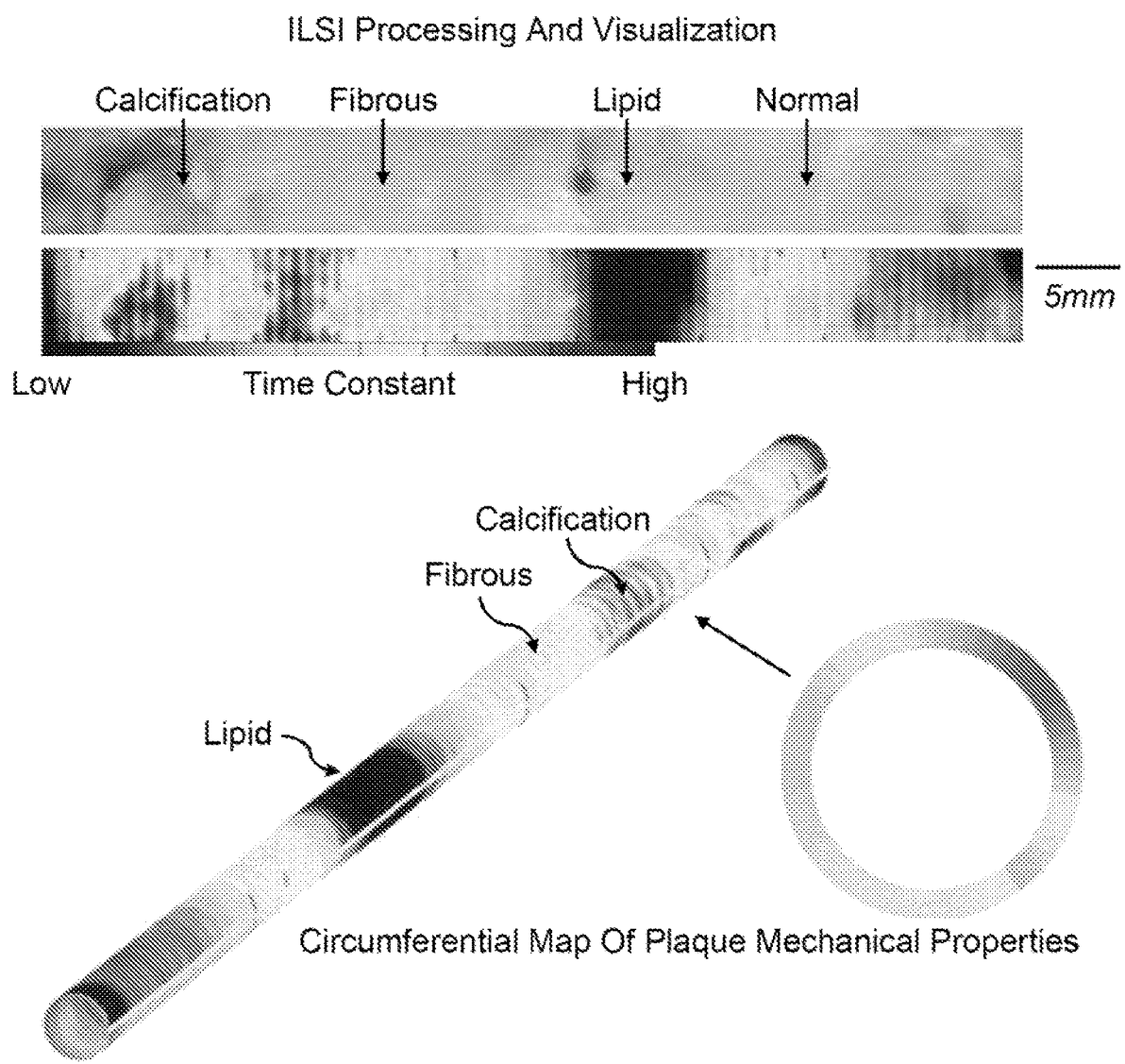
FIG. 34 is an image of an exemplary speckle pattern according to an exemplary embodiment of the present disclosure.
Figure 35:
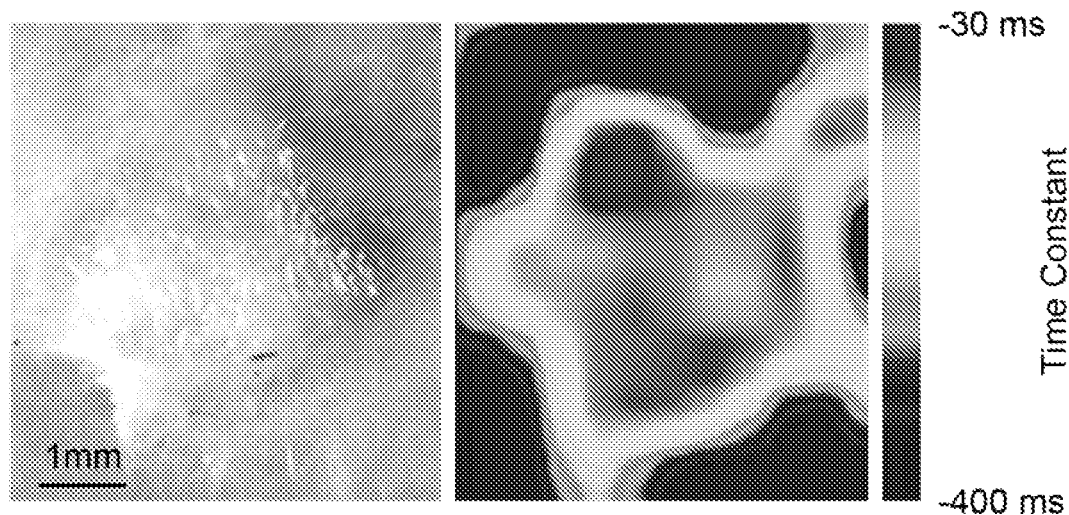
FIG. 35 is an exemplary image of an exemplary colormap according to an exemplary embodiment of the present disclosure.

Exemplary image processing procedures according to an exemplary embodiment of the present disclosure can include image unwrapping (e.g., FIGS. 33B and 33C) removal of pixilation artifact (e.g., FIG. 33F), spatio-temporal analysis of speckle fluctuations and visualization using a time constant color map and display. Various procedures can be used depending on the complexity of measurement that is required.

An exemplary procedure can include measuring measure the speckle decorrelation curve, $g_2(t)$, by cross-correlation of multiple speckle frames obtained over the time series, conducting spatial and temporal averaging over multiple $g_2(t)$ curves and determining the time constant by exponential fitting over short time scales. The speckle time constant can be reported as an index of tissue viscoelasticity. To extract 3D depth information, it can be possible to use a hybrid approach that combines Monte-Carlo ray tracing ("MCRT") with spatio-temporal windowed analysis of speckle patterns. This exemplary procedure has been previously been validated in necrotic core coronary plaque. (See e.g., Reference 43). It can also be possible to modify this exemplary procedure to account for changes in the number of scattering events as a function of depth.

Additional exemplary procedures can be provided to measure the elastic and viscous moduli of plaques directly from laser speckle patterns. $g_2(t)$ can be related to mean square displacement ("MSD") of light scattering particles within the plaque, and the MSD can be related to elastic and viscous moduli via the Stokes Einstein's formalisms. It can also be possible to display 2D maps of time constant by using spatial averaging, spatial filtering along with bilinear image interpolation techniques. It can be possible to further apply the above apparatus and methods for use in an exemplary helical/cylindrical display and for use co-registration for intra-coronary mapping. (See e.g., FIG. 1).

Exemplary Efficacy of LSI

In order to validate the use of the exemplary LSI to measure tissue mechanical properties, LSI results of time constant (e.g., on test phantoms and tissue) can be compared with mechanical testing using a rheometer, which has been previously shown to exhibit excellent correlation in these studies (e.g., R=0.79, p<0.05). (See e.g., Reference 42).

In order to validate capability of LSI to discriminate between plaque mechanical properties, LSI time constants compared with Histopathological diagnosis of tissue type can be performed by a Pathologist. Differences between time constant measurements for different tissue types can be evaluated using ANOVA tests. Both ex vivo and in vivo studies show distinction can be good between NC plaques and other plaque types (e.g., including normal, fibrous, calcific and pathological intimal thickening). (See e.g., References 46, 70 and 97). Since plaque mechanical properties can be dependent on collagen and lipid, correlation between time constant and collagen and lipid content within the measurement area of interest can be performed. Collagen content can be measured using Picrosirius staining, polarized light microscopy measurements and lipid using oil-red O, as well as immunohistochemical staining to detect Apolipoprotein B complex on LDL cholesterol. (See e.g., References 42, 45 and 95).

Sensitivity and Specificity of the exemplary LSI has been measured previously in ex vivo validation studies. (See e.g., Reference 42). This can be done by receiver operating characteristic ("ROC") analysis. The exemplary test can evaluate the capability of LSI to distinguish mechanical properties of thin cap fibroatheroma ("TCFA") plaques as these can be considered more unstable plaques of clinical significance. The presence of TCFA can be considered +ve diagnosis, and all other tissue types can be considered-vediagnosis. Both sensitivity (e.g., 100%) and spec (e.g., 92%) can be maximized, which can be used with a diagnostic threshold of time constant of about 76 ms. These exemplary studies can be similarly performed for in vivo studies.

Sensitivity=True Positive/(True positive+False Negative) and specificity=True Negative/(False Positive+True Negative). Flushing using contrast agents, lactated ringers or dextran solution can be routinely used in the catheterization laboratory for OCT and angioscopy imaging. Additionally, a contrast agent can be routinely used for angiography for a number of years. No major technical challenges can be expected in the flushing process, and this mechanism can be manual or automated. It can be possible to provide procedures to optimize flushing for ILSI (e.g., parameters: type of flushing agent, rate of flush, volume of flush, etc.) similar to OCT/angioscopy.

A practical challenge can potentially be inadequate flushing. Usually, the presence of blood can be easily detected as it can cause very rapid speckle decorrelation, and can provide a distinct time constant signature. To detect problems with inadequate flushing, it can be possible to include white light source to conduct color angioscopy in tandem through the same catheter. Alternately, various other exemplary methods can be used (e.g., a dual wavelength illumination to measure absorption due to presence of blood).

If flushing still poses a challenge, proximal balloon occlusion can be used for a short period of time. Flushing for clearing blood from the field of view during optical imaging can be routinely employed in angioscopy as well as and OCT/OFDI. Over 1000 studies have been published, and this exemplary method is well accepted by clinicians. Furthermore, flushing the coronary tree with contrast agent has been routinely used for many decades in conventional angiography procedures.

Figure 36:
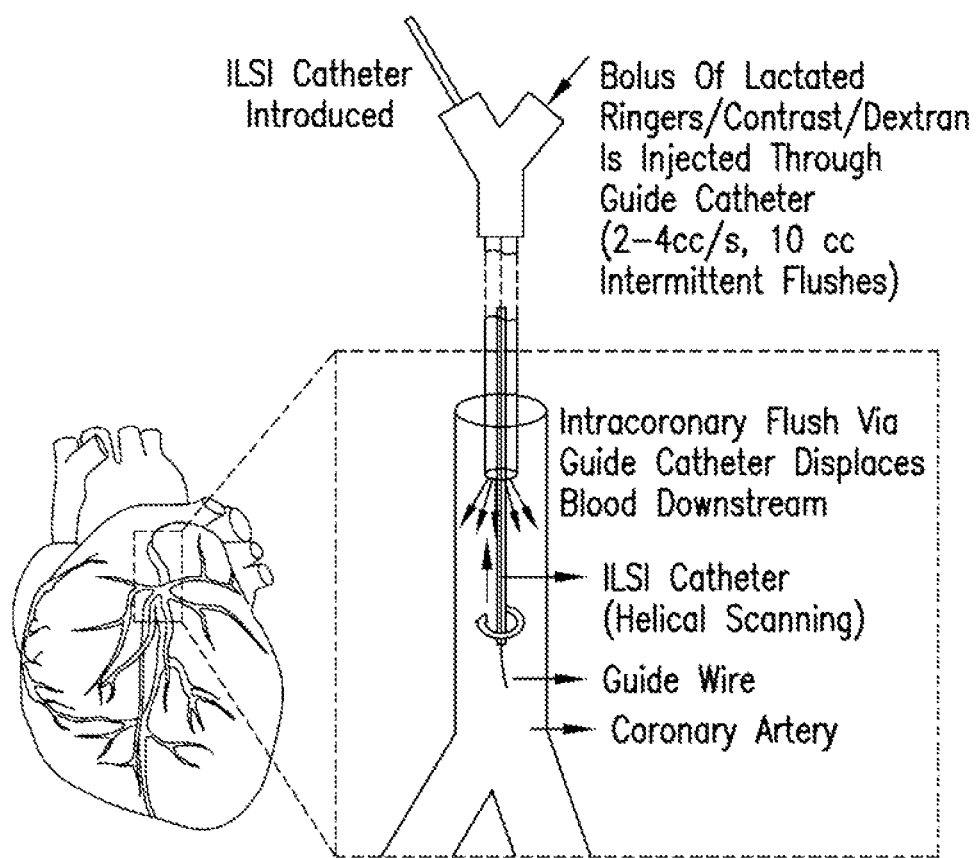
FIG. 36 is an exemplary schematic illustrating an exemplary mechanism for the displacement of blood during imaging according to an exemplary embodiment of the present disclosure.
Figure 37:
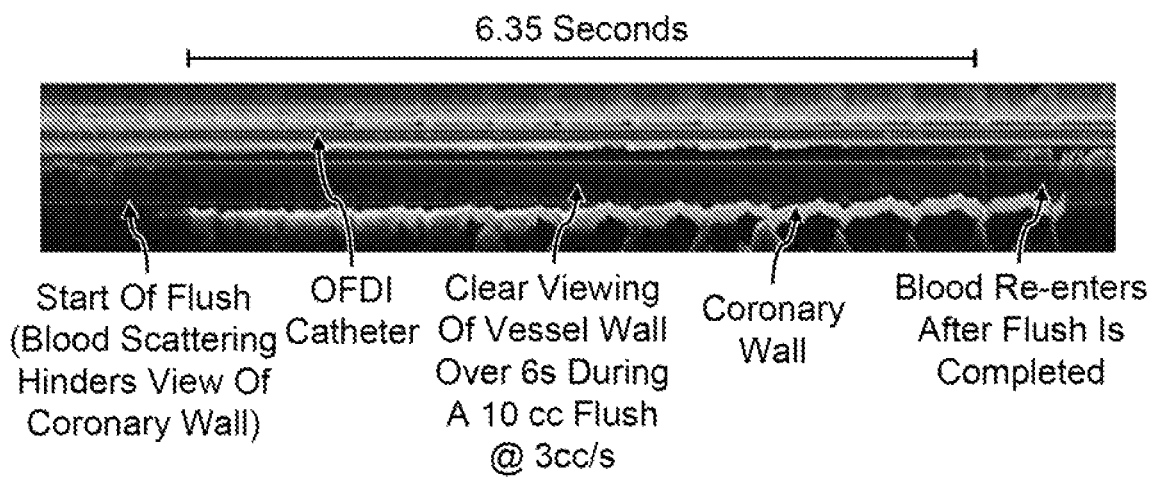
FIG. 37 is an exemplary image of exemplary M-mode OFDI according to an exemplary embodiment of the present disclosure.

ILSI can be conducted, in vivo, while flushing with contrast agent or lactated ringers can be used to displace blood. The exemplary flushing mechanism is described in FIG. 36. Using calculations based on exemplary OCT studies in swine (e.g., FIG. 37) to conduct ILSI in patients, the use 8-10 intermittent flushes (e.g., 10 cc/flush) of diluted contrast agent or lactated ringers Visipaque can permit sufficient blood displacement to scan an approximately 5 cm long coronary segment in less than a minute (e.g., at a scan pitch=1 mm). Thus, it can be expected that a low total volume about 80-100 cc of flushing agent can be administered during ILSI, which can be below the average volume that is safely administered in patients. (See e.g., References 92 and 93).

According to a further exemplary embodiment of the present disclosure, it is possible to provide a miniaturized (e.g., <1 mm) ILSI catheter that can be safely guided through the coronary artery to conduct intracoronary mapping. It can be beneficial to keep the exemplary device as similar to a commercially available (e.g., regulatory approved) IVUS catheter and system as possible. It can also be possible to confirm ILSI catheter characteristics (e.g., damage to endothelium, trackability, pushability and ease of use) are similar to an exemplary IVUS catheter.

Exemplary Analysis of Omni-Directional Mirror Configurations

Exemplary embodiments of exemplary omni-directional catheters can include reflective arrangements or at least partially-reflective arrangement that can include multiple facets at the distal tip of the catheter to direct electromagnetic radiation to the cylindrical lumen, and to collect reflected speckle patterns from multiple sites of the lumen circumference without rotating the catheter.

Figure 38A:
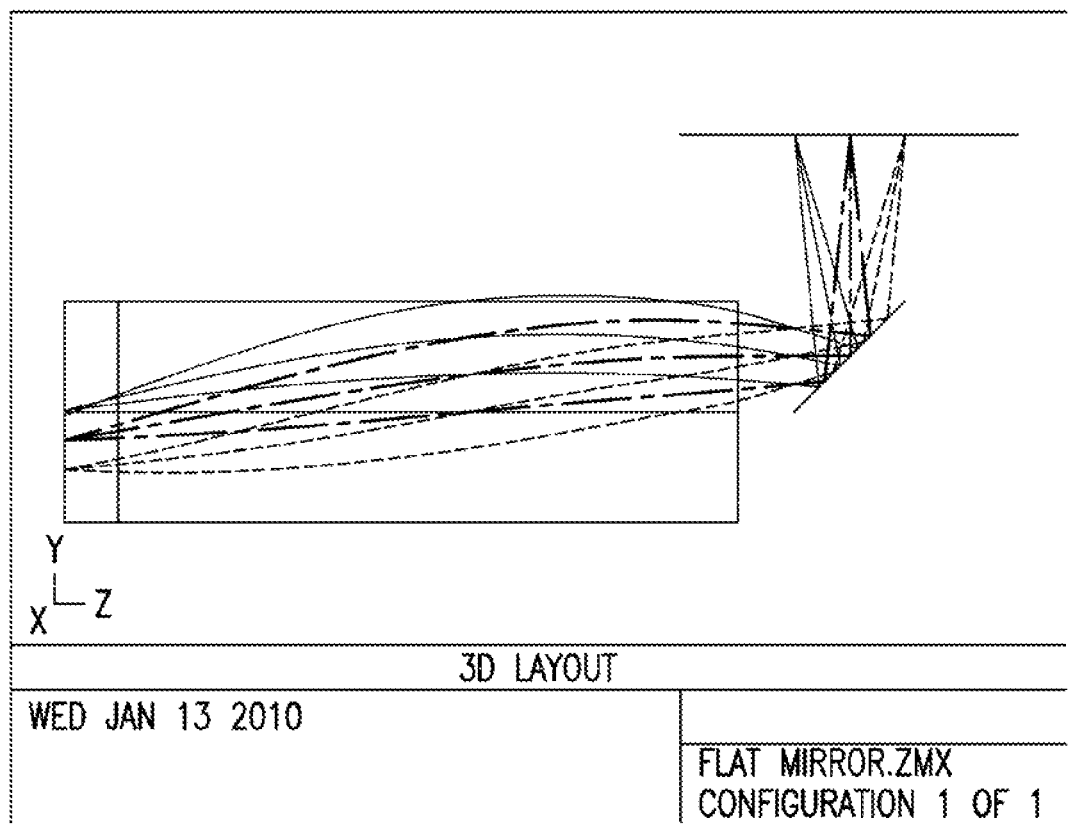
FIGS. 38A-38L are exemplary schematic diagrams of exemplary catheters according to an exemplary embodiment of the present disclosure.
Figure 38B:
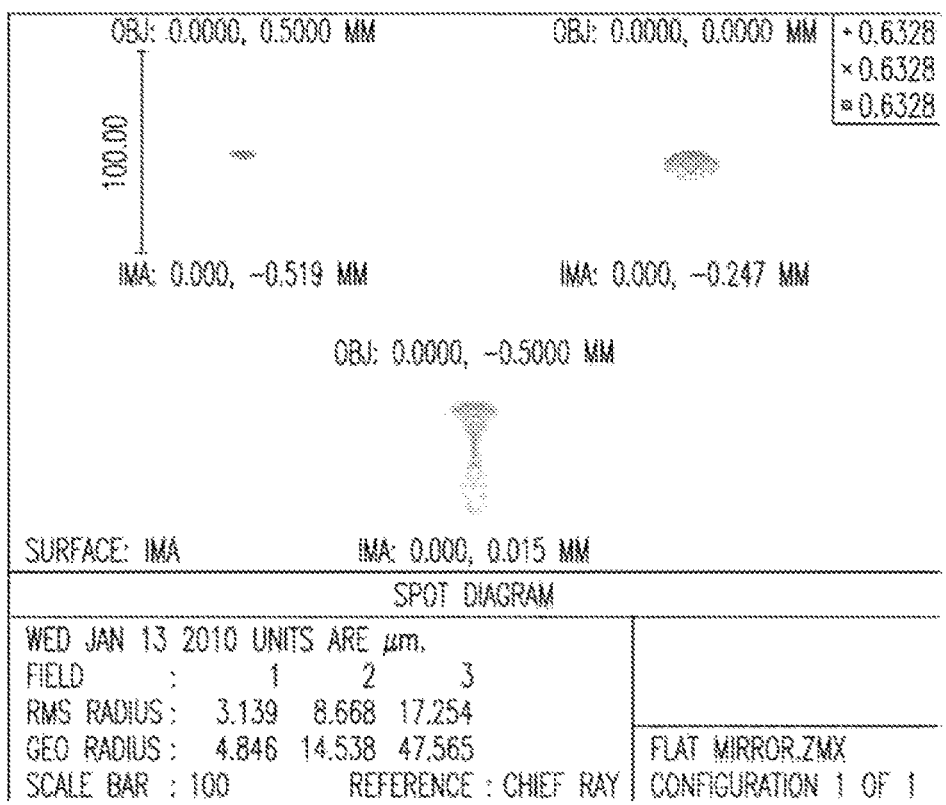
Figure 38C:
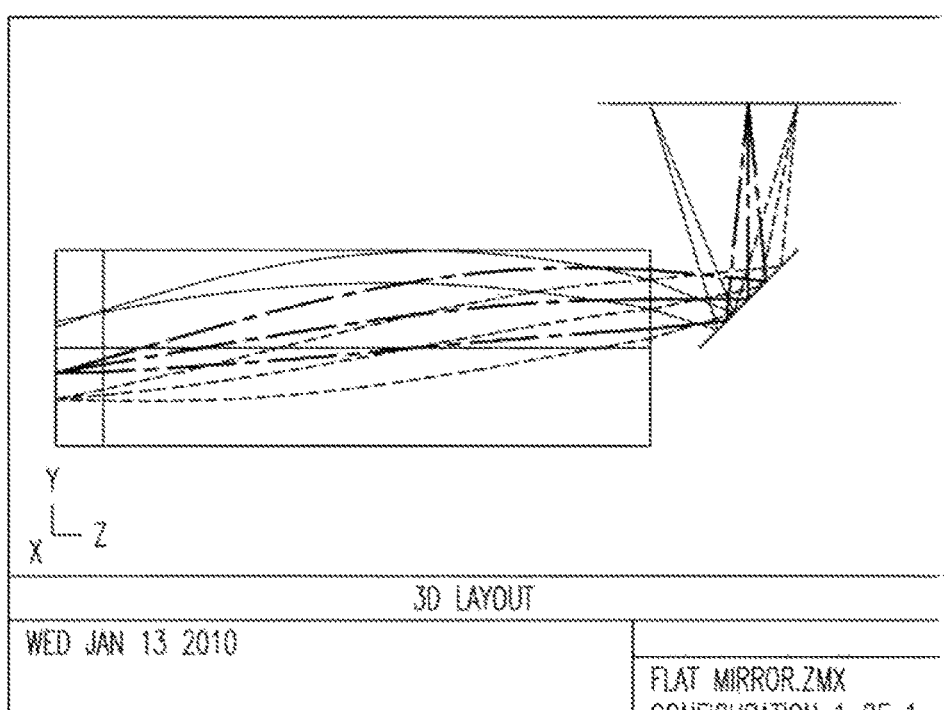
Figure 38D:
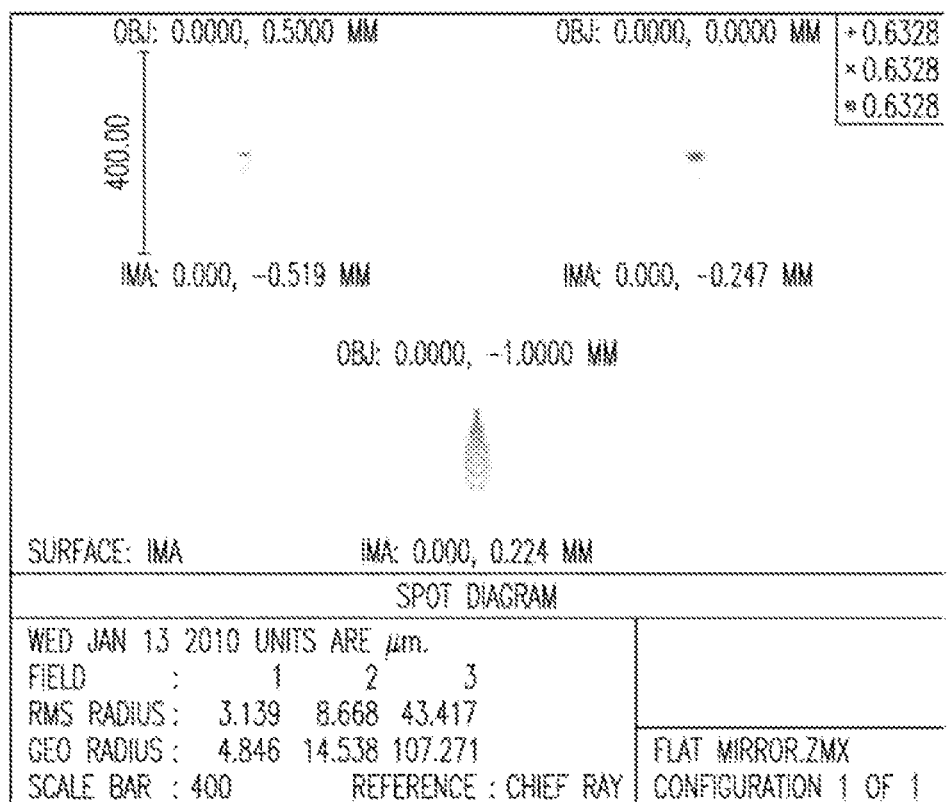
Figure 38E:
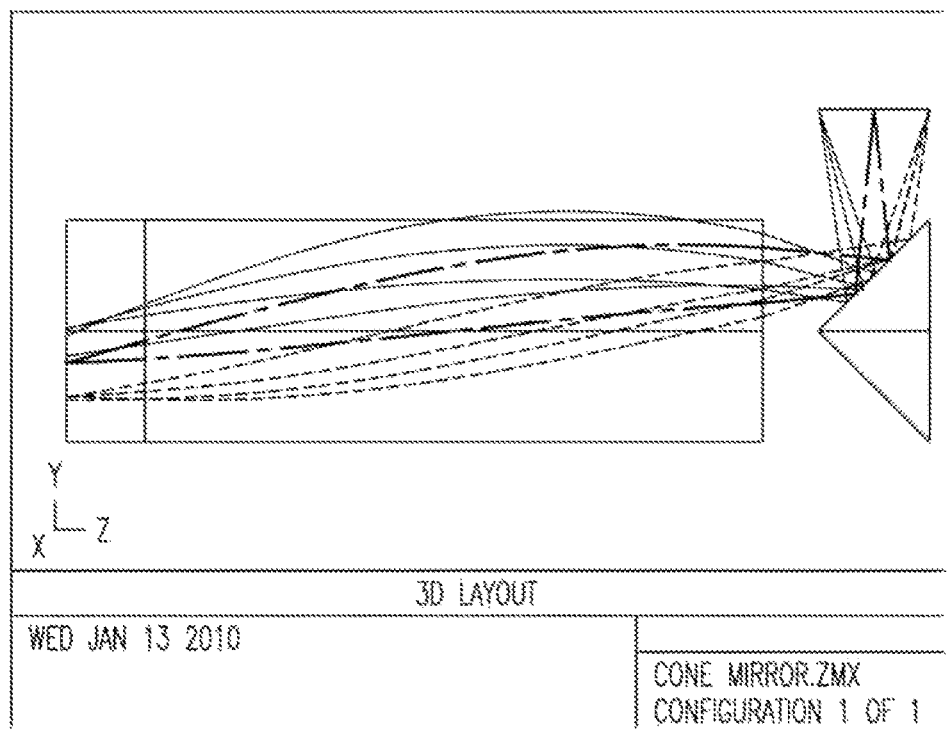
Figure 38F:
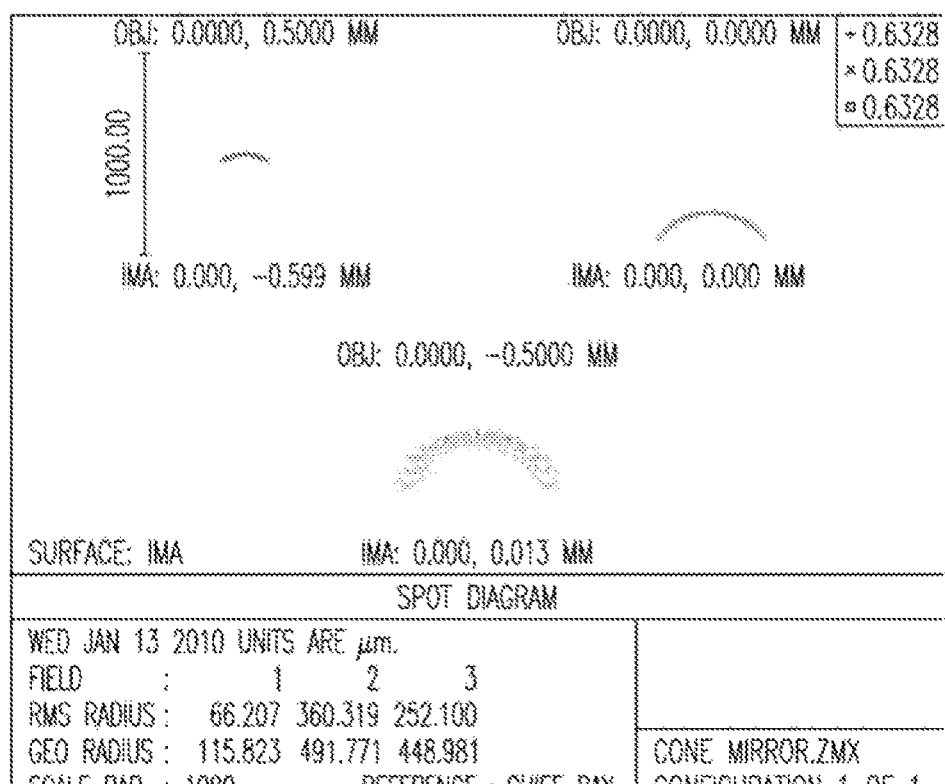
Figure 38G:
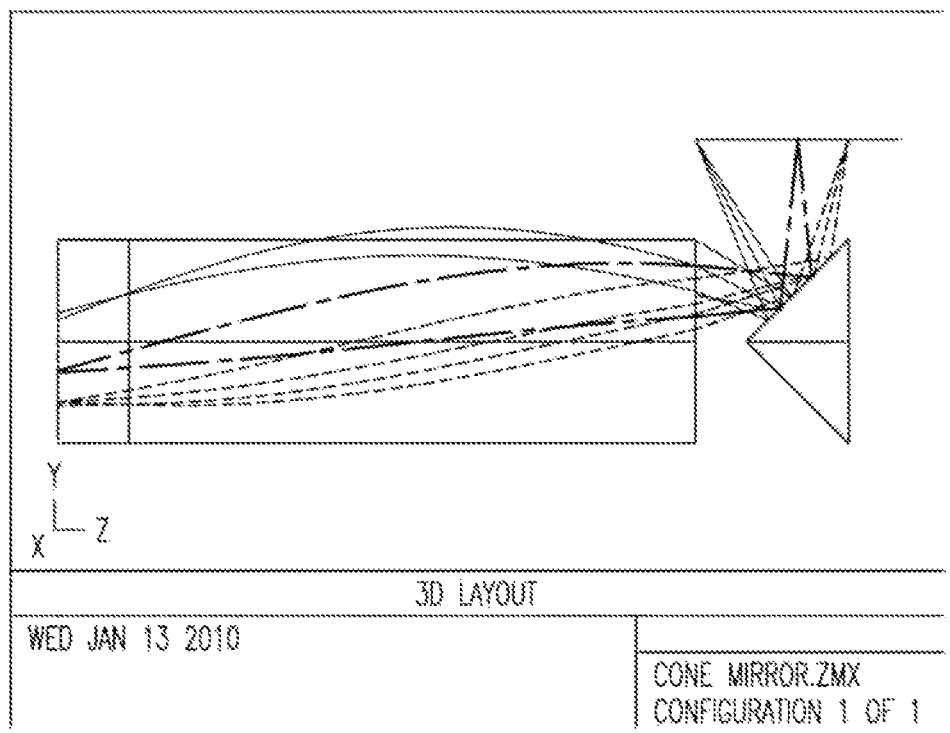
Figure 38H:
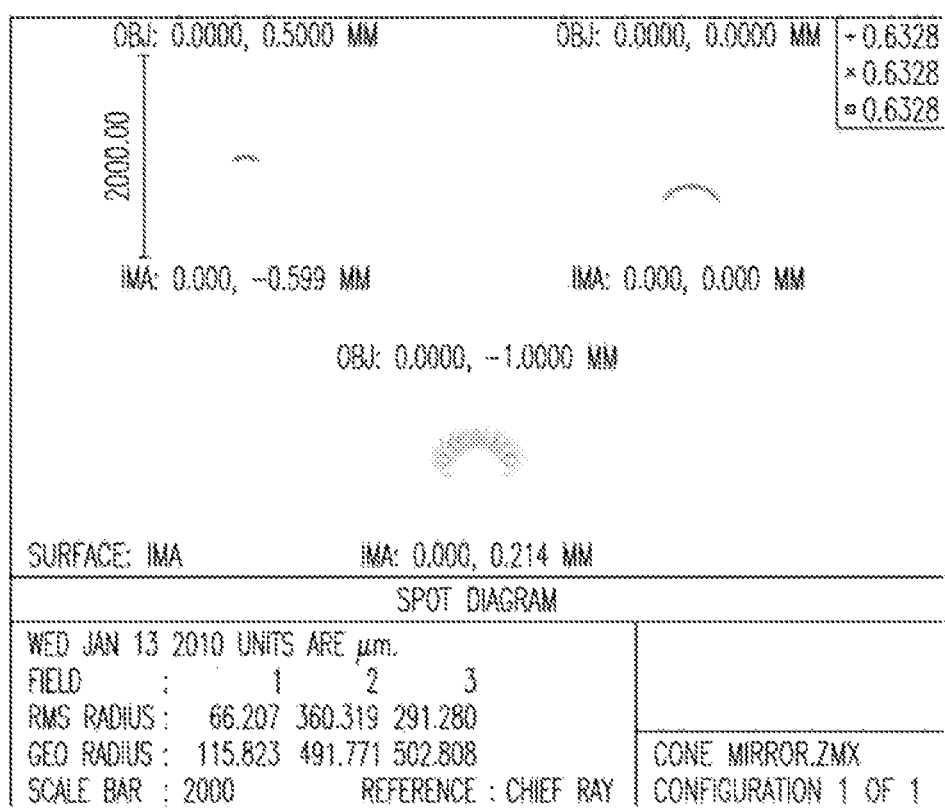
Figure 38I:
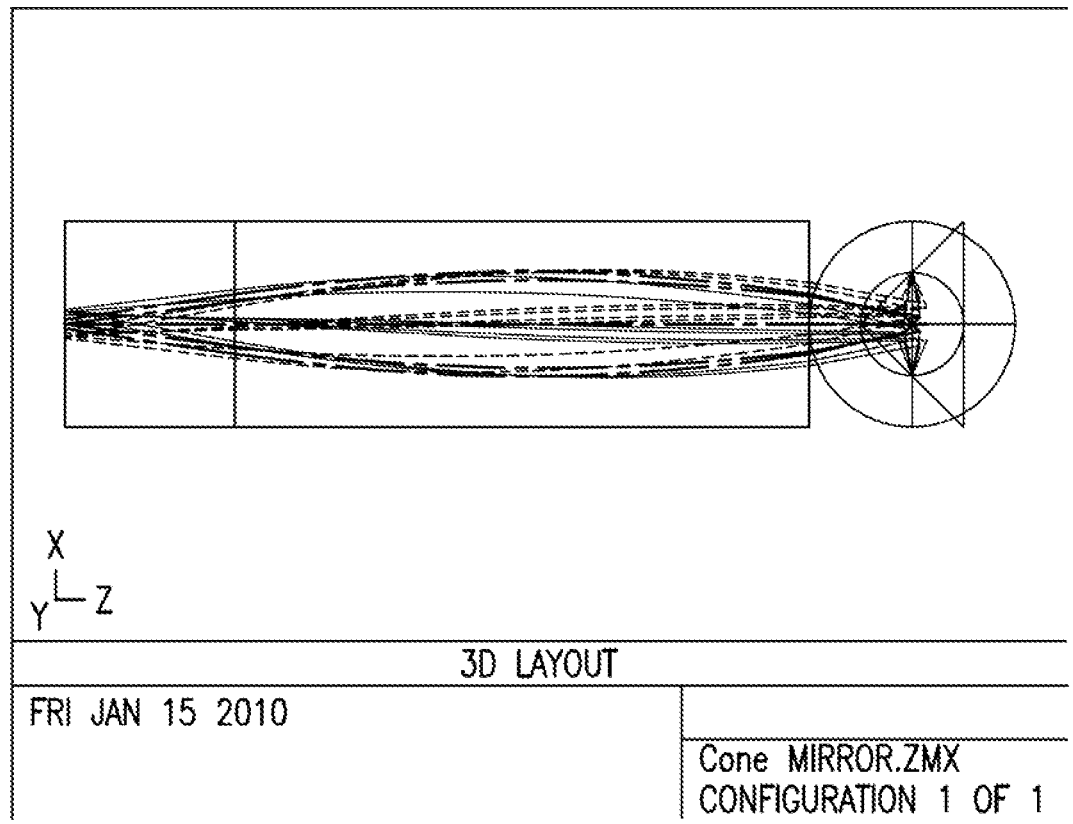
Figure 38J:
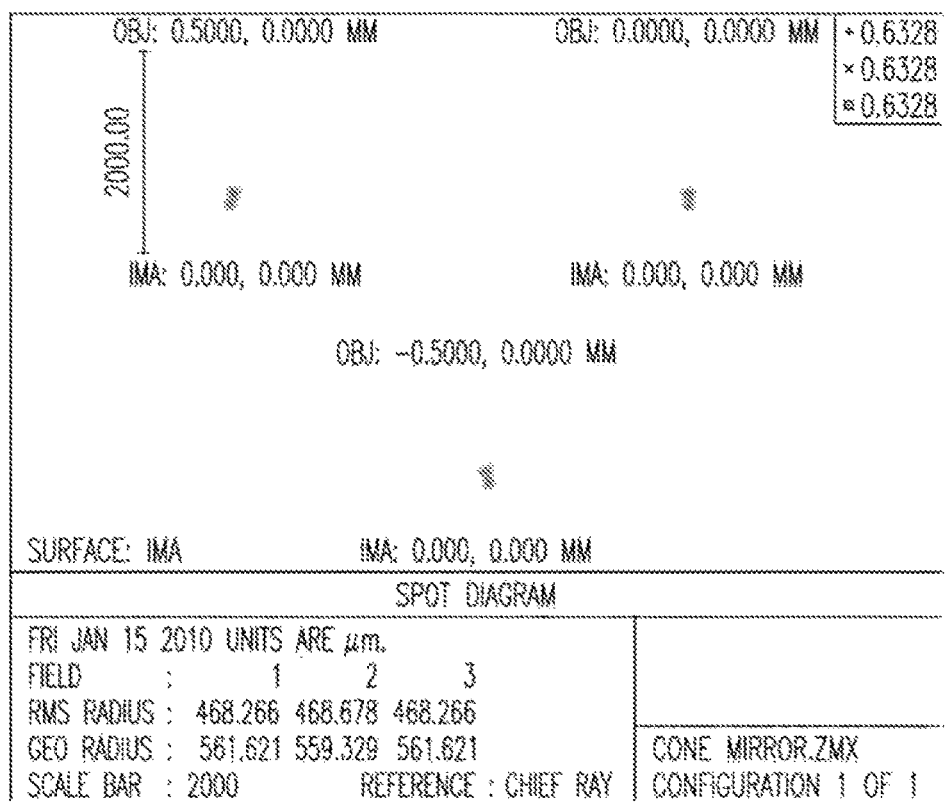
Figure 38K:
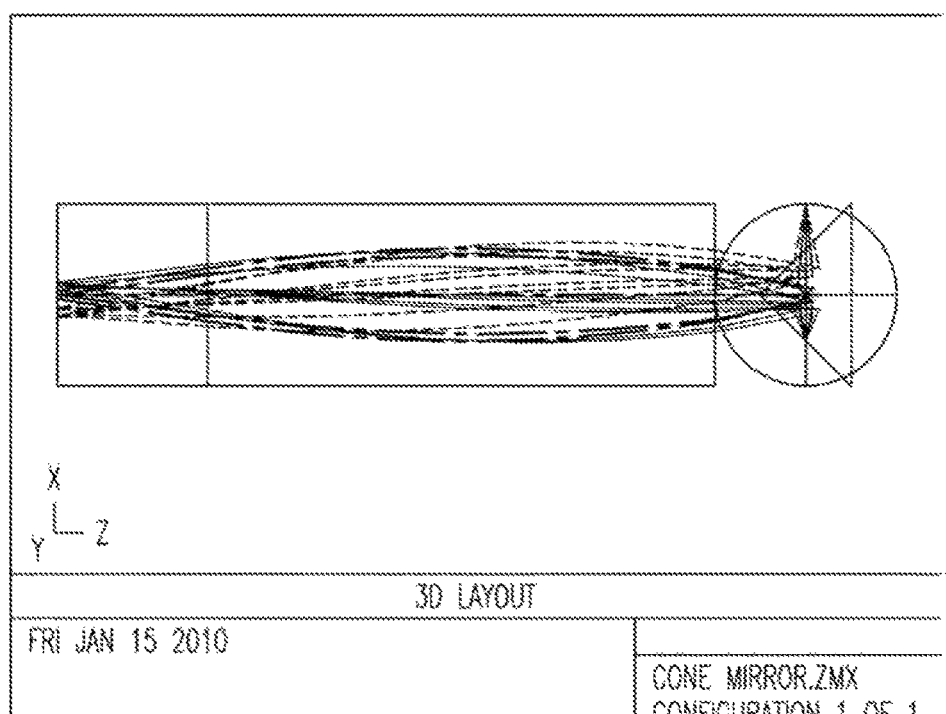
Figure 38L:
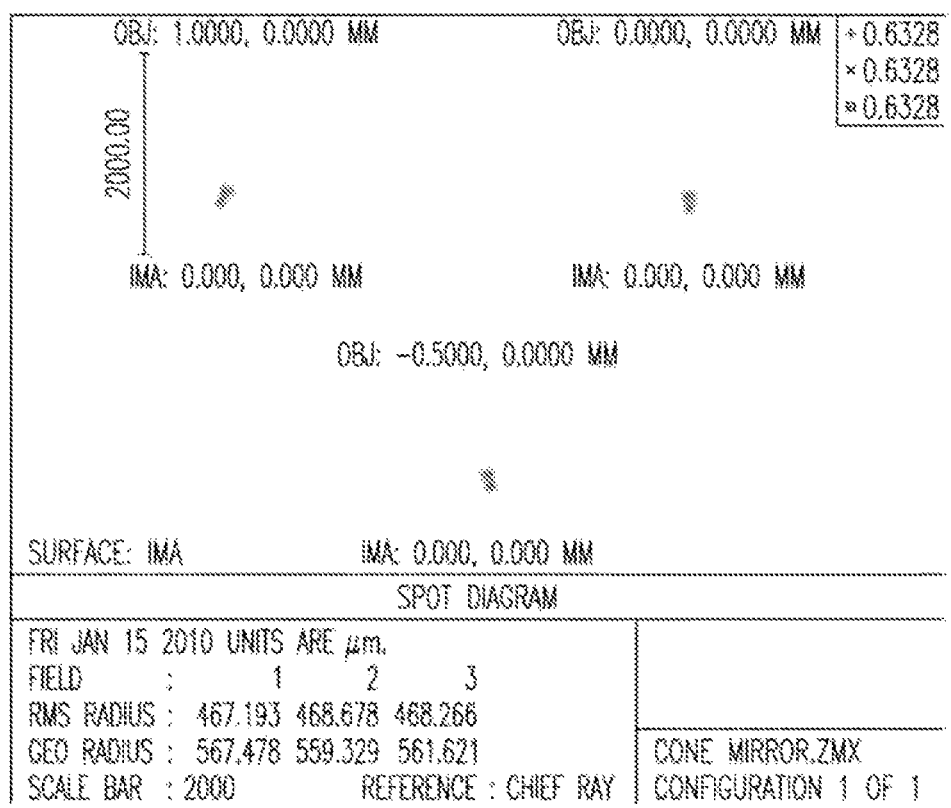
Figure 39A:
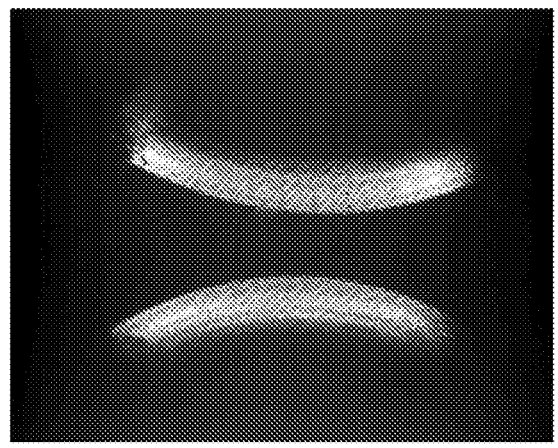
FIGS. 39A-39H are exemplary images of exemplary laser spots according to an exemplary embodiment of the present disclosure.
Figure 39B:
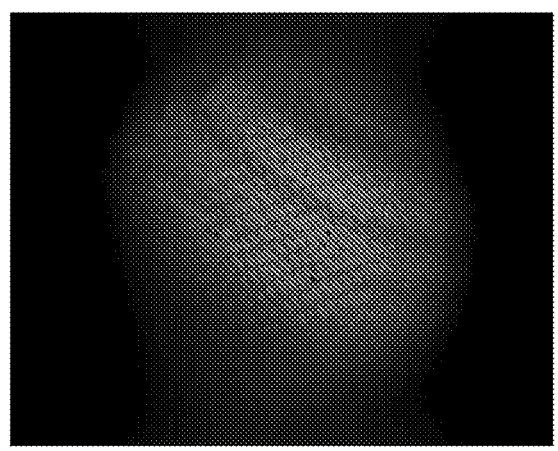
Figure 39C:
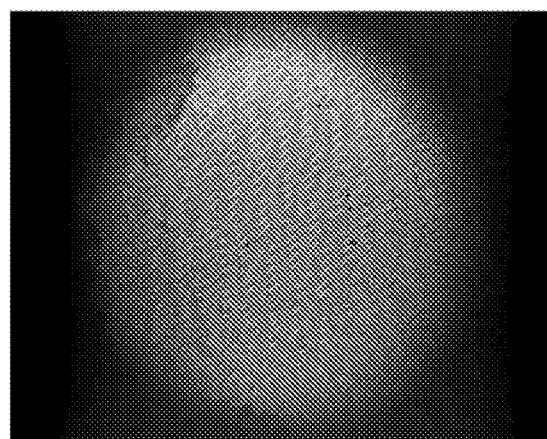
Figure 39D:
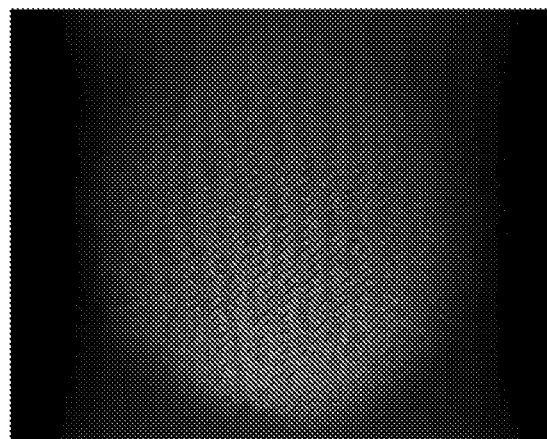
Figure 39E:
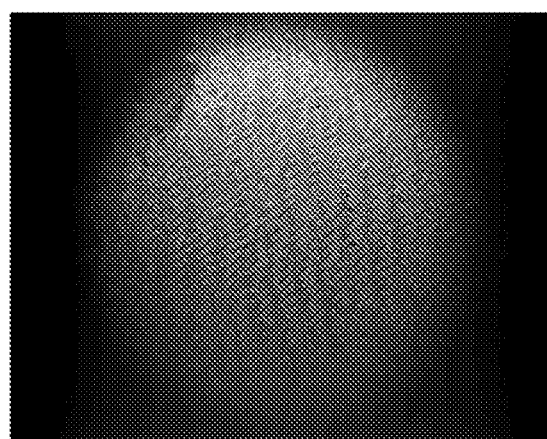
Figure 39F:
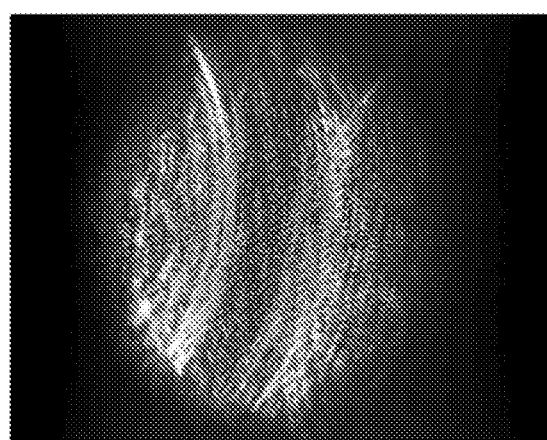
Figure 39G:
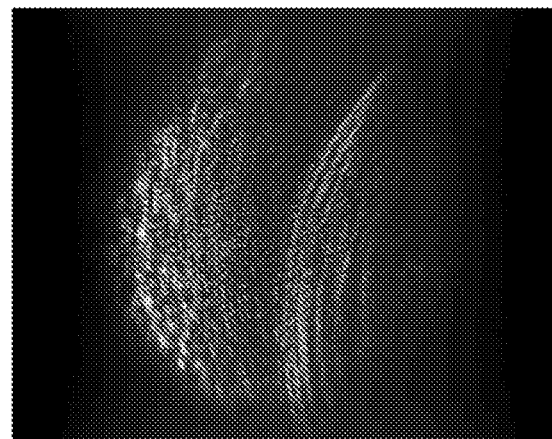
Figure 39H:
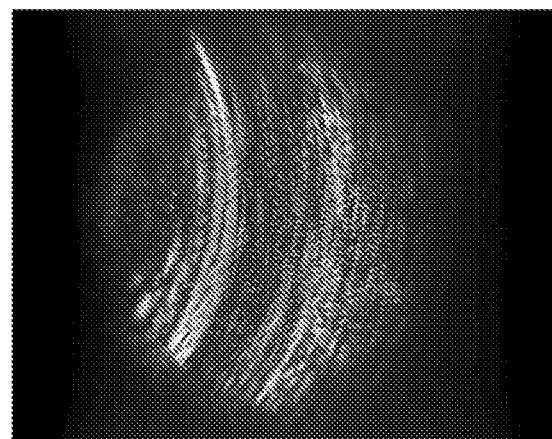

FIGS. 38A-38C illustrate an exemplary cone-polygon/pyramidal mirror for omni-directional (e.g., laser speckle, etc.) imaging. The image is at the bottom of the image plane for the object that is at the top of the mirror. At the image plane, the central part can have more aberrations and a larger spot radius, while the edge can have less aberrations and smaller spot radius. The spot size at the edge can be smaller than a fiber's cross-section surface. Additionally, the off-axis object can cause overlap of the images if the off-axis object has an enough large distance.

FIGS. 38E-38H illustrate an exemplary cone mirror-side view for vertical focal plane. The image is at bottom of the image plane for the object at the top of the mirror. At the image plane, the central part can have more aberrations more aberration and a larger spot radius, while the edge can have less aberrations and smaller spot radius. The spot size at the edge can be smaller than a fiber's cross-section surface. The off-axis object can cause overlap of the images if the off-axis object has an enough large distance. The horizontal aberration can be very strong due to curvature of the cone mirror.

FIGS. 38I-38L illustrate an exemplary cone mirror top view for horizontal focal plane. The vertical focal plane and horizontal focal plane can be at different location, (approximately 1 mm difference. Strong horizontal image aberrations can be seen, and can cause severe image overlap horizontally. Also present, is a big spot size, and an inadequate horizontal resolution.

FIGS. 39A-39H illustrate exemplary images obtained using various exemplary omni-directional mirror configurations. Exemplary selections of fiber bundle parameters can be used to reduce inter-fiber cross-talk during laser speckle imaging.

Figure 20A:
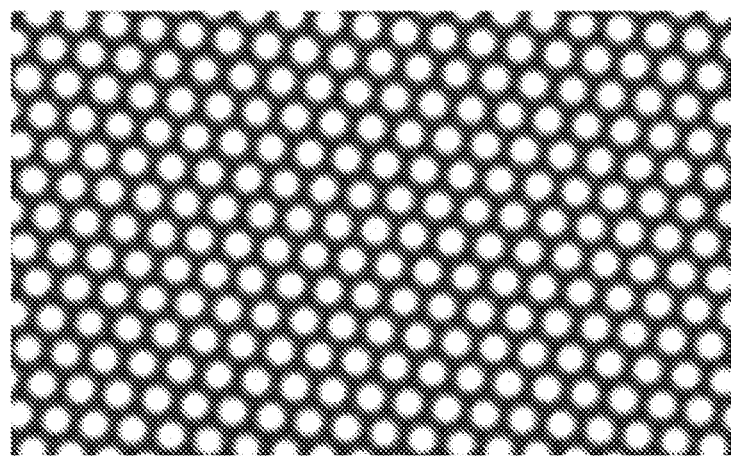
FIG. 20A is an image of cross section of a leached fiber bundle according to an exemplary embodiment of the present disclosure.
Figure 20B:
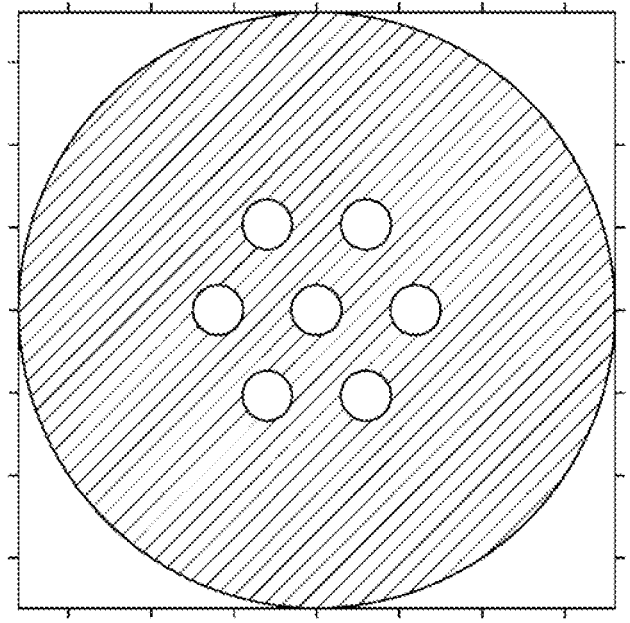
FIG. 20B is a schematic of fiber bundle in numerical calculations according to an exemplary embodiment of the present disclosure.

Optical fiber bundles can typically incorporate thousands hexagonally arranged individual optical fiber cores as shown in FIG. 20A. The analysis of mode coupling between all of the fiber cores can be far too complicated and numerically intensive to be calculated. However a simplified system of 7 parallel fibers can be used to model the coupling between the modes of these fibers (see, e.g., References 115-117) and the result can be easily extended to an entire fiber bundle. Here, a multi-core optical fiber system of 7 hexagonally arranged cores embedded in a uniform cladding material as shown in FIG. 20B, can be used. The fiber bundle specifications can be based on two commercially available leached fiber bundles (e.g., SCHOTT North America) and are listed in Table 2 above. These two types of fiber bundles were chosen because their specifications can be typical for the fiber bundles used in LSI. (See, e.g., Reference 100).

Coupled mode theory (see, e.g., References 114 and 120-122) can be a common theoretical model used to obtain approximate solutions to the coupling between waveguides of multiple waveguides systems. Compared to the normal mode expansion method (see, e.g., Reference 115), in which the field can be expanded in terms of normal modes solved from Maxwell's equations with the boundary conditions of the entire complicated structure, in CMT the field can be decomposed into the modes of each individual waveguides (see, e.g., Reference 114):

$$E(x, y, z) = \Sigma_v \alpha_v(z) e_v(x, y) \exp(i\beta_v z) \quad (3)$$

$$H(x, y, z) = \Sigma_v \alpha_v(z) h_v(x, y) \exp(i\beta_v z)$$

where $a_v$ can be a complex amplitude of vth mode; $e_v$ and $h_v$ can be electric and magnetic components of normalized mode field of each individual fiber, respectively; $\beta\mu$ can be the mode propagation constant of mode $\mu$; z can be the propagation distance along the fiber bundle and the summation over v runs through all modes of all individual fibers. The effective refractive index of mode Er can be defined as neff=$\beta\mu/k$, where k=$2\pi/\lambda$ can be the wave number. For complex structure, the complete set of the normal modes can be difficult to solve out (see, e.g., Reference 115) while in CMT, modes of each core of fiber bundle can be solved independently. The complex amplitude of modes can be obtained by solving the coupled mode equation (see, e.g., Reference 114) which can describe how the amplitude can vary with propagation distance z along with the length of the coupled waveguides, where, for example:

$$\frac{da_v}{dz} = \sum_\mu i\kappa_{v\mu} a_\mu \exp(i\Delta\beta_{v\mu} z), \quad (4)$$

where $\kappa_{v\mu} = c_{v\nu}[c^{-1}\tilde{\kappa}]_{v\mu}$ can be the mode coupling coefficient between mode v and μ. The coupling coefficient can be directly related to the degree of overlapping of mode field. The coupling coefficient kvμ along with the difference in mode propagation constant $\Delta\beta_{v\mu} = \beta_\mu - \beta_v$ decide the strength of μth mode, mode to vth mode. The mode coupling coefficient $c_{v\mu}$ can be determined by the overlap coefficient of mode fields (ev, hv) and (eμ, hμ) and the perturbation $\tilde{\kappa}_{v\mu}$ of mode μ to the mode v. Here the element of matrix $c_{v\mu} = \iint (e^*_v \times h_\mu + e_\mu \times h^*_v) \square z dxdy$ and $c_{v\mu}$ for the normalized mode field by definition. The element of matrix x can be given by, $\omega \iint \Delta\varepsilon_\mu e^*_v \square e_\mu dxdy$, where ω can be the angular frequency of the laser light and $\Delta\varepsilon_\mu(x,y) = \varepsilon(x,y) - \varepsilon_\mu(x,y)$ can be the difference between the dielectric constant of the whole multi-core structure and the dielectric constant of the structure with only the individual fiber supporting the mode μ.

To evaluate the modulation of laser speckle patterns during transmission through the optical bundles, laser speckle fields can first be numerically generated (see, e.g., Reference 97) by Fourier transform the field with random phase. The polarization of speckles can be chosen along with the linear polarization of fundamental modes of fibers. The generated speckle fields can then be decomposed into HE, EH, TE and TM fiber modes of individual fibers. The complex amplitude of each guided fiber mode at z=0, av(0), can be given by for example:

$$\alpha_v(0) = \iint e^*_v \square E_0 dxdy, \quad (5)$$

where $E_0$ can be the generated speckle electric field. By solving the Eq. (4) for each propagating mode with the initial value of $a_v(0)$, the complex amplitude at propagation distance z can be obtained. The transmitted speckle patterns can then be reconstructed by linearly combining the fields of all fiber modes with its amplitude. The modulation of the transmitted speckles can then be evaluated by the correlation coefficient of the intensity patterns between reconstructed speckle patterns at different positions along the length of bundles and the reconstructed speckle patterns at z=O (see, e.g., Reference 27), where, for example:

$$C(z) = \frac{\overline{(I(x, y, z) - \bar{I}(z)(I(x, y, z=0) - \bar{I}(z=0))}}{\sigma_1(z)\sigma_1(z=0)}, \quad (6)$$

where I(x,y,z) can be the intensity of speckle electric field $E(x,y,z) = \sum_v \alpha_v(z) e_v(x,y) \exp(i\beta_v)$; $\bar{I}(z)$ and $\sigma_1(z)$ can be the spatial average and standard deviation of the intensity patterns at different z, respectively. Here x, y can be the transverse coordinates of the points within the 7 core areas. C=1 can indicate that two speckle patterns can have same spatial fluctuations and so totally correlated when C=0, the speckles patterns can have no correlation. Thus the average of C over 20 speckle realizations can be used to measure the speckle modulation.

Exemplary Speckle Image Processing

Exemplary Elimination of Pixelation Artifact

Figure 26A:
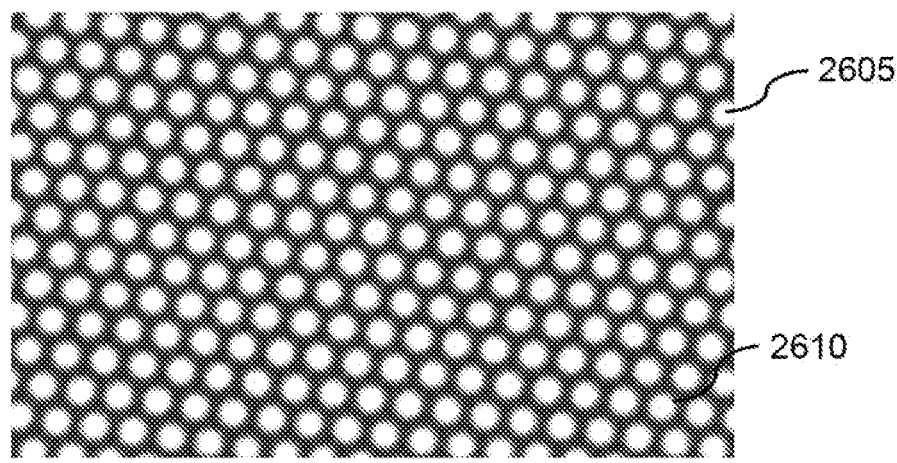
FIG. 26A is an exemplary image of a small region of an optical fiber bundle cross section according to an exemplary embodiment of the present disclosure.

To conduct ILSI, a small-diameter, flexible optical fiber bundle can be used to transmit the laser speckle patterns reflected from the coronary wall to the high speed CMOS camera at the proximal end of the imaging catheter. However, the hexagonally assembled optical fibers can create a honeycomb-like pixelation artifact, as shown in FIG. 26A. Each white round area 2605 is a fiber core. The dark gaps 2610 between cores are the fiber cladding. Due to these gaps, the speckle images may not be continuous. These gaps can also reduce the number of pixels covered by each speckle, and can therefore reduce the efficiency of spatial average in calculating the temporal statistics of speckles patterns, such as the speckle autocorrelation, within a certain spatial area. Thus, the area can be enlarged to include more pixels to obtain an adequate spatial average. Consequently the spatial resolution of the exemplary maps of the arterial viscoelasticity distribution constructed from the speckle fluctuations can be degraded. This degradation can limit the ability to distinguish morphological features of tissues, such as the size and shape of plaques. To eliminate the pixelation artifact, two exemplary numerical methods can be applied for two distinct speckle size regimes (e.g., speckle sizes larger than core spacings and speckle sizes smaller than core spacings).

Exemplary Speckle Size Larger Than Core to Core Spacing

According to the Nyquist-Shannon sampling theorem, if the speckle size can be larger than the core spacing between two neighboring cores, the spatial frequencies of the speckle patterns can be lower than that of the hexagonal pattern of fibers. Therefore, the hexagonal pattern of fiber cores in Fourier domain can be removed by applying a low pass filter whose cut-off frequency can be no less than the highest spatial frequency of the speckle pattern.

The recorded raw images can be transformed (e.g., using a Fourier transform) to spatial frequency domain and then multiplied by a low pass filter HB(u,v) (e.g., a Butterworth low pass filter), which can provide, for example:

$$H_B(u, v) = \frac{1}{1 + (D(u, v)/D_0)^{2n}}, \quad (7)$$

$$D(u, v) = [(u - u_0)^2 + (v - v_0)^2]^{1/2},$$

where u and v can be the coordinates in the Fourier domain, $u_0$ and $v_0$ can be the center of the filter, $D_0$ can be the cut-off frequency and n can be a positive integer. A Butterworth filter can be used because it is a low pass filter with minimal ringing artifacts induced by the shape of the cutting edge owing to the Gibbs phenomenon. Then the product of the Fourier transform of the speckle pattern and the Butterworth filter can be Fourier transformed back to spatial domain to reconstruct the speckle patterns.

Figure 26B:
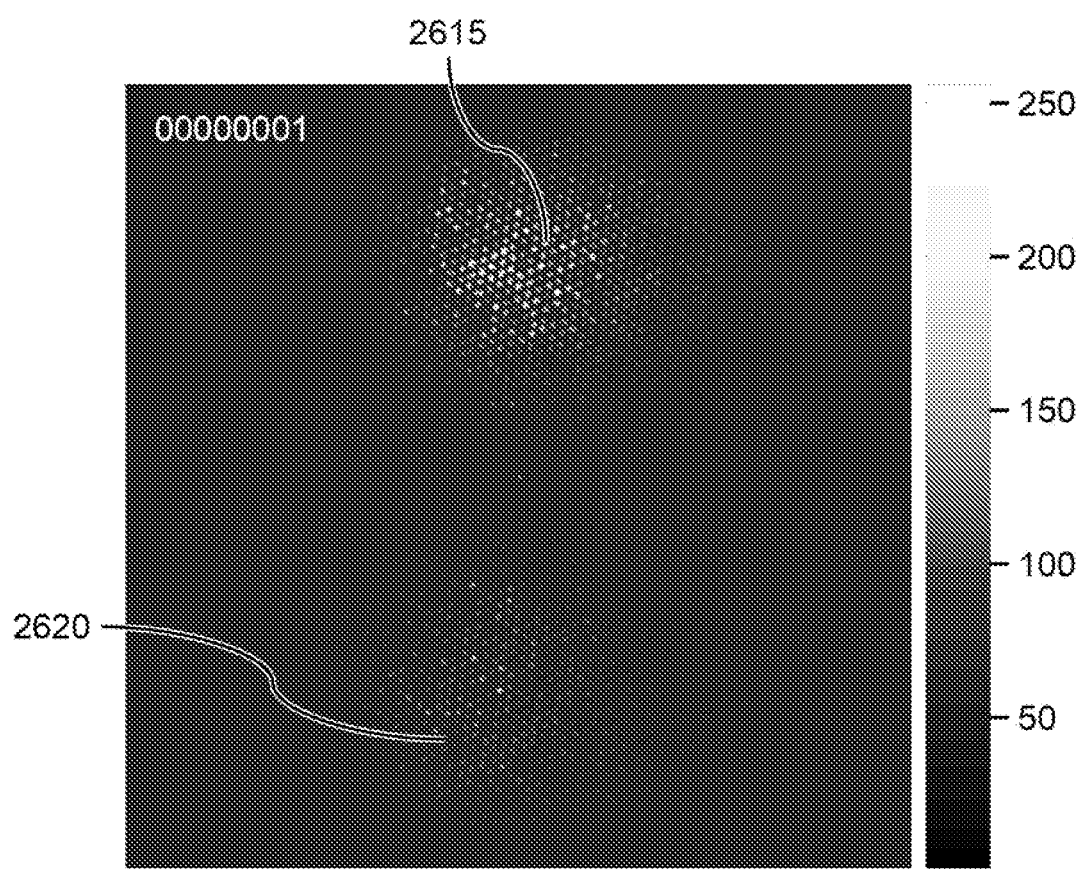
FIGS. 26B and 26C are exemplary recorded raw speckle images and its Fourier transform according to an exemplary embodiment of the present disclosure.
Figure 26C:
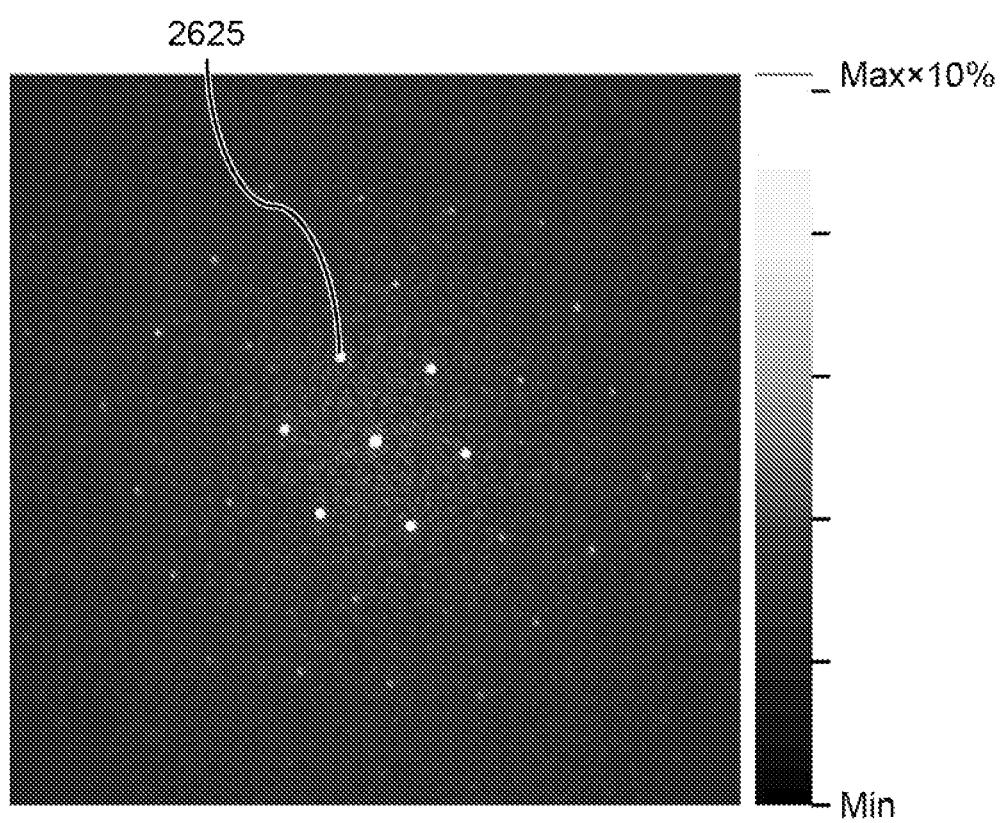
Figure 26D:
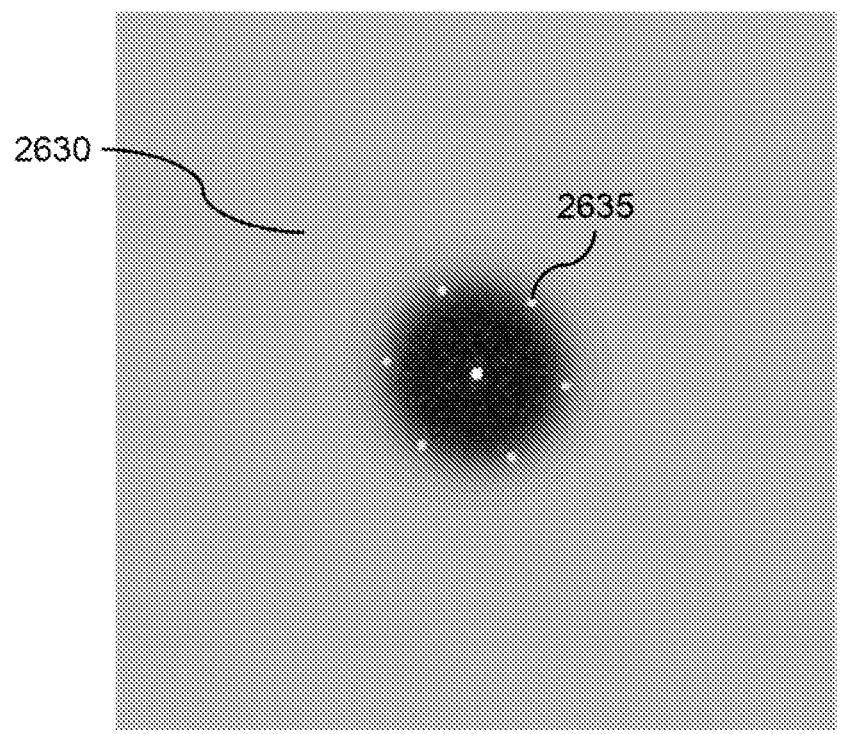
FIG. 26D is an exemplary image of a Fourier transformed speckle pattern superposed by a Butterworth filter according to an exemplary embodiment of the present disclosure.

FIG. 26B illustrates a raw speckle images obtained by an exemplary ILSI catheter from a coronary phantom. Areas 2615 and 2620 are the speckle patterns reflected from the two opposite area in the phantom. The honeycomb-like pixelation artifact can be easily seen in the FIG. 26B. FIG. 26C shows the Fourier transform of the raw image. The hexagonal pattern 2625 of the local maximums in FIG. 26C can be due to the hexagonal assembled optical fiber cores. In FIG. 26D the Fourier transform is superposed by a Butterworth filter. The filter cutoff frequency can be equal to the spatial frequency of the fiber cores. Area 2630 gray area is the rejected high frequency area by the low pass filter. The 6 first order hexagonal arranged dots 2635 are at the cutoff region of the low pass filter. If the filter cutoff frequency is even smaller, the entire periodic pattern can be filtered out such that the pixelation artifact can be removed.

Exemplary Speckle Size Smaller Than Core to Core Spacing

Figure 27A:
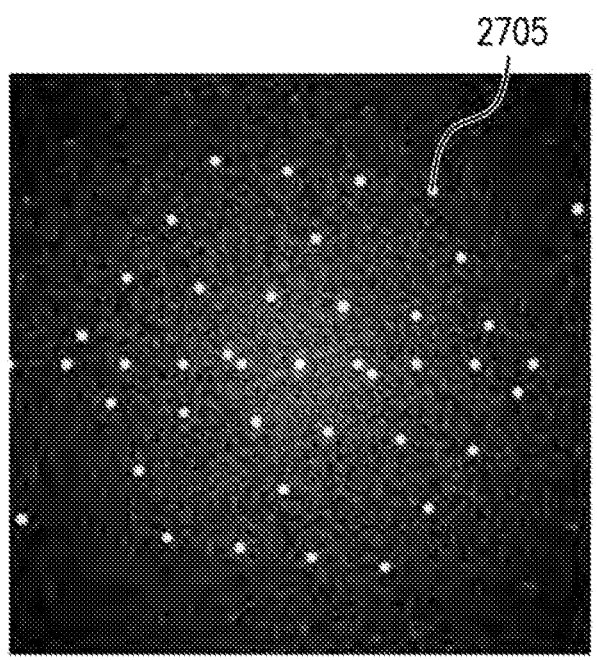
FIGS. 27A and 27B are an exemplary image and its corresponding exemplary graph illustrating the notch filter according to an exemplary embodiment of the present disclosure.
Figure 27B:
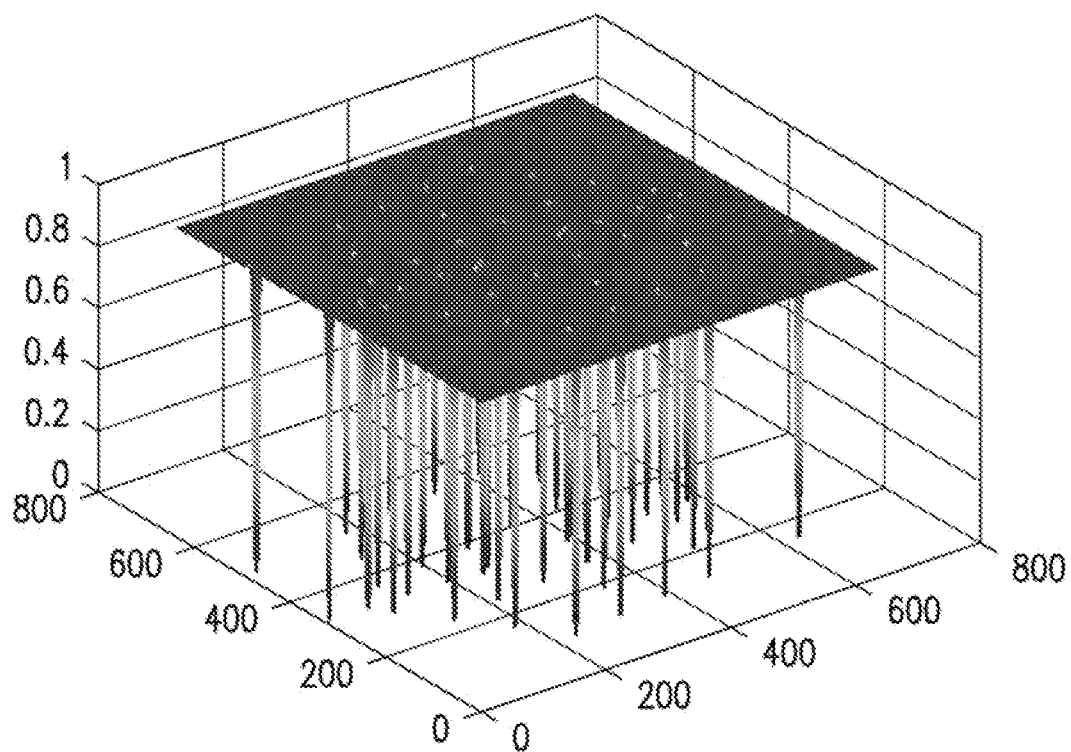
Figure 27C:
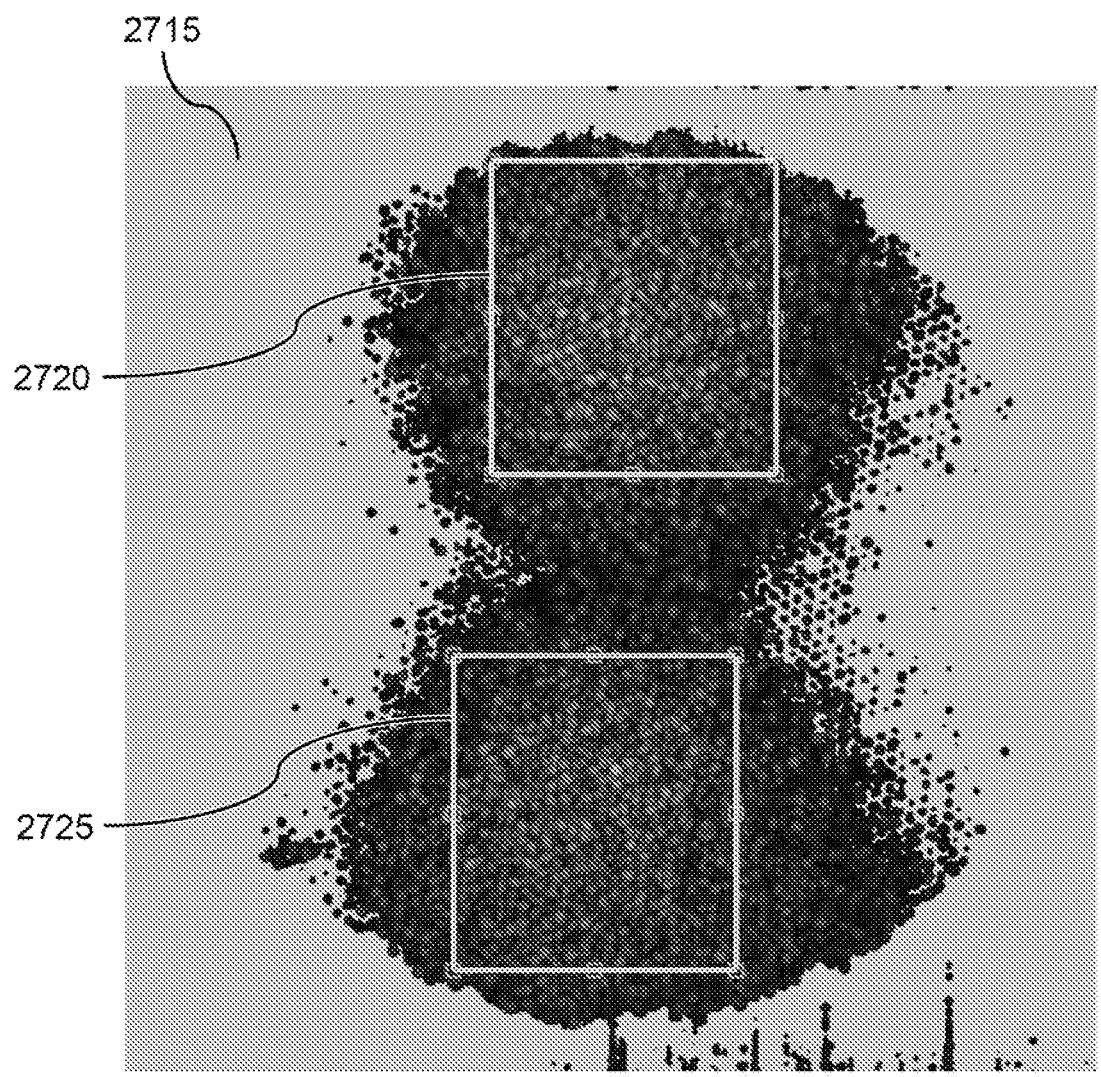
FIG. 27C is an exemplary image that utilizes the notch filter of FIG. 27B.
Figure 30A:
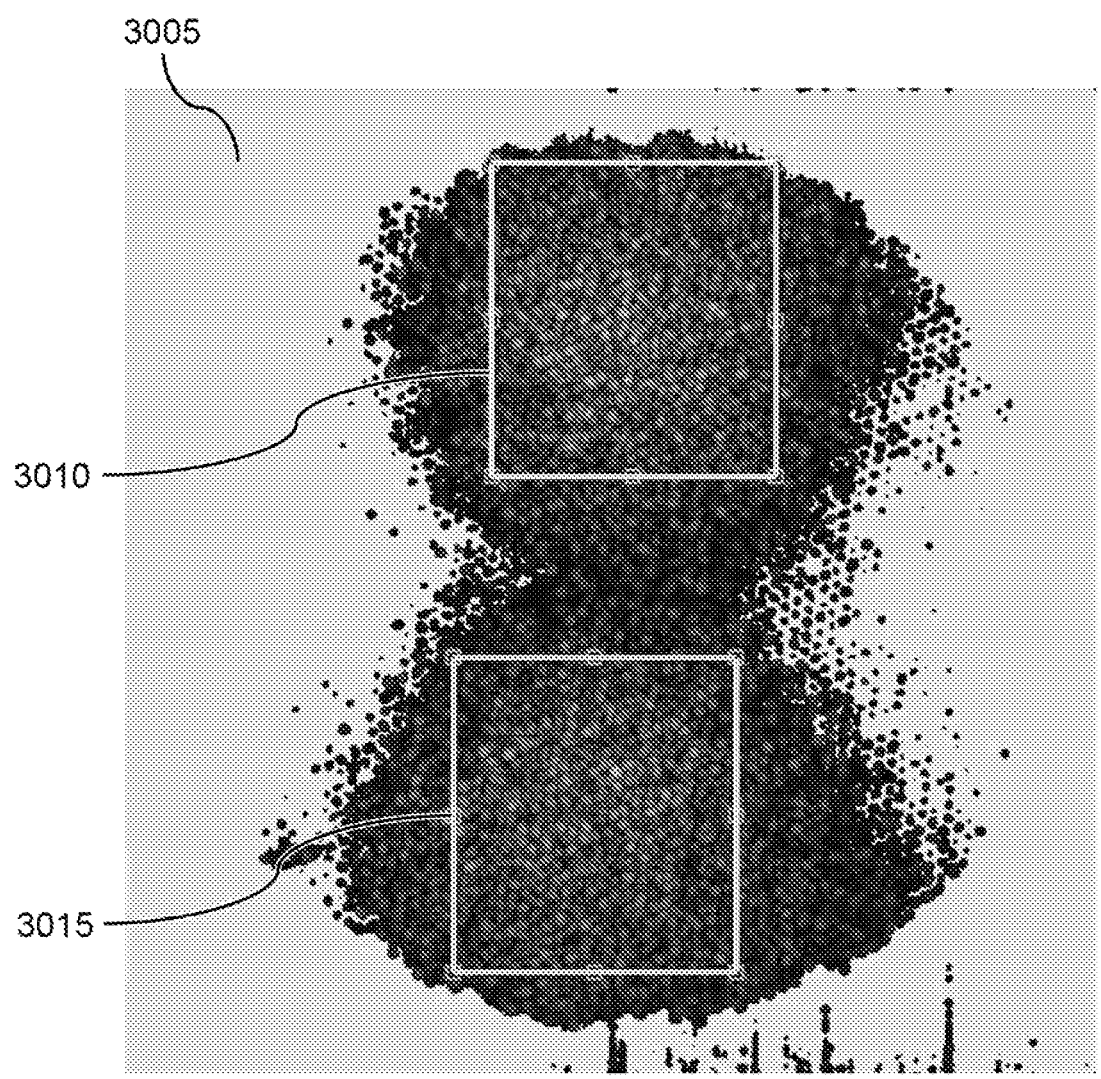
FIG. 30A is an exemplary image of an exemplary speckle pattern with pixelation artifact removed according to an exemplary embodiment of the present disclosure.

For the speckle patterns with speckle size smaller than core spacing, the spatial frequencies of the speckle pattern can be higher than that of the hexagonal pattern of fibers. Thus, simply applying the low pass filter can also remove the high frequency components of the original speckle patterns. The reconstructed speckle image can also be heavily blurred due to loss of high frequency information. A notch band-rejected filter can be applied for selectively eliminating hexagonal pattern in the Fourier domain. (See e.g., Reference 126). A notch reject filter can be formed as the product of multiple Butterworth band-reject filters whose centers are the centers of hexagonal bright spots in the Fourier domain. The notch filter $H_{NF}$ can be designed as, for example:

$$H_{NF}(u, v) = \prod_{k=1}^{N} H_k(u, v) \tag{8}$$

$$H_k(u, v) = 1 - \frac{1}{1 + (D_k(u, v)/D_0)^{2n}},$$

$$D_k(u, v) = \left[(u - u_k)^2 + (v - v_k)^2\right]^{1/2},$$

where $u_k$ and $v_k$ can be the center of the kth bright spot in the Fourier domain and $\pi$ can be the multiplication symbol. An example of the notch filter is shown in FIGS. 27A and 27B. As shown in FIG. 27A, hexagonal arranged maximums of the Fourier transform of the raw speckle image can be covered by dots 2705. The periodic dots 2705 in FIG. 27A are the rejected areas of the notch filter. A 3D view of the exemplary notch filter is shown in FIG. 27B. After the notch filter can be applied, the pixelation artifact can be removed. However, the reconstructed speckle patterns can contain the components whose spatial frequencies can be higher than the spatial frequencies of the original speckle patterns. To remove the unnecessary high frequency components, an additional Butterworth low pass filter can be applied to the speckle patterns retrieved by using the notch filters. The cutoff frequency of the low pass filter can be set to be larger than the spatial frequencies of the original speckle patterns. The reconstructed speckle pattern is shown in the FIG. 30A. Area 3005 of FIG. 30A can be the area where the pixel intensity can be zero. Outlined regions 3010 and 3015 are the speckle patterns that can have enough intensity to calculate their temporal statistics.

Exemplary Quantifying Spatial-Temporal Fluctuations of Speckle

Exemplary Temporal and Spatial Normalization of Speckle Patterns

Figure 28A:
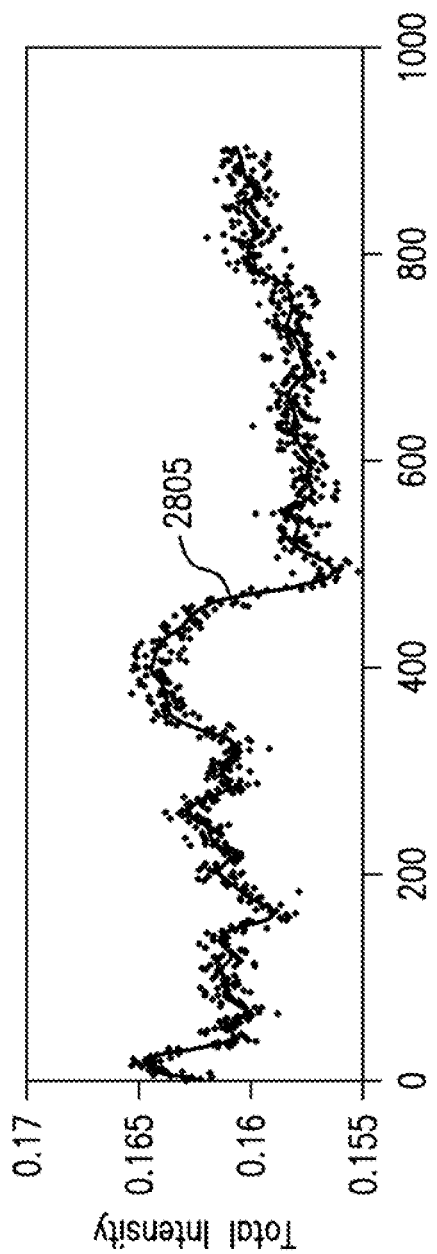
FIGS. 28A and 28B are exemplary graphs illustrating the temporal response of the total intensity of speckle patterns according to an exemplary embodiment of the present disclosure.
Figure 28B:
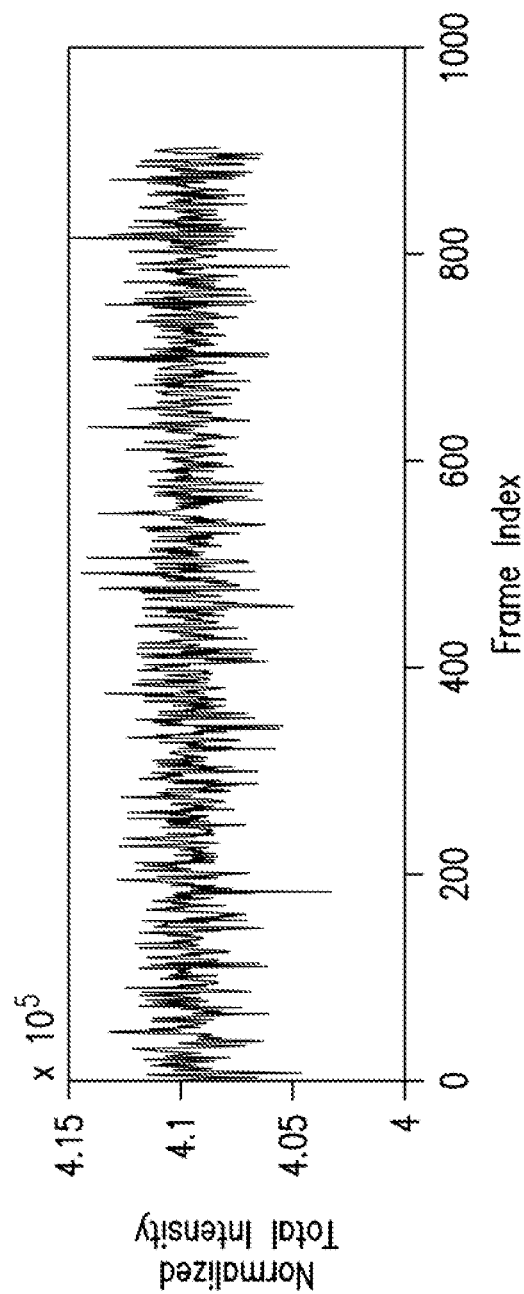

In addition to the Brownian motion of light scattering particles, various other effects, such as the fluctuations of output power of laser source, can also cause the fluctuations of speckle intensity. In order to precisely measure the rate of speckle intensity, temporal fluctuations due to the motion of light scattering, the intensity of each pixel can be divided by the spatially averaged intensity of the corresponding frame. The averaged intensity for each frame can be calculated by averaging the intensity over all pixels. The averaged intensity can also be temporally smoothed to remove the random noise. FIG. 28A shows the variation of the total intensity of the speckles with time. Line 2805 represents the smoothed total intensity. FIG. 28B shows the same total intensity over the imaging time after the pixel intensity is divided by the smoothed average intensity.

Figure 29:
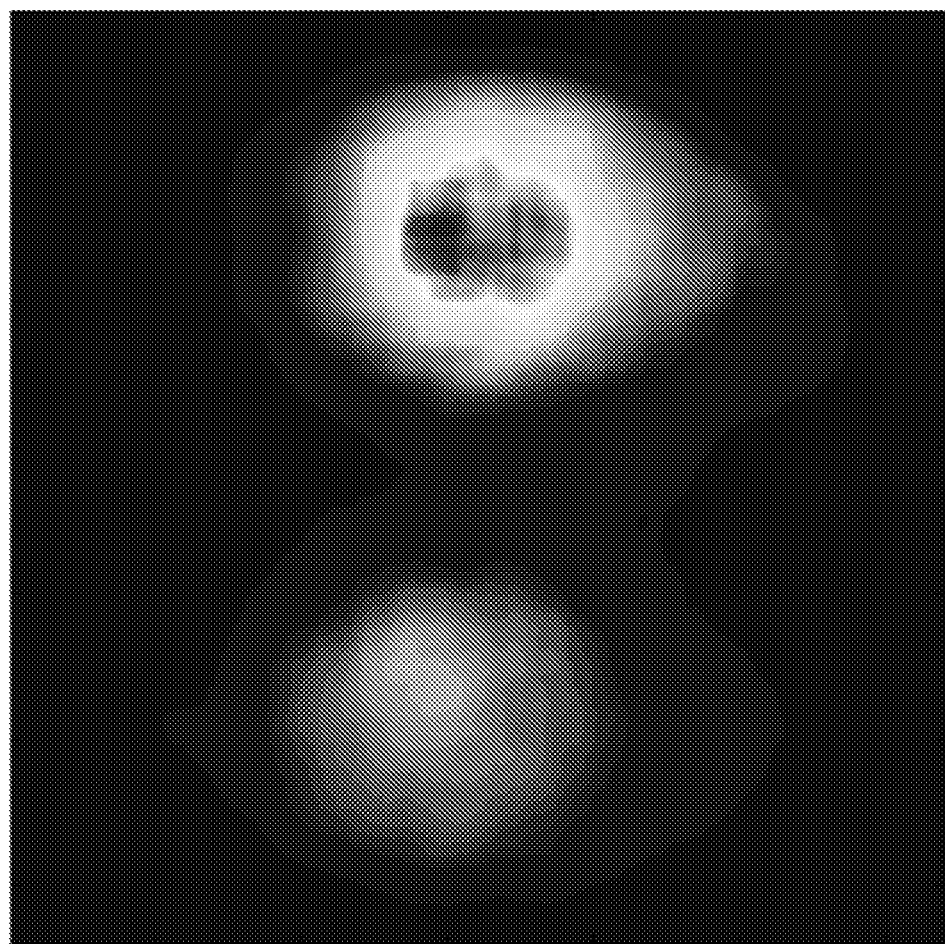
FIG. 29 is an exemplary colormap illustrating the spatially smoothed speckle pattern average over time according to an exemplary embodiment of the present disclosure.

To construct the 2D maps of the viscoelasticity of vessel walls, the spatial variation of speckle intensity due to the spatial profile of the illumination light can also affect the precision of the measurement of the speckle fluctuation rate. This can be because the statistics of speckle fluctuations can be dominated by the pixels with high intensity. Thus, the pixel with strong intensity can have more weight than the pixel with low intensity in calculating the statistics of speckle fluctuations. To remove this effect, the averaged speckle patterns over all frames can be calculated. Then the averaged speckle pattern can be spatially smoothed to remove the residual granular patterns of speckles. A spatially smoothed speckle pattern average over frame sequence is shown in FIG. 29. The intensity of each pixel can be divided by the corresponding pixel intensity of the spatially smoothed speckle pattern average over imaging time. Therefore, all the pixels can equally contribute to the calculation of the temporal statistics of speckle fluctuations.

Exemplary Speckle Intensity Autocorrelation

In order to characterize the rate of speckle temporal fluctuations and further map the viscoelastic properties of vessel walls, the temporal autocorrelation of the speckle intensities $g_2(\Delta t)$ can be calculated as, for example:

$$g_2(\Delta t) = \left\langle \frac{\langle I(t)I(t+\Delta t) \rangle_{pixel}}{\sqrt{\langle I(t)^2 \rangle} \sqrt{\langle I(t+\Delta t)^2 \rangle_{pixel}}} \right\rangle_t \tag{9}$$

where $I(t)$ and $I(t+\Delta t)$ can be the pixel intensities at times t and $t+\Delta t$, and $\langle \rangle_{pixels}$ and $\langle \rangle_t$ can indicate spatial and temporal averaging over all the pixels and over the imaging time respectively. However the direct light reflection from the outer sheath and/or other stray light in the ILSI catheter can lead to the constant background which can introduce erroneous speckle intensity correlation and the high plateau level of $g2(\Delta t)$ curve. To resolve this issue, the autocovariance (see e.g., Reference 127) of the speckle patterns $g2(\Delta t)$ can be calculated, where, for example:

$$C(\Delta t) = \left\langle \frac{\langle (I(t) - \langle I(t) \rangle_{pixel})(I(t+\Delta t) - \langle I(t+\Delta t) \rangle_{pixel}) \rangle_{pixel}}{\sqrt{\langle (I(t) - \langle I(t) \rangle_{pixel})^2 \rangle} \sqrt{\langle (I(t+\Delta t) - \langle I(t+\Delta t) \rangle_{pixel})^2 \rangle_{pixel}}} \right\rangle_t \tag{10}$$

$C(\Delta t)$ can determine the correlation between the fluctuations around average of the intensity. $C(\Delta t)$ can calculate the correlation between the intensity fluctuations around its ensemble average instead of between the intensity itself in g2(Δt). Because the intensity can include both the speckle intensity and the intensity of the background, if the background light cannot be neglected, the constant background between the intensity can lead to imprecise g2(Δt). Since the fluctuations of the intensity can come from the time-varying speckle, the correlation between the intensity fluctuations can more precisely measure the rate of the speckle temporal fluctuations. At the end, the g2(Δt) or C(Δt) can be fitted to an exponential function $f(\alpha t)=a*\exp(-t\Delta/\tau)+c$ where t can be the time, the fitting parameter τ can be the decay rate of the speckle correlation functions, a and c are the other fitting parameters. τ can also be termed as time constant. This exemplary process can be repeated to calculate spatial and temporal speckle fluctuations from all facets of the omni-directional mirror incorporated in the exemplary ILSI catheter.

Exemplary Time Constant Mapping and Visualization

Figure 30B:
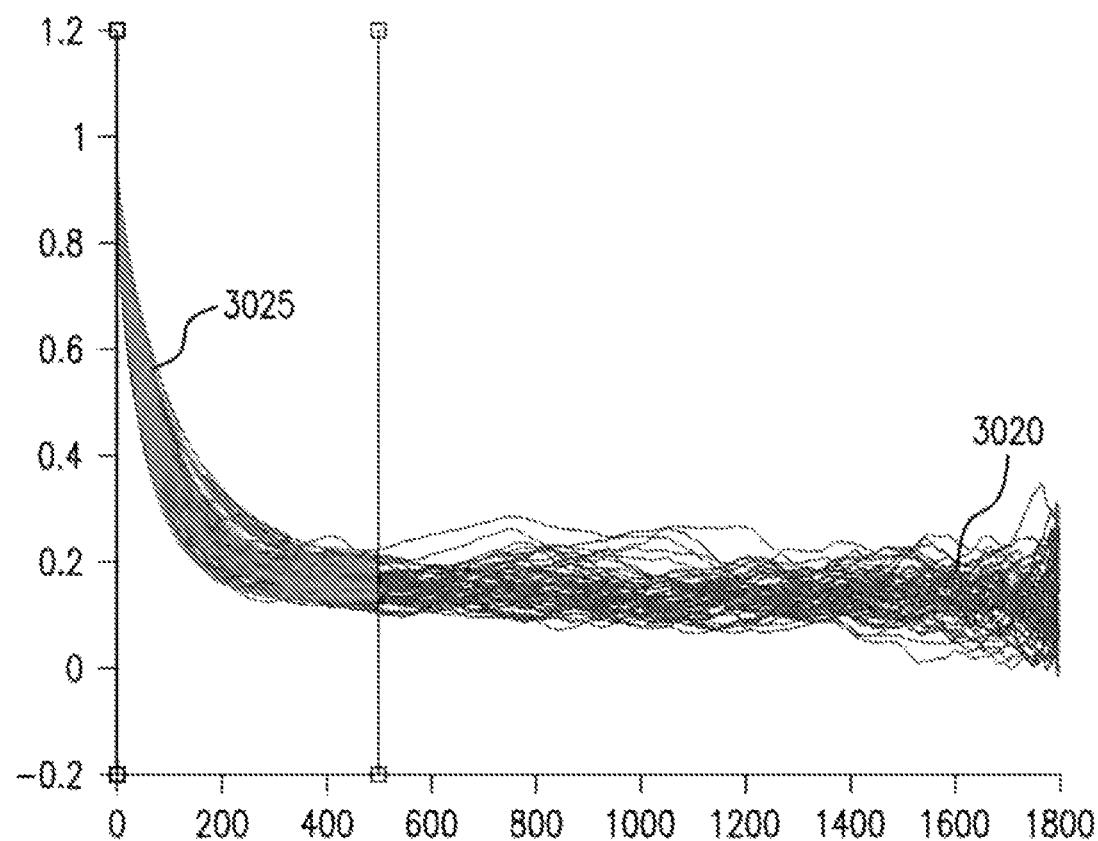
FIG. 30B is an exemplary graph illustrating the autocovariance curves of speckles within small windows according to an exemplary embodiment of the present disclosure.

To construct 2D maps of the viscoelasticity of tissues, whole imaging area can be divided, as shown in FIG. 27A, into multiple small windows (e.g., 40 by 40 pixel windows). The autocorrelation, or the autocovariance of the speckles within each window can be calculated similar to the above. Each window can have an approximately 50% area overlapped with its 4 neighbors (e.g., top, bottom, left and right neighbors). The different C(Δt) curves for different small windows in the region outlined by area 2720 in FIG. 27A are shown in FIG. 30B. Each curves 3020 is a C(Δ(a curves s IG. 27A r Each curve 3025 is the exponential fit to the corresponding blue C(Δ(the ex. Then, the time constants for all windows can be retrieved from the exponential fit. The spatially discrete time constants can then be bi-linearly interpolated to construct a smooth map of the time constants.

Figure 2:
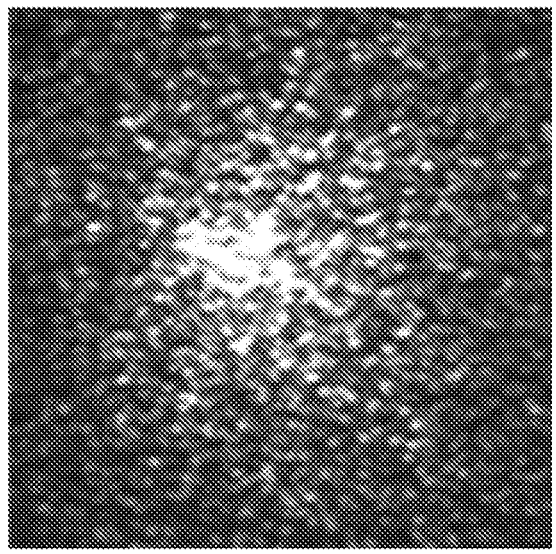
FIG. 2 is an exemplary speckle image according to an exemplary embodiment of the present disclosure.
Figure 31A:
FIG. 31A is an exemplary image of an acrylamide gel phantom in a 3D printed mold according to an exemplary embodiment of the present disclosure.
Figures 1, 31B:
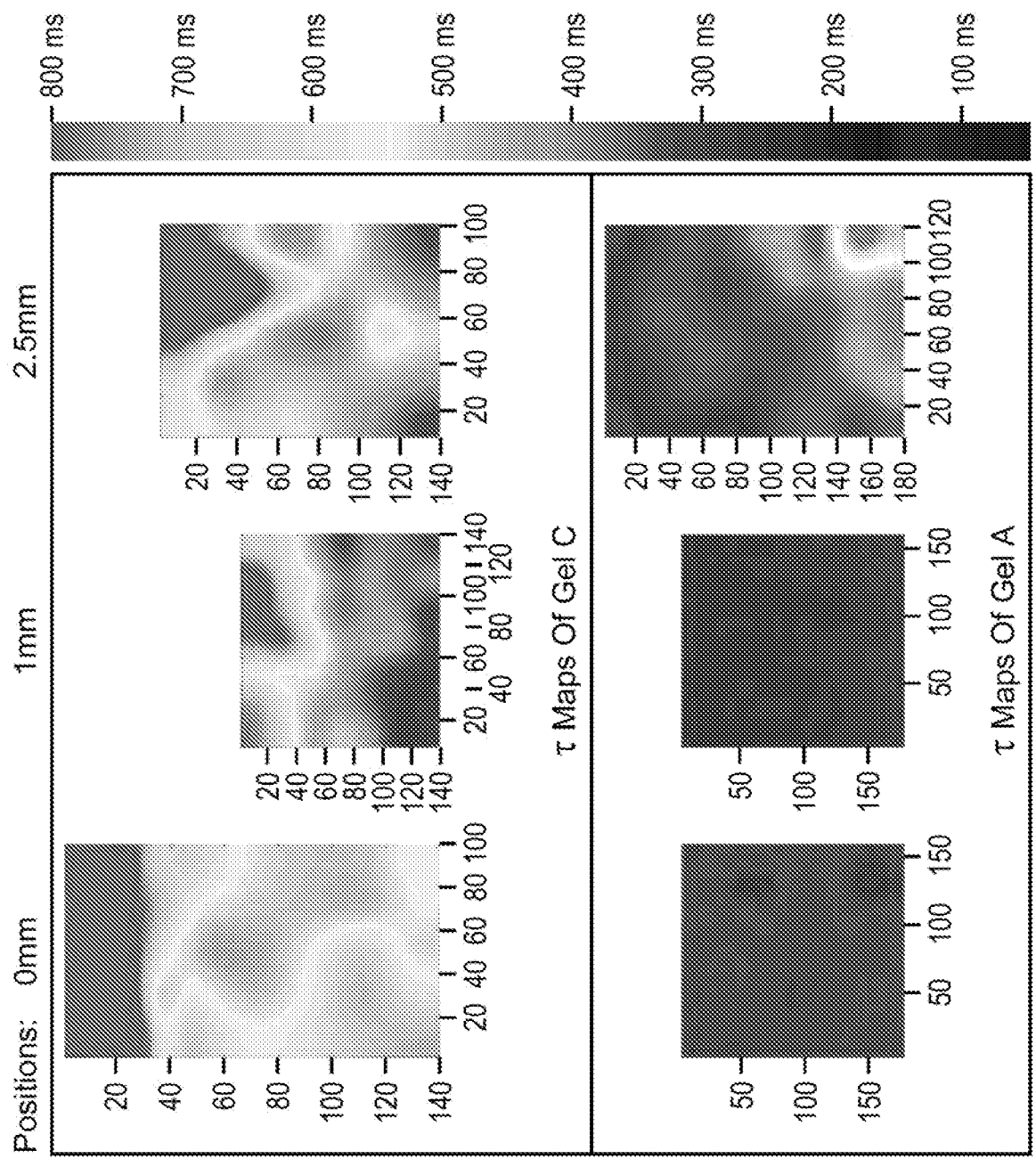
Figures 2, 31B:
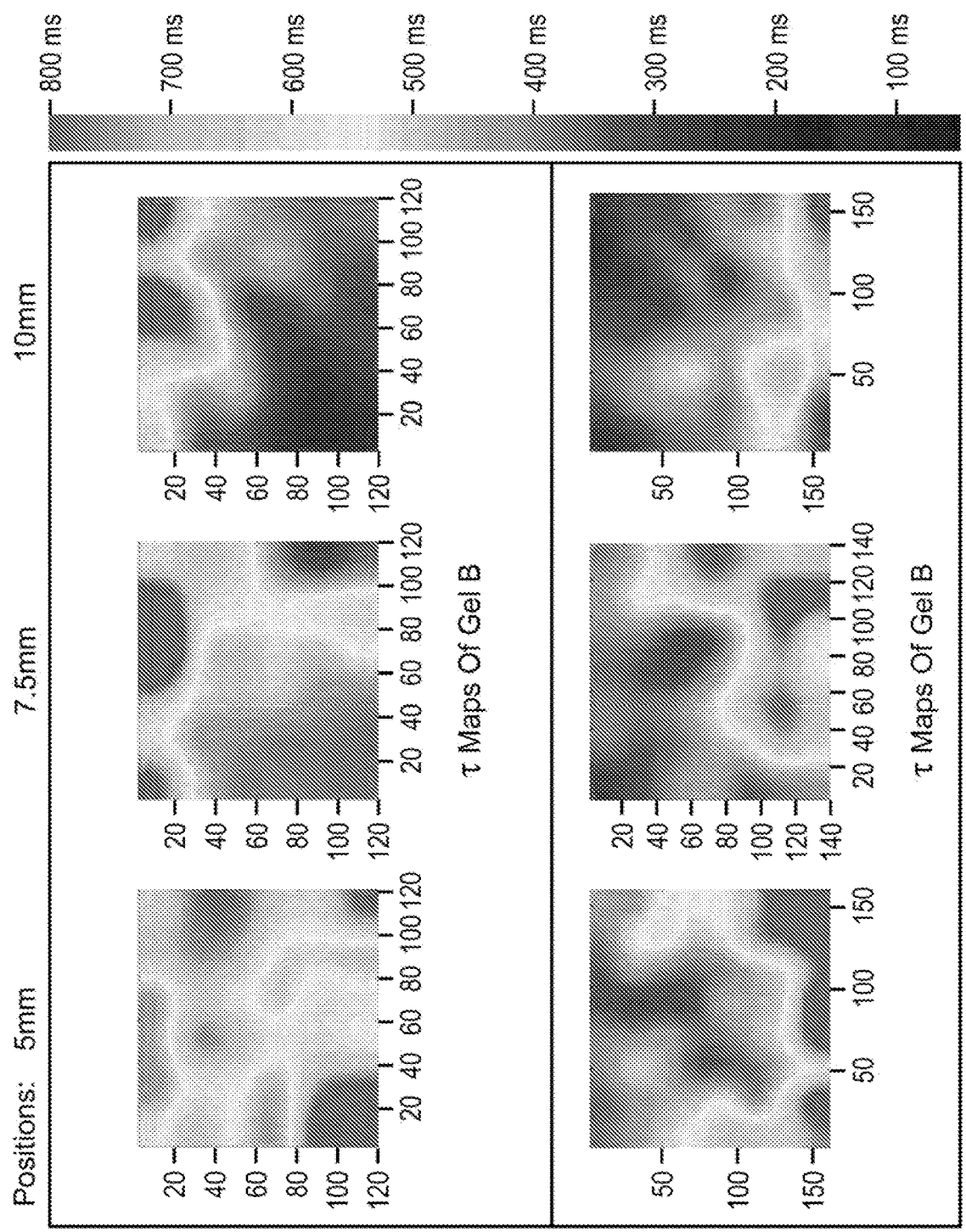

In order to test the exemplary image processing, an Acrylamide gel phantom in a 3D printed mold with 5 slots can be prepared. Each slot can be filled with different gel with different viscoelasticity. The exemplary mold and the exemplary gel filled in are shown in FIG. 31A. The gel A contains 4% Acrylamide and 0.025% of bisacrylamide. Gel B contains 5% Acrylamide and 0.025% of bisacrylamide. Gel C contains 5% Acrylamide and 0.055% of bisacrylamide. Gel A has low viscosity while gel C has high viscosity. 3 different time constant maps at 3 different positions in each slot are shown in the FIGS. 31B-1 and 31B-2. As shown in FIGS. 31B-1 and 31B-2 a big difference between the maps of the gel A and C can be observed, as well as between and between the maps of gel A and B. The differences between the 3 maps be obtained at different positions of the same gel are relatively small.

Figure 31C:
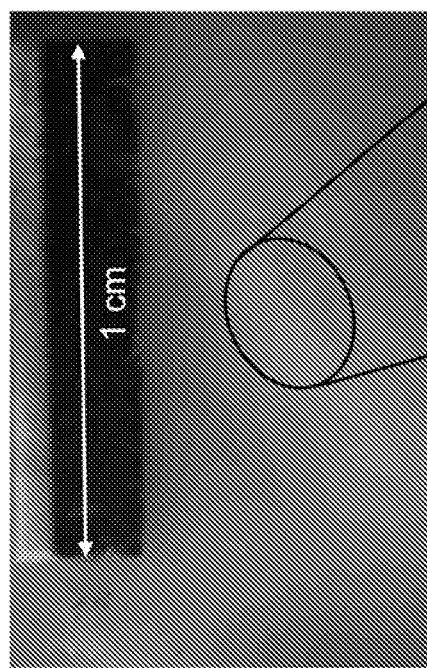
FIG. 31C is an exemplary image of swine aorta with butter injected in between the aorta layers according to an exemplary embodiment of the present disclosure.
Figure 31D:
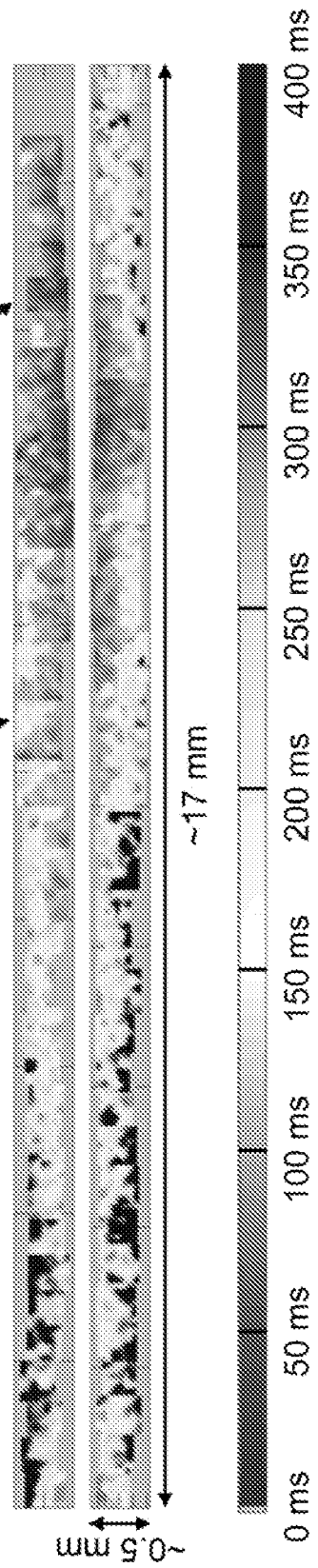
FIG. 31D is a set of the two longitudinal stitched τ maps of a tube according to an exemplary embodiment of the present disclosure.

To test the above exemplary methods, a phantom can be prepared using a small piece of swine aorta. A small amount of fat emulsion can be injected with low viscosity between layers of the aorta to mimic the lipid pool of the coronary plaques. Then, the piece of aorta can be wrapped into a small tube (e.g., approximately 3-4 mm in diameter). The swine aorta with injected fat is shown in FIG. 31C. The exemplary ILSI catheter can be inserted into the tube of aorta and the time varying speckle patterns reflected from the areas of the tube illuminated by the illumination fibers of the catheter can be recorded. At each longitudinal position along the coronary, four τ maps can be constructed. Then the catheter can be pullback a short increment to a new position and the imaging can be performed again. Then all the τ maps at different positions along the coronary can be longitudinal stitched together to form 4 long τ maps. All the τ maps can be stitched together and wrapped on the surface of a cylinder to create 2D cylindrical maps of the viscoelasticity of the coronary.

An example of wrapping a 2D τ map to form a cylindrical view of the maps is shown in FIG. 32A. It can be wrapped onto the surface of a cylinder to form a cylindrical view of the arterial viscoelasticity map (e.g., FIG. 32B). At each longitudinal position, the circumferential distribution of the τ values can be displayed by cross-sectional ring (e.g., FIG. 32C).

At each position along the coronary, four τ maps can be constructed. All the τ maps can be stitched together and wrapped on the surface of a cylinder to create 2D cylindrical maps of viscoelasticity of the coronary. An example of wrapping 2D maps to form a cylindrical view of the maps is shown in FIG. 32.

Exemplary Other Measure of the Speckle Fluctuation Rate

Time-varying speckle fields can arise from the interference of laser light scattered by the moving particles in a complex media such as tissue contain locations of zero intensity. Since both the in- and out-of-phase components of the field can vanish at the position where the intensity can be null, the phase can be undefined there. The locations with zero intensity and undefined phase can be called phase singularities, also called an optical vortex. In addition to the temporal intensity fluctuations of the speckle patterns, the Brownian motion of light scattering particles in tissue can also cause the phase of the speckle field. Therefore, the locations of the optical vortices can also change with time. Thus, the speckle fluctuation rate and the displacement of the optical vortices between speckle frames can be strongly correlated. The spatial locations of the phase singularities can be tracked over all frames of the speckle sequence. The averaged mean squared displacement of the speckle vortices can serve as another measure of the speckle fluctuation rate, can measure the viscoelasticity of tissues. AS the phase of speckle patterns may not be measured using the current ILSI catheter, an exemplary Hilbert transform can be used to generate the pseudo-field U(x,y) (see e.g., Reference 128), where, for example $$U(x,y)=I(x,y)+iH\{I(x,y)\}$$

where I(x,y) can be the speckle intensity pattern and H{I(x,y)} can be the Hilbert transform of I(x,y). Then the phase of the U(x,y) can be called the pseudo-phase φ(x,y), which can be, for example:

$$\varphi(x, y) = \tan^{-1} \frac{H\{I(x, y)\}}{I(x, y)}.$$

The temporal-spatial behavior of the optical vortices of the pseudo-phase can be similar to the behavior of the optical vortex of the real phases. (See e.g., Reference 128). The locations of the phase singularity can be obtained by calculating the phase change in a complete counterclockwise circuit around the phase singularity. If there can be a singularity within the closed circuit, the phase change can be ±2π rad. This phase singularity can be described in terms of a topological charge of ±1. Phase singularities of opposite signs can be created or annihilated in pairs with the evolvement of the speckle field.

Figure 32D:
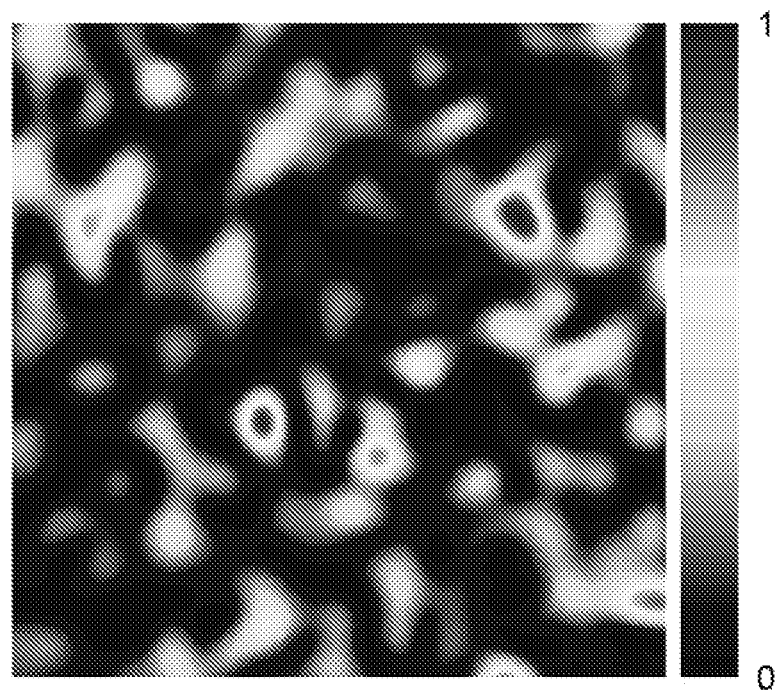
FIGS. 32D and 32E are exemplary colormaps of a speckle intensity pattern and the retrieved phase pattern using the exemplary 2D Hilbert transform according to an exemplary embodiment of the present disclosure.
Figure 32E:
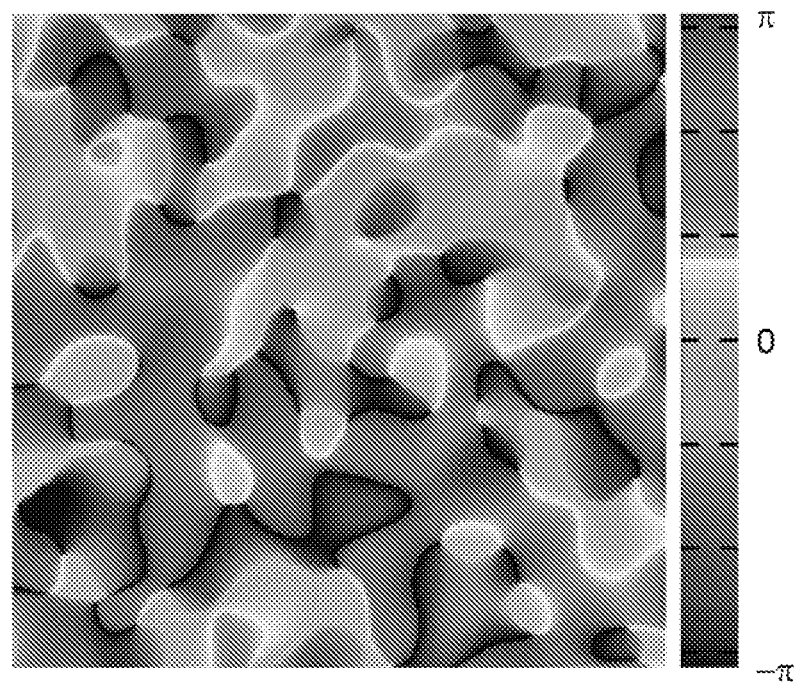
Figure 32F:
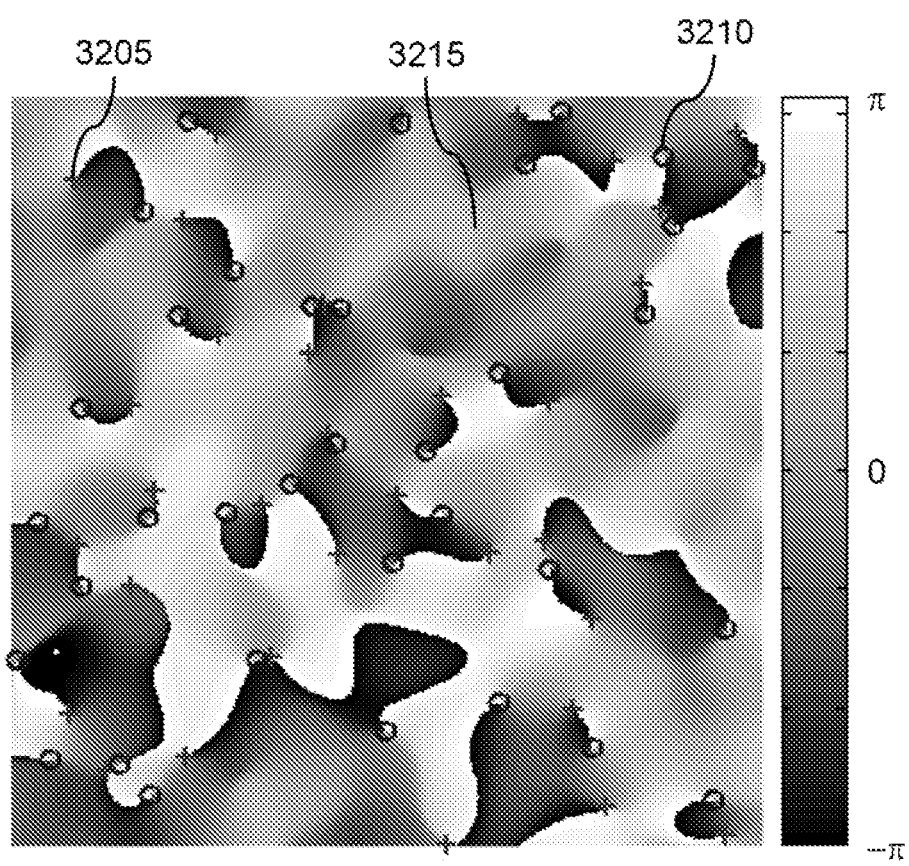
FIG. 32F is an exemplary image illustrating locations of the optical vortices according to an exemplary embodiment of the present disclosure.

FIGS. 32D and 32E show exemplary intensity pattern and the pseudo-phase of this speckle intensity patterns, respectively. The locations of phase singularities with positive and negative charge are indicated by element 3205 red "+" and element 3210 "o" in the FIG. 32F. The underground area 3215 is the pseudo-phase of the speckle pattern.

Figure 32G:
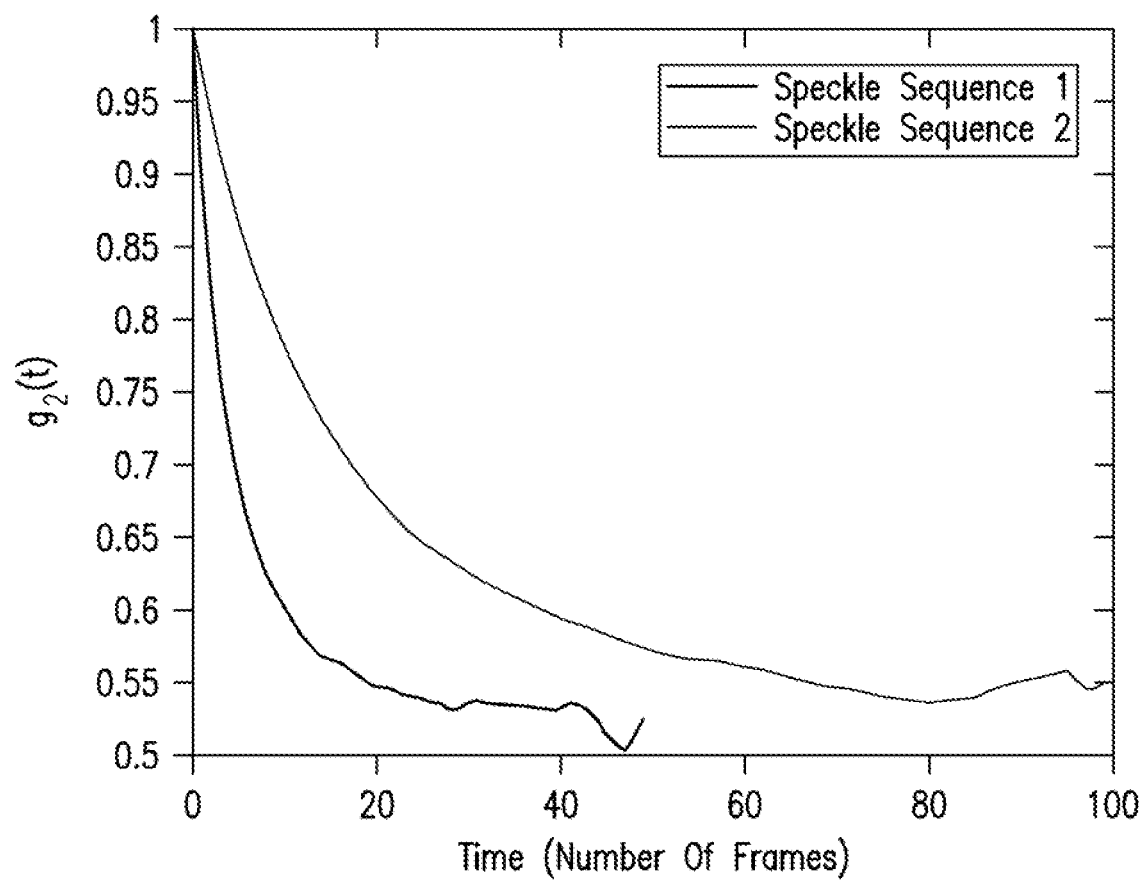
FIG. 32G is an exemplary graph illustrating speckle intensity autocorrelations for two different speckle sequence according to an exemplary embodiment of the present disclosure.
Figure 32H:
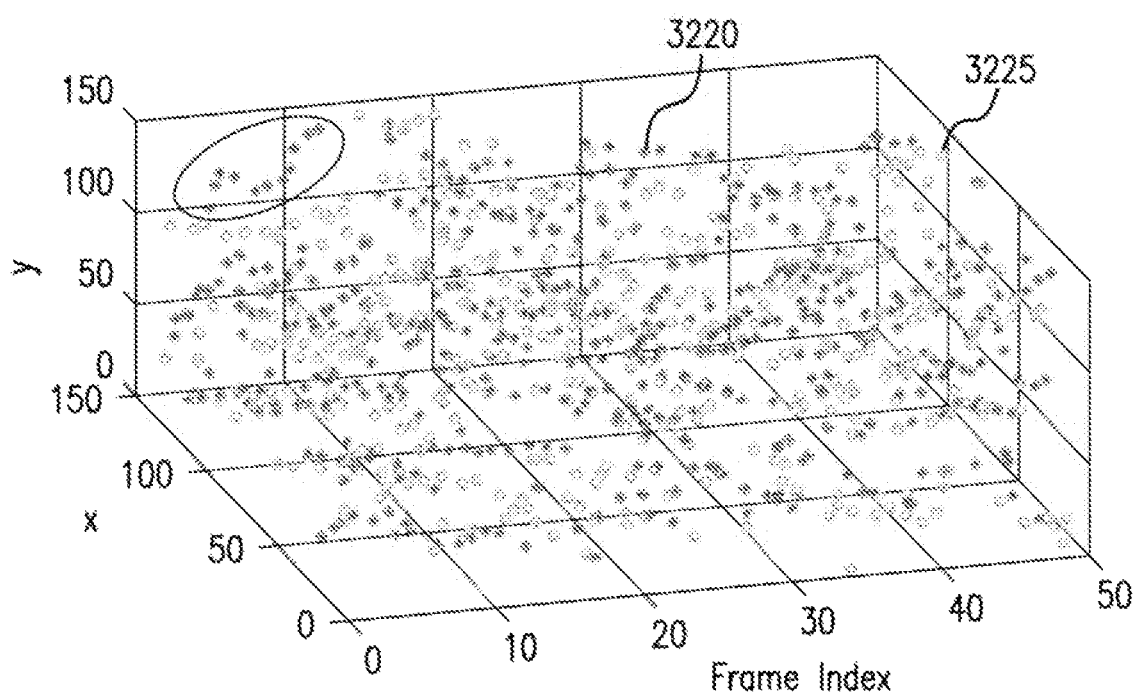
FIG. 32H is an exemplary graph illustrating the locations of the optical vortex at different speckle frames for the fast varying speckle sequence according to an exemplary embodiment of the present disclosure.
Figure 32I:
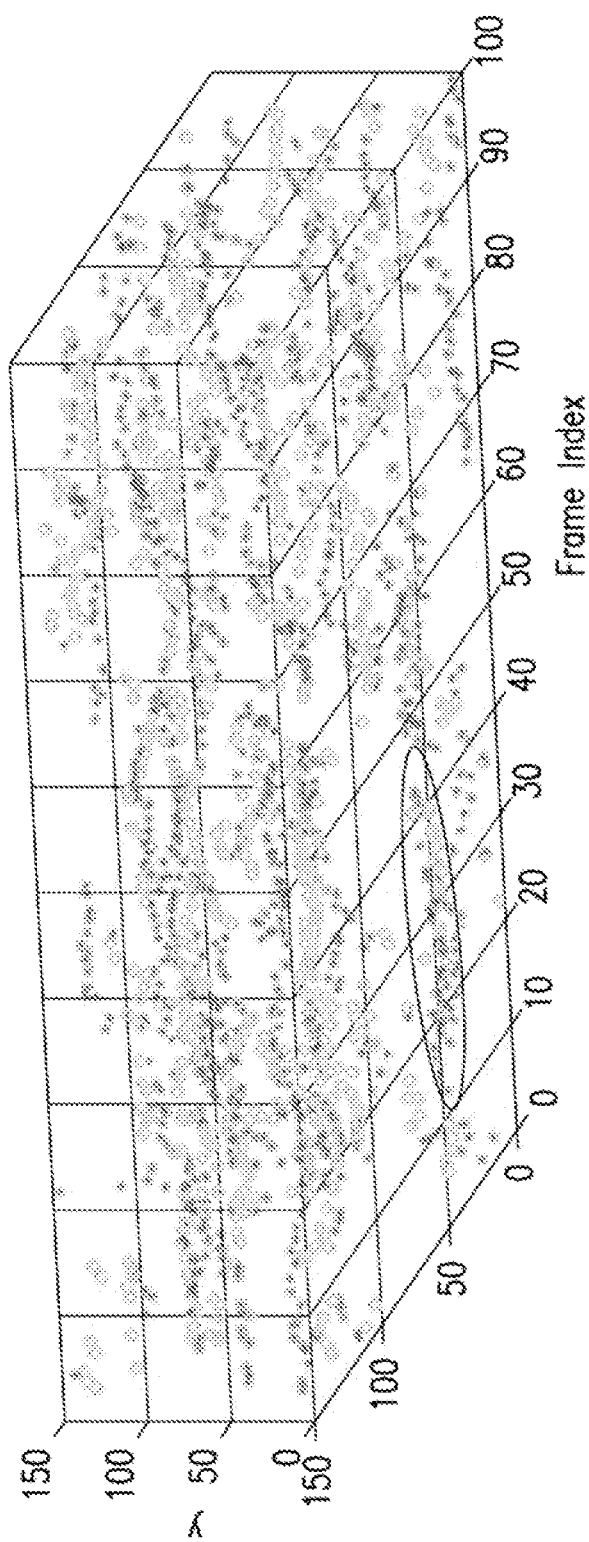
FIG. 32I is an exemplary graph illustrating the locations of the optical vortex at different speckle frames for the slow varying speckle sequence according to an exemplary embodiment of the present disclosure.

Two speckle pattern sequences with 50 and 100 frames can be selected. Their temporal autocorrelation g2(t) of the intensity patterns are shown in FIG. 32G. From FIG. 32G, it can be seen that the g2(t) curve of the speckle sequence with 50 frames can decay much faster than the g2(t) curve of the speckle sequence with 100 frames. For both sequences, their pseudo-phase can be generated, and the locations of the vortices of all frames can be determined. These locations are then plotted in FIG. 32H. The positively charged vortices are plotted as stars 3220, and the negatively charge vortices are plotted as circles 3225. The locations of each individual vortex over several frames can trace a path called a vortex trail. One example of a trail of an optical vortex of each speckle sequence is outlined in FIGS. 32H and 32I. By comparing FIGS. 32H and 32I, the trails of the vortices can be seen, and are quite long and straight in a slowly varying sequence (e.g., FIG. 32I). In the rapidly decorrelating speckle sequence (e.g., FIG. 32H), the vortices trails are shorter and tortuous. The straight and long trail can mean that the vortices stay at the same position for long time and the displacement of the vortex between two consecutive frames can be small. Therefore, the mean squared displacement of the optical vortices can be inversely related to the time constant of the autocorrelation of the speckle intensity patterns, and can serve as an additional measure of the viscoelasticity of the tissue. An advantage of utilizing the temporal-spatial behavior of the optical vortices can be that it may only a need few frames to obtain the adequate statistics of the mean squared displacement of the phase singularities. Therefore, it can greatly shorten the imaging time, while calculating the decorrelation of the speckle frames can require long imaging time that has to be few times longer than the decorrelation time of the speckles.

Exemplary Results and Discussion of Fiber Bundle Selection

Figure 21A:
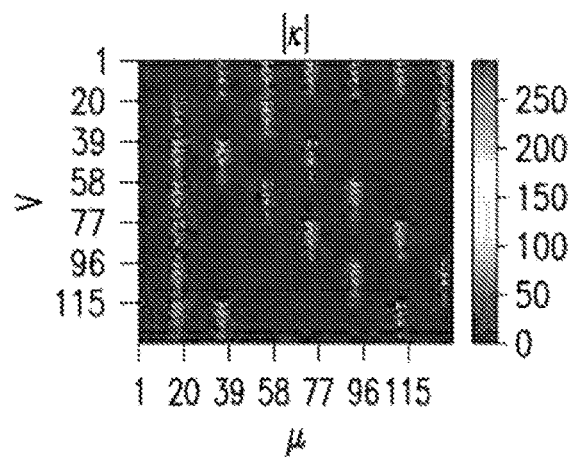
FIG. 21A is an exemplary image illustrating the amplitude of coupling coefficient x between all the 19×7 modes according to an exemplary embodiment of the present disclosure.

The coupling can be integrated between all guided modes in different individual cores of a 7-core structure with specifications of type I fiber bundle listed in Table 2 above. Since each core in this structure can support 19 guided modes at a wavelength of about 690 nm, the total number of guided fiber modes can be 7×19=133, and therefore, the dimensions of the matrices of coupling coefficient κ between all modes can be 133 by 133. The amplitudes of the mode coupling coefficients $|\kappa_{\nu\mu}|$ are shown in FIG. 21A. Here the mode index ν can run through all 133 guided modes. It is noted that the first 19 modes, which can propagate in the central fiber, can have large coupling coefficients with the higher order modes of all surrounding fibers while the coupling coefficients between the modes of each of the 6 surrounding fiber and the modes of its 3 nearest neighbors can be much larger than the coupling coefficients to the modes of further cores. Thus, the coupling coefficient of modes of each core can be dominant by the coupling to the modes of its nearest neighbors. FIGS. 21B-21F show the intensity in each core, which can be the summation of squared mode amplitudes over all guided modes in the core, which can oscillate between the central fiber and surrounding fiber with propagation distance z. As shown in FIGS. 21B-21F, the mode 1, 2, 6, 9, 10 of central fiber can initially be excited at z=0. The mode amplitudes changing with z up to 1 m which can roughly be a typical length of fiber bundles used in medical endoscopy can then be calculated.

Figure 21B:
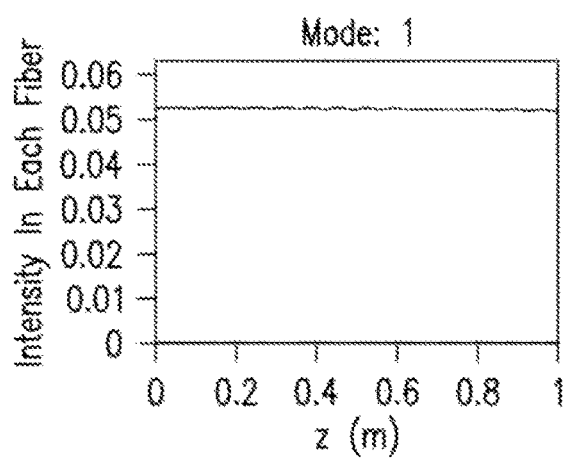
FIGS. 21B-21F are exemplary graphs illustrating the intensity of different order modes of central fiber coupled to the corresponding modes of surround fibers with propagation distance z for 1st, 2nd, 6th, 9th and 10th mode respectively according to an exemplary embodiment of the present disclosure.
Figure 21C:
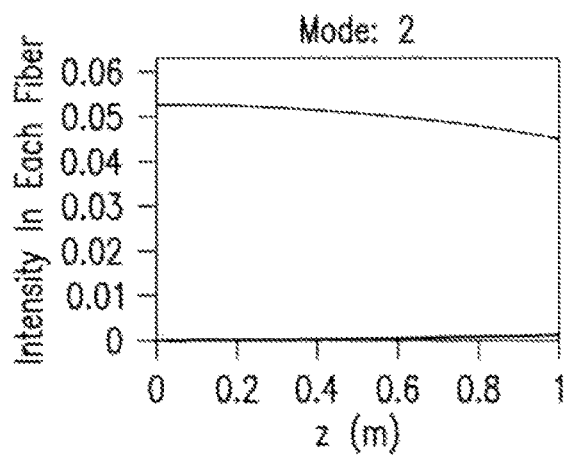
Figure 21D:
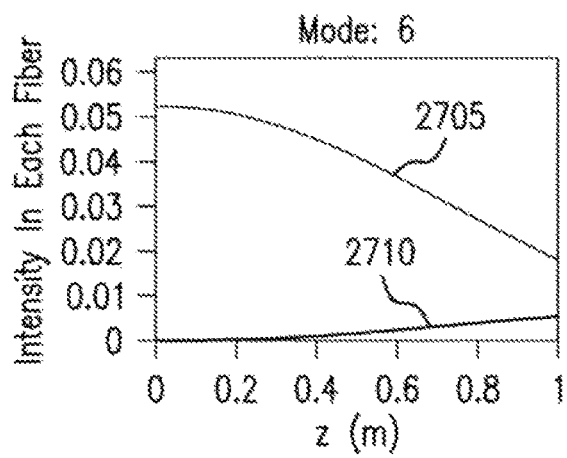
Figure 21E:
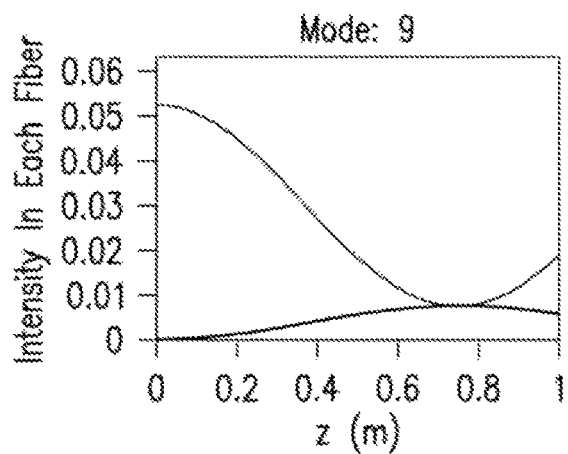
Figure 21F:
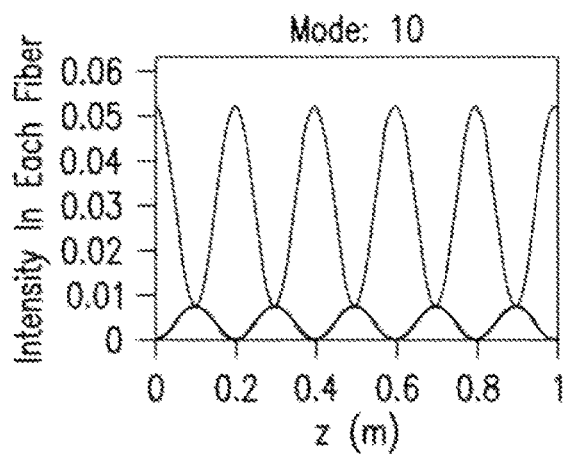
Figure 22F:
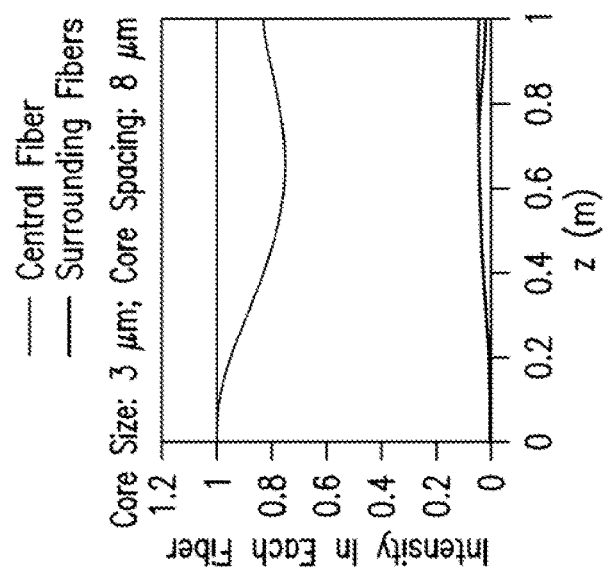
FIGS. 22D-22I are exemplary graphs illustrating that the coupling strength can increase as core size increase, core spacing decrease and NA decrease according to an exemplary embodiment of the present disclosure.
Figure 22E:
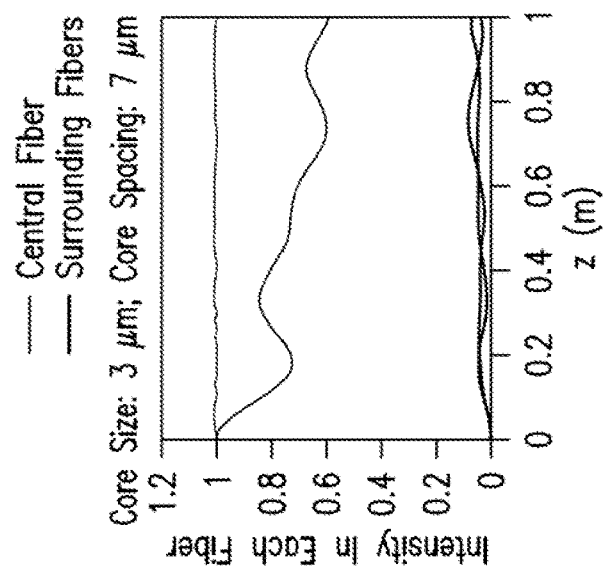
Figure 22D:
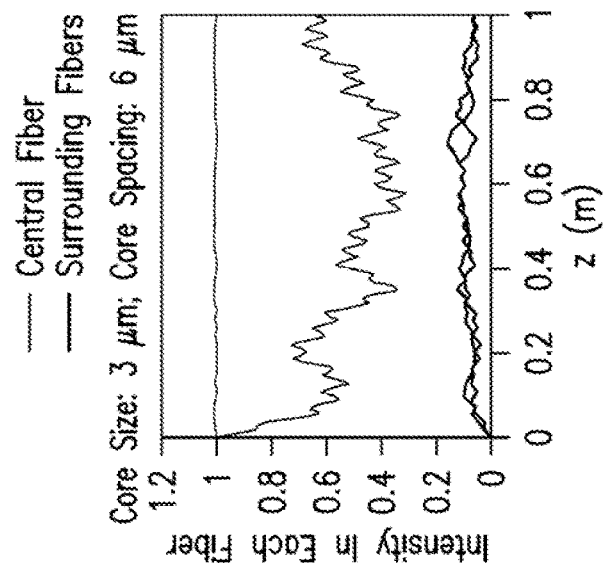
Figure 22I:
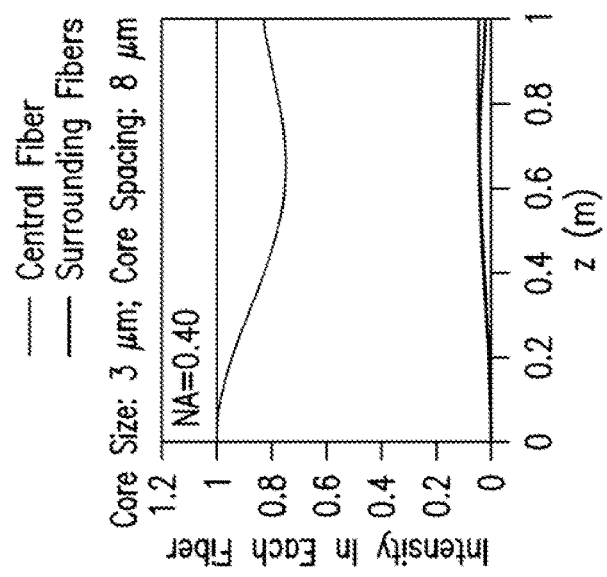
Figure 22H:
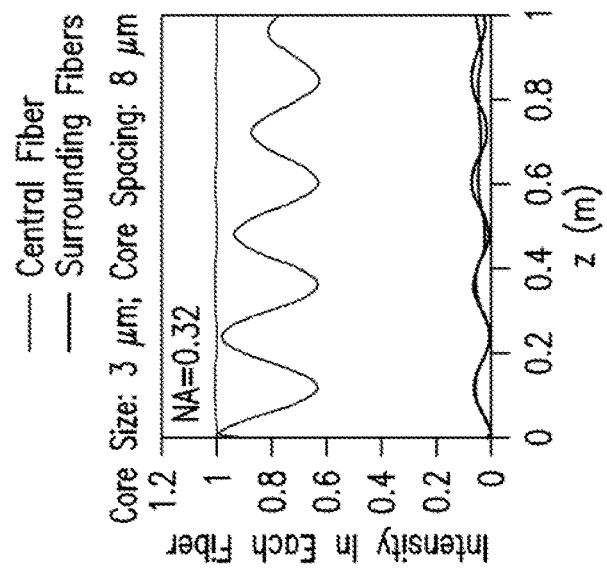
Figure 22G:
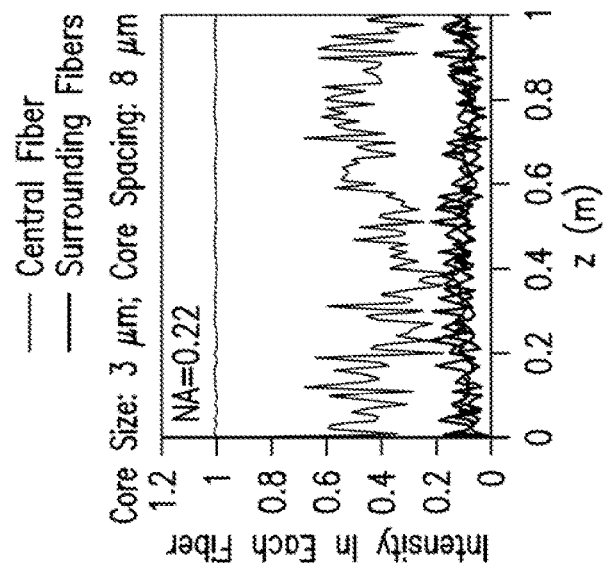

As the order of excited mode of central fiber can increase from 1 to 10 as shown in FIGS. 21B-21F, the coupling distance defined as the oscillation period of intensity along with propagation distance z becomes shorter. The intensity in central core represented by line 2105 can't couple to the surrounding cores whose intensity represented by lines 2110 when only the fundamental mode of central core can be excited as shown in FIG. 21B. While FIG. 21F shows that there can be multiple coupling distances within 1 m which can indicate strong core-to-core coupling when only mode 10 of central fiber can be initially excited. For the modes with same order of different identical cores, the difference between the propagation constant Δβ of these modes can be 0, and the coupling strength may only depend on the mode coupling coefficient between these modes with same order in each fiber. Since the fields of a higher order modes can extend more into the cladding, the overlapping of higher order mode field can be stronger, and coupling between higher order modes of identical cores can be stronger. For the modes with different order of adjacent cores, due to the difference in propagation constant, the cross order mode coupling can be neglected which can be observed in FIG. 21F. If there can be cross order mode coupling, the intensity oscillation between central and surround cores can be more complex than the simple one period oscillation shown in FIG. 21F. Thus, if the number of guided modes in each fiber can be reduced to less than 10, the coupling between cores can be suppressed.

In order to better understand the effect of different fiber bundles specifications on the coupling efficiency of all modes, the total intensity coupled from central core to surrounding cores along with propagation distance for the fiber bundles with different specifications, including core sizes, core spacings and NA, as shown in FIG. 22, can be investigated. In the exemplary calculation, the initial value of amplitudes of all guided N modes of central fiber can be set to be equal, $a1(0)=a2(0)=\ldots=aN(0)=(1/N)^{1/2}$ and the initial value of the mode amplitudes of surrounding fibers can be all set to zeros. The coupling between fibers for fiber bundles with 3 different core sizes (e.g., 2 μm, 3 μm and 4 μm), 3 different core spacings (e.g., 6 μm, 7 μm and 8 μm), and 3 different NA, (e.g., 0.22, 0.32 and 0.40) can be calculated. As shown in In FIGS. 22A-22C, coupling strength can be stronger as core sizes increase from 2 μm, 3 μm to 4 μm because the fibers can support more higher order modes whose coupling can be strong and the overlap of lower order mode can also be stronger since they can be closer when core size increases. FIGS. 22D-22F show that the large core-to-core spacing can lead to reduced coupling due to the large separation between mode fields because of the less mode field overlaps when the cores can be closer. FIGS. 22G-22I show that the larger NA indicating larger refractive index contrast between core and cladding material can lead to stronger confinement of mode fields and can reduce overlapping of modal fields of neighboring fibers.

Figure 23A:
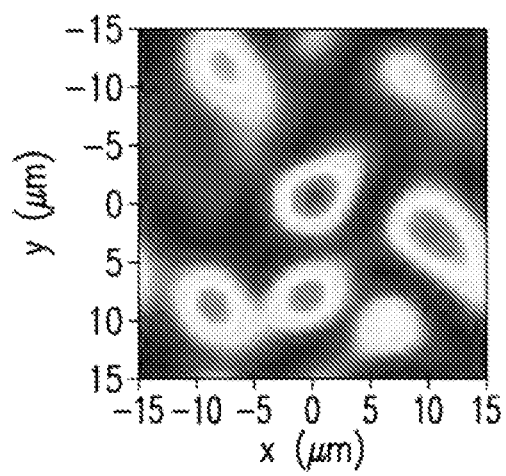
FIGS. 23A-23I are exemplary graphs and exemplary images illustrating illustrate how speckle pattern change with propagation distance due to crosstalk between neighboring cores according to an exemplary embodiment of the present disclosure.
Figure 23B:
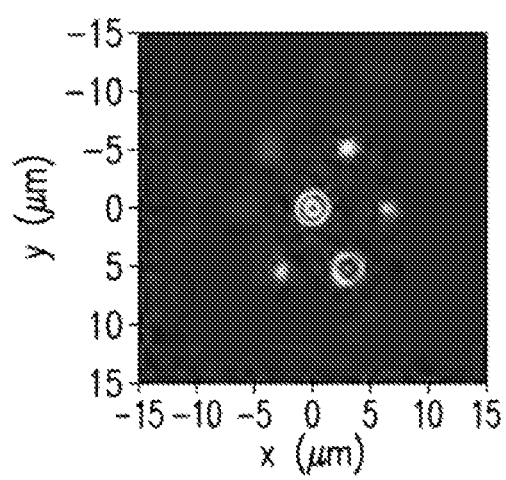
Figure 23C:
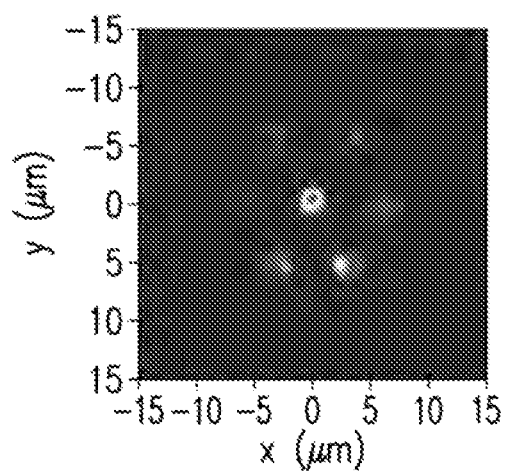
Figure 23D:
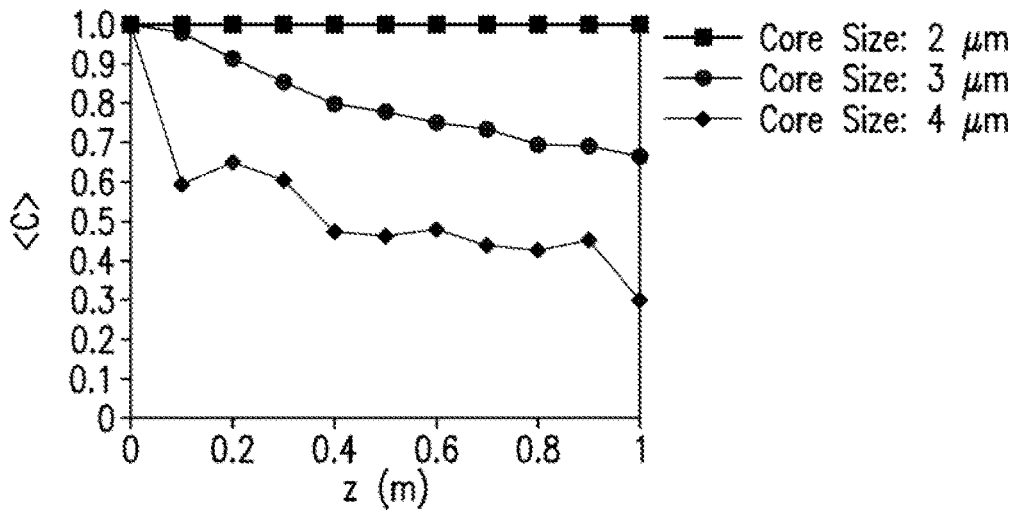
Figure 23E:
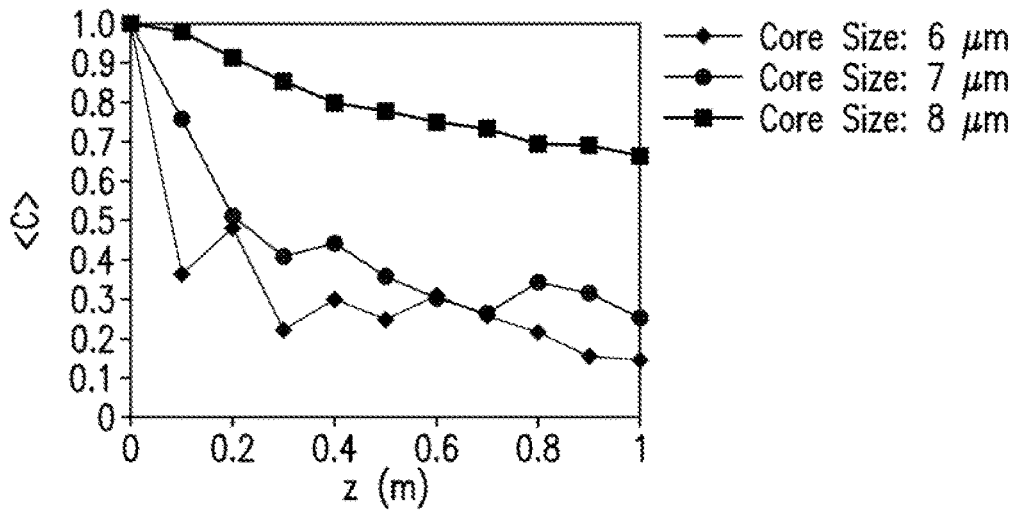
Figure 23F:
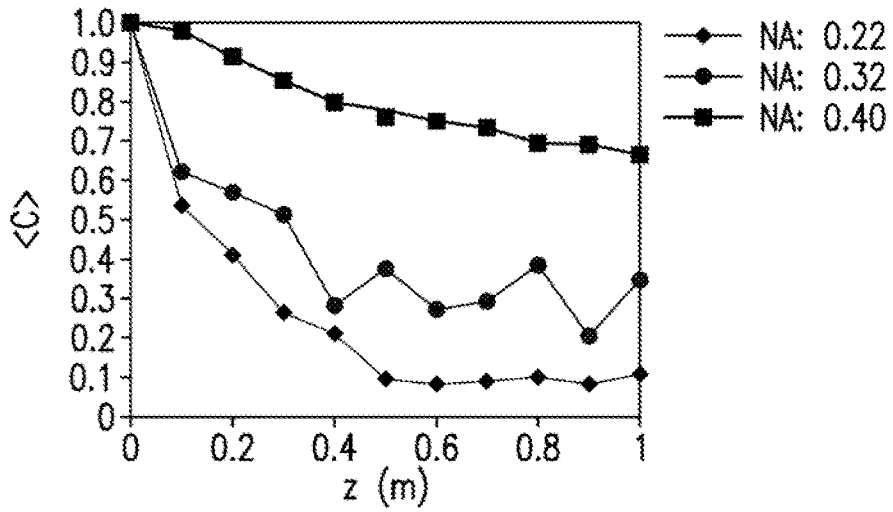
Figure 23G:
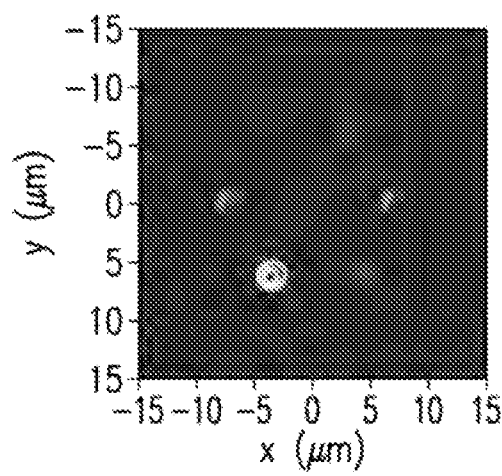
Figure 23H:
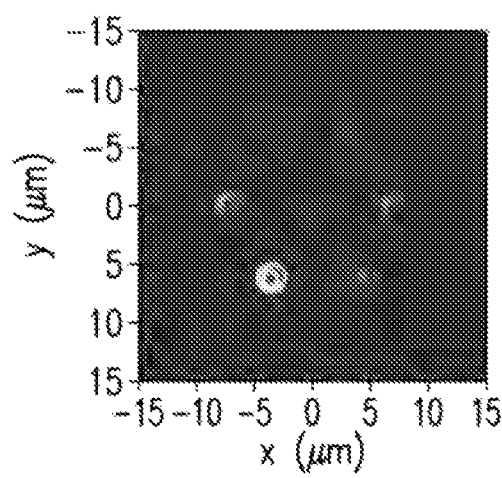
Figure 23I:
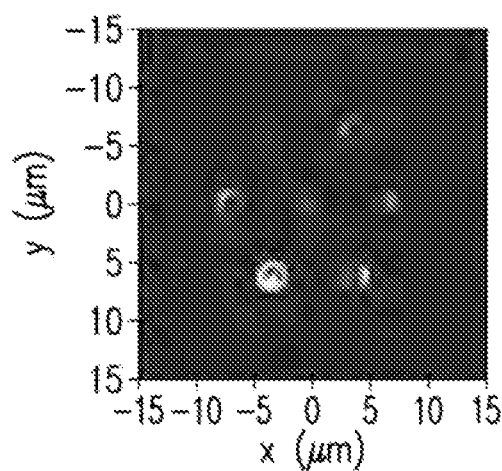

The modulation to the transmitted speckle patterns due to the core coupling is shown in FIG. 23A-23C. FIGS. 23A-23C show the numerically generated speckle patterns, the speckle patterns coupled in the fiber bundle at z=0, and speckle pattern at z=1 m for fiber bundle with 3 μm core size, 6 μm core spacing and 0.40 NA. Strong modulation of the speckle patterns can be observed from the difference of speckle patterns in FIGS. 23B and 23C. The ensemble average over 20 speckle realization of correlation function for fiber bundles with different core sizes, core spacings and NAs are shown in FIGS. 23D-23F, respectively. The large core-to-core separation, small core size and large refractive index contrast between core and cladding material can be essential to reliably transmitted speckle patterns. Based on the results shown in FIGS. 22A-22F, and 23A-23I, fiber bundles with 3 μm core size, 8 tm core spacing and 0.40 NA can have moderate crosstalk between fibers, and its specifications can be close to those commercially available, such that it can be relatively easy to manufacture. The fiber with 3 tm core size can support 9 modes to avoid strong coupling of higher order diodes. The transmitted speckle patterns at z-O, 1 and 100 cm are shown in FIGS. 23G-23I, respectively. The modulation of speckle patterns along with z can be less than the modulation of the speckle patterns shown in FIGS. 23B and 23C. It shows again that the relative large separation can help to suppress core coupling and modulation to speckle patterns. The higher NA can confine mode field in the core better, but higher NA can also increase the number of guided modes and 0.40 NA can be the highest currently available contrast of refractive index between core and cladding material of fiber bundles.

Figure 24A:
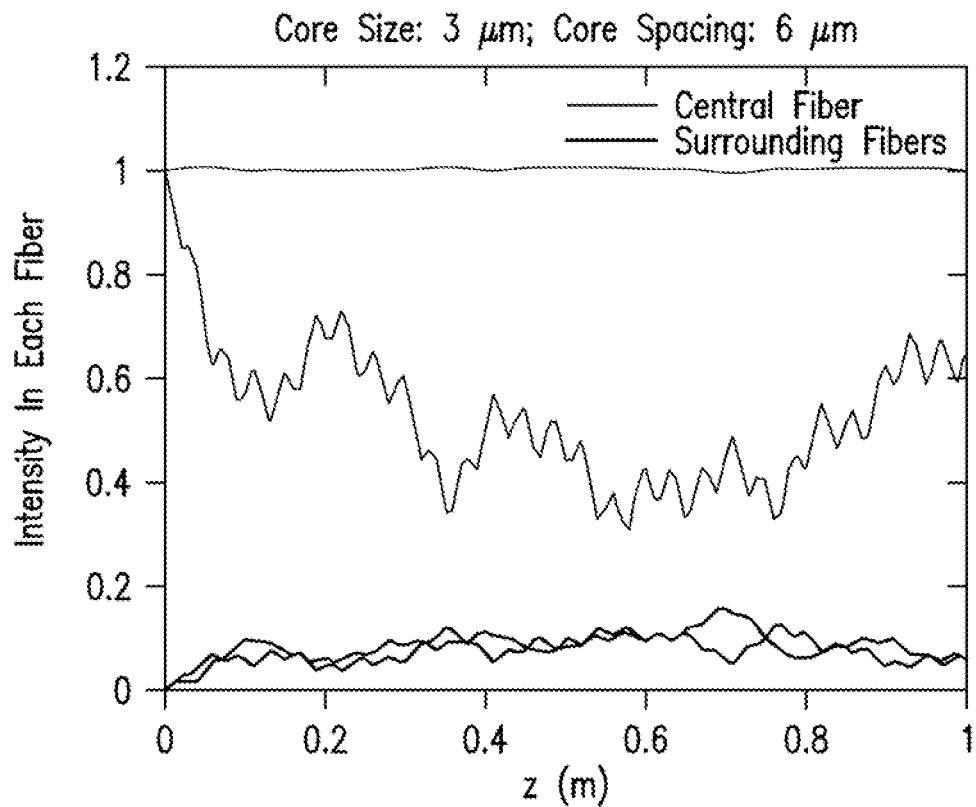
FIGS. 24A-24C are exemplary graphs illustrating the reduced change of intensity in each fiber of optical fiber bundles according to an exemplary embodiment of the present disclosure.
Figure 24B:
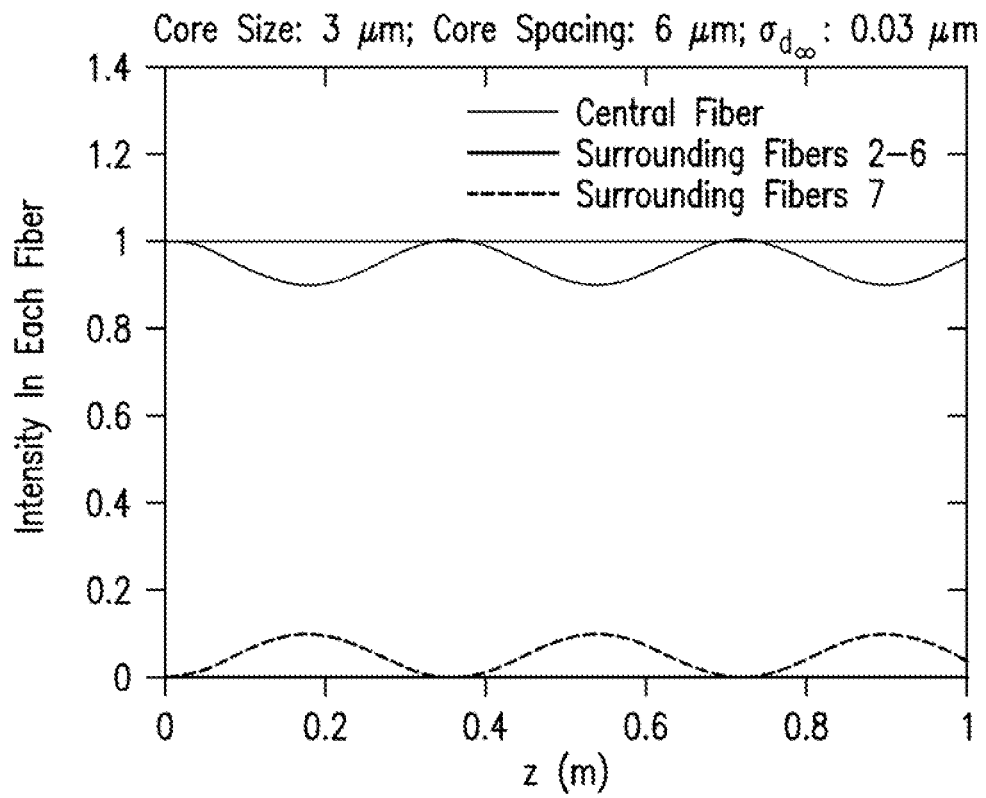
Figure 24C:
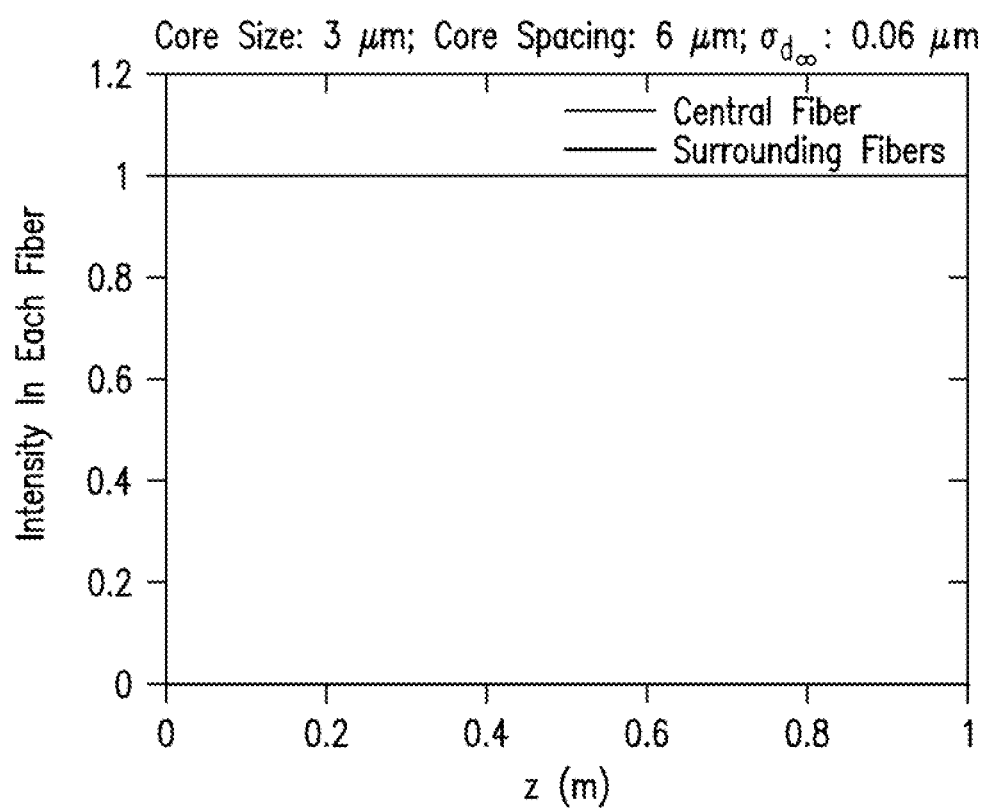

An additional parameter that can influence mode coupling can be the non-uniformity of fibers such as fluctuations of core size and irregular core shape. This non-uniformity can introduce the mismatch in propagation constant R between cores and a small amount of mismatch can extensively reduce mode coupling between fibers. (See e.g., References 115 and 117). This great reduction can be observed in FIGS. 24B and 24C, in which the total intensity transferred from central fiber to surrounding fibers for fiber bundles with same core size and 1% and 2% randomness in core size are shown. However even though the fluctuation of core size can introduce mismatch of propagation constants of same order modes, it can introduce the possibility that different order modes in adjacent fibers have nearly equal and can cause strong coupling between cross order modes of neighboring cores. FIG. 24B shows one example that 5th mode of central fiber and 6th mode of one neighboring fiber is almost the same, such that there can be strong coupling between these two modes. Thus it can be important to utilize the non-uniformity to reduce the cross talk between fibers since it can introduce the possibility of cross order mode coupling. To reduce this possibility, reducing the guided modes of each fiber supported can be performed.

By combining all above exemplary results, the parameters of fiber bundles can include a core diameter of 3.0 μm±0.3 μm, or 3.0 μm±0.2 μm, or 3.0 μm±0.1 μm, or a core diameter of 3.0 μm within measurable error.

The exemplary diameter of the core can have a fluctuation of ±0.02 μm to ±0.4 μm; ±0.02 μm to ±0.3 μm, ±0.03 μm to ±0.3 μm; 0.05 μm to ±0.2 μm, or approximately ±0.1 μm. In some embodiments, the core fluctuation can be approximately 0.06 tm (e.g., 2.0%). An even larger mismatch (e.g., larger than ±0.4 μm) could also be used to introduce an even larger mismatch between modes of the cores. However, such a large mismatch in core fluctuation can preferably be used with smaller core diameters (e.g., a core diameter of 2.7 μm, 2.8 μm, 2.9 μm or 3.0 μm) instead of larger core diameters. The exemplary bundle specifications can be used at, and can be based on, a wavelength of between about 630-720 nm. The bundle specifications can also be dependent on the illumination wavelength, and can be selected to reduce crosstalk between optical fibers in the exemplary fiber bundle. In some embodiments, the manufacture of the core can provide for such a fluctuation in the core diameter as inherent in the formation process. Thus, it can be an aspect of the present disclosure that the fluctuation in the core diameter can be defined by the formation of the fiber bundle. In other embodiments, an increased fluctuation as compared to the minimal fluctuation that can be formed can be preferred.

The fiber bundle can also include a core spacing of 8.0 μm±0.7 μm, 8.0 μm±0.5 μm, 8.0 μm±0.4 μm, 8.0 μm±0.3 μm, 8.0 μm±0.2 μm, or 8.0 μm±0.1 μm, or 8.0 μm within measurable error. The fiber bundle can also include a numerical aperture of at least 0.35, at least 0.36, at least 0.37, at least 0.38, at least 0.39, or at least 0.40. In one embodiment, the numerical aperture can be between 0.37 and 0.41 or between 0.38 and 0.41. While the highest NA for current commercially available fiber optic bundles can be approximately 0.40, higher NA can be preferred for reducing crosstalk, and the higher NA can be used should they become available, such as a NA of about 0.42, 0.43, 0.44, or 0.45. In one embodiment, the fiber bundle has a core diameter of 3.0 μm±0.1 μm with fluctuations in the core size of ±0.1 μm to ±0.2 μm, a core spacing of 8.0 μm±0.5 μm, and a numerical aperture of between 0.38 and 0.41.

While there can be variability in each of the parameters as described herein, it can be understood that each of the parameters can be interrelated, and if it is desirable to change one parameter in the formation of the optical fiber, it can also be advisable to change one or more other parameter to compensate for the initial change.

The fiber bundle as described herein can reliably transmit speckle patterns at wavelength 690 nm.

The fiber optic bundles of the present disclosure can have reduced inter-fiber crosstalk. In some embodiments, the reduction in inter-fiber crosstalk at a propagation distance of 0.5 m using 690 nm radiation can be at least 10%, 20%, 30%, 40%, 50%, 60%, 70%, 80%, 90%, or more compared to an available fiber optic bundle, such either of the SCHOTT Type 1 or SCHOTT Type 2 leached image bundles described in Table 2 above. In some embodiments, the inter-fiber crosstalk of the fiber optic bundle can be at a negligible level. While the variance in the fiber size can facilitate that, two adjacent fibers have identical core diameters and thus a relative increase in inter-fiber crosstalk, in some embodiments, the average inter-fiber crosstalk for the fiber optic bundle can be insignificant and provides a near-zero negative contribution to the image quality.

Figure 25A:
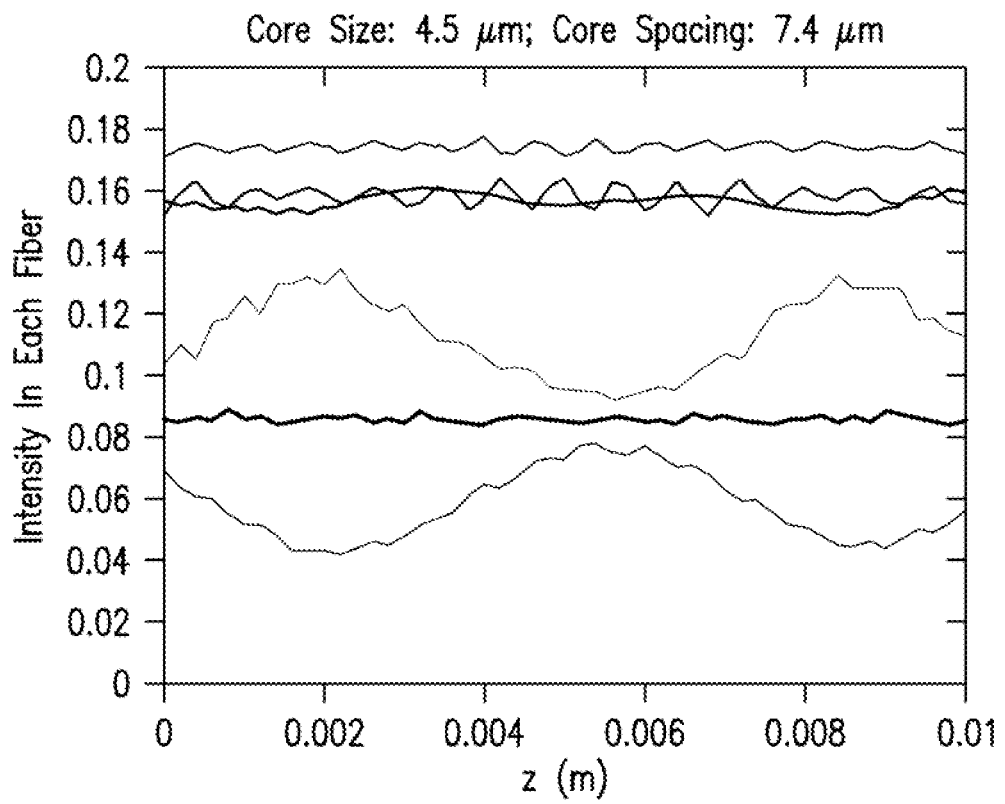
FIGS. 25A-25C are exemplary graphs illustrating that the intensity in each core of 7 core structure can with propagation according to an exemplary embodiment of the present disclosure.
Figure 25B:
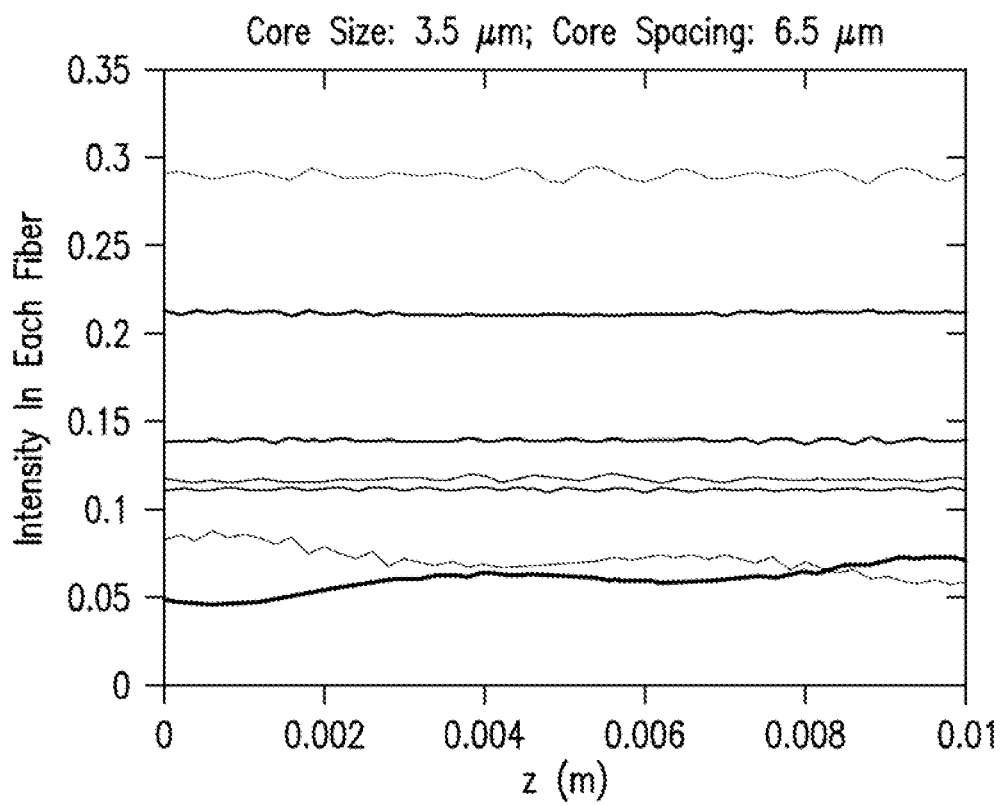
Figure 25C:
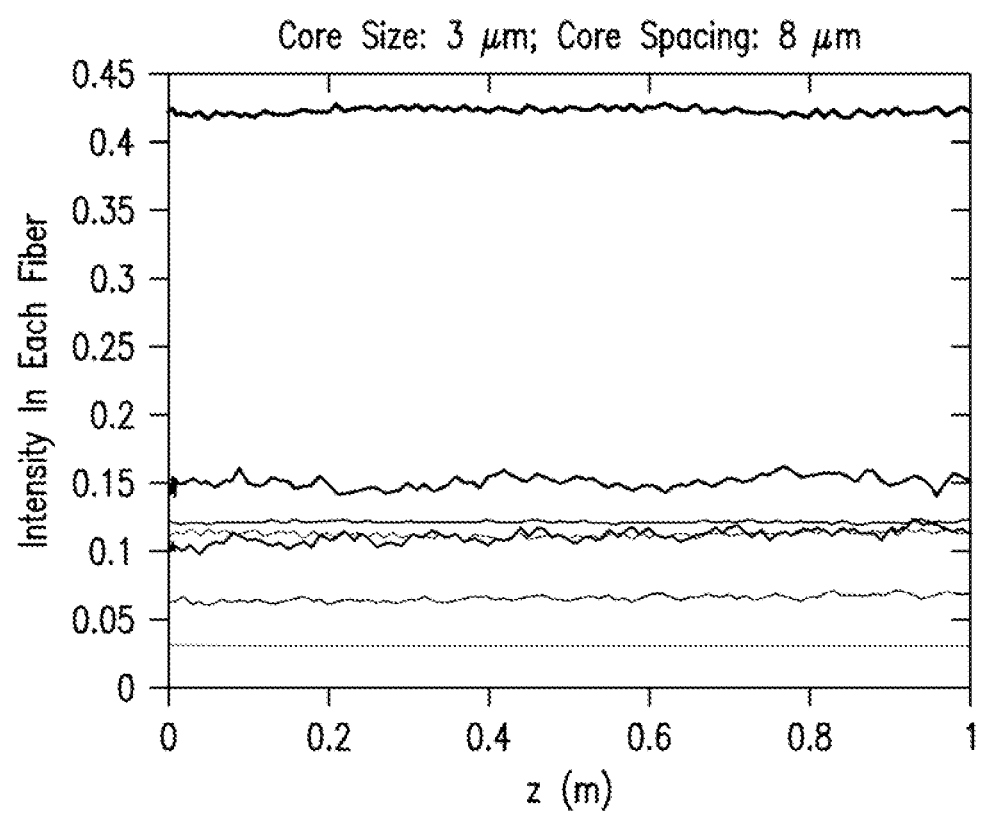

The exemplary coupled intensity in cores of one configuration of type I and type II fiber bundles with ±0.1 μm randomness in core size and exemplary fiber bundles according to the present disclosure are shown in FIGS. 25A-25C, respectively. The strong coupling can be seen in both type I and type II fiber bundles while the coupling in fiber bundles of the present disclosure may not be obvious. When fiber bundles are moving, the coupling between cores could change with time because the motion can change the mode overlapping and introduce modulation to the extra phase difference between cores due to bending and twisting of fiber bundles. (See, e.g., References 124 and 125). However for totally decoupled cores, the effect of fiber bundles motion can be weak, and can be neglected. So, to conduct in vivo LSI, a fiber bundle with fully decoupled cores can be preferred to eliminate the influence of bundle motion. The fiber bundle, as described herein, has shown the small coupling between cores so that it should not be sensitive to the bundle motion.

Optical fiber bundles have been demonstrated to be a key component to conduct endoscopic LSI. The transmitted laser speckles can be modulated by inter-fiber coupling reducing the accuracy of speckle temporal statistics. As described herein, coupled mode theory can be applied, and the influence of fiber core size, core spacing, numerical aperture and variations in core size on mode coupling and speckle modulation has been analyzed. The analysis of the speckle intensity autocorrelation of time-resolved speckle frames illustrated that a fiber bundle with about 3±0.1 μm core size, about 81 im core spacing and about 0.40 NA, can facilitate reliable speckle transmission to conduct endoscopic LSI at about 690 nm. The exemplary results can provide solutions and recommendations for the design, selection and optimization of fiber bundles to conduct endoscopic LSI.

Figure 40:
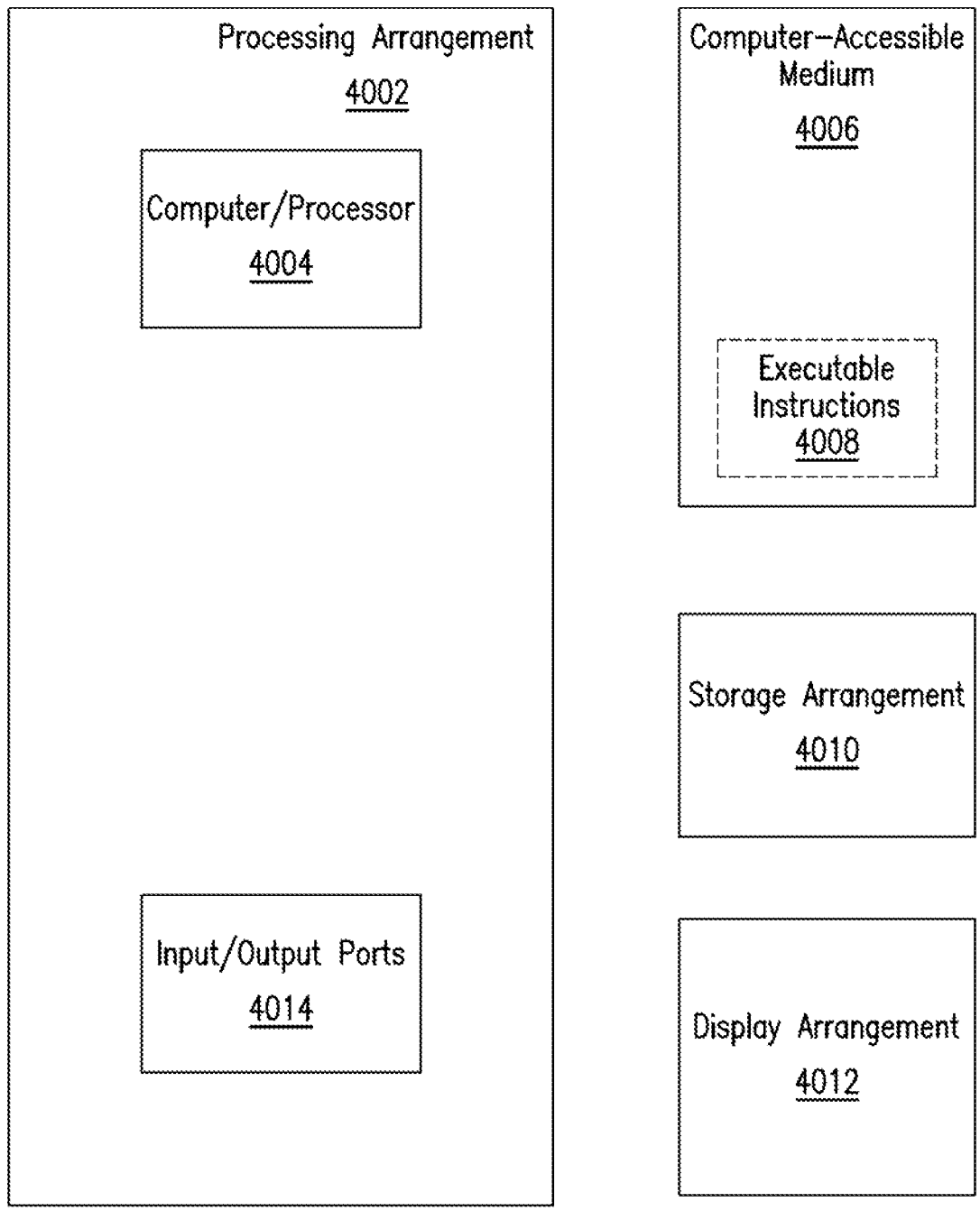
FIG. 40 is an illustration of an exemplary block diagram of an exemplary system in accordance with certain exemplary embodiments of the present disclosure.

FIG. 40 shows a block diagram of an exemplary embodiment of a system according to the present disclosure. For example, exemplary procedures in accordance with the present disclosure described herein can be performed by a processing arrangement and/or a computing arrangement 4002. Such processing/computing arrangement 4002 can be, for example entirely or a part of, or include, but not limited to, a computer/processor 4004 that can include, for example one or more microprocessors, and use instructions stored on a computer-accessible medium (e.g., RAM, ROM, hard drive, or other storage device).

As shown in FIG. 40, for example a computer-accessible medium 4006 (e.g., as described herein above, a storage device such as a hard disk, floppy disk, memory stick, CD-ROM, RAM, ROM, etc., or a collection thereof) can be provided (e.g., in communication with the processing arrangement 4002). The computer-accessible medium 4006 can contain executable instructions 4008 thereon. In addition or alternatively, a storage arrangement 4010 can be provided separately from the computer-accessible medium 4006, which can provide the instructions to the processing arrangement 4002 so as to configure the processing arrangement to execute certain exemplary procedures, processes and methods, as described herein above, for example.

Further, the exemplary processing arrangement 4002 can be provided with or include an input/output arrangement 4014, which can include, for example a wired network, a wireless network, the interne, an intranet, a data collection probe, a sensor, etc. As shown in FIG. 40, the exemplary processing arrangement 4002 can be in communication with an exemplary display arrangement 4012, which, according to certain exemplary embodiments of the present disclosure, can be a touch-screen configured for inputting information to the processing arrangement in addition to outputting information from the processing arrangement, for example. Further, the exemplary display 4012 and/or a storage arrangement 4010 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.
1. Virmani R, Kolodgie F D, Burke A P, Farb A, Schwartz S M. Lessons from sudden coronary death: A comprehensive morphological classification scheme for atherosclerotic lesions. *Arterioscler Thromb Vasc Biol.* 2000; 20:1262-1275
2. Finn A V, Nakano M, Narula J, Kolodgie F D, Virmani R. Concept of vulnerable/unstable plaque. *Atheroscler Throm Vasc Biol.* 2010; 30:1282-1292
3. Schroeder A P, Falk E. Vulnerable and dangerous coronary plaques. *Atherosclerosis.* 1995; 118 Suppl:5141-149
4. Kolodgie F D, Burke A P, Farb A, Gold H K, Yuan J. The thin-cap fibroatheroma: A type of vulnerable plaque: The major precursor to acute coronary syndromes. *Curr Opin Cardiol.* 2001; 16:285-292
5. Virmani R, Burke A P, Kolodgie F D, Farb A. Vulnerable plaque: The pathology of unstable coronary lesions. *J Interv Cardiol.* 2002; 15:439-446
6. Garcia-Garcia H, Mintz G S, Lerman A, Vince D, Margolis M, van ED G, Morel M, Nair A, Virmani R, Burke A, Stone G, Serruys P W. Tissue characterization using intravascular radiofrequency data analysis: Recommendations for acquisition, analysis, interpretation and reporting. *Eurointervention.* 2009; 5:177-189
7. Murray S, Stables R, Palmer N. Virtual histology imaging in acute coronary syndromes: Useful or just a research tool. *J Invasive Cardiol.* 2009; 22:84-91
8. Sangiori G, Clementi F, Cola C, Biondi-Zoccai G. Plaque vulnerability and related coronary event prediction by intravascular ultrasound with virtual histology: Its a long way to tipperary. *Catheter Cardiovasc Interv.* 2007; 70:203-210
9. Jang I K, Tearney G, Bouma B. Visualization of tissue prolapse between coronary stent struts by optical coherence tomography: Comparison with intravascular ultrasound. *Circulation.* 2001; 104:2754
10. Grube E, Gerckens U, Buellesfeld L, Fitzgerald P J. Images in cardiovascular medicine. Intracoronary imaging with optical coherence tomography: A new high-resolution technology providing striking visualization in the coronary artery. *Circulation.* 2002; 106:2409-2410
11. Jang I K, Bouma B E, Kang D H, Park S J, Park S W, Seung K B, Choi K B, Shishkov M, Schlendorf K, Pomerantsev E, Houser S L, Aretz H T, Tearney G J. Visualization of coronary atherosclerotic plaques in patients using optical coherence tomography: Comparison with intravascular ultrasound. *J Am Coll Cardiol.* 2002; 39:604-609
12. Yabushita H, Bouma B E, Houser S L, Aretz H T, Jang I K, Schlendorf K H, Kauffman C R, Shishkov M, Kang D H, Halpern E F, Tearney GJ. Characterization of human atherosclerosis by optical coherence tomography. *Circulation.* 2002; 106:1640-1645
13. Liebson P R, Klein LW. Intravascular ultrasound in coronary atherosclerosis: A new approach to clinical assessment. *Am Heart J.* 1992; 123:1643-1660
14. Rogers W J, Prichard J W, Hu Y L, Olson P R, Benckart D H, Kramer C M, Vido D A, Reichek N. Characterization of signal properties in atherosclerotic plaque components by intravascular mri. *Arterioscler Thromb Vasc Biol.* 2000; 20:1824-1830

15. Brezinski M E, Tearney G J, Bouma B E, Izatt J A, Hee M R, Swanson E A, Southern J F, Fujimoto J G. Optical coherence tomography for optical biopsy. Properties and demonstration of vascular pathology. *Circulation.* 1996; 93:1206-1213

16. Tearney G, J., Bouma B E. Atherosclerotic plaque characterization by spatial and temporal speckle pattern analysis. *Optics Letters.* 2002; 27:533-535

17. Schmermund A, Rodermann J, Erbel R. Intracoronary thermography. *Herz.* 2003; 28:505-512

18. Stefanadis C, Toutouzas K, Tsiamis E, Pitsavos C, Papadimitriou L, Toutouzas P. Identification and stabilization of vulnerable atherosclerotic plaques: The role of coronary thermography and external heat delivery. *Indian Heart J.* 2001; 53:104-109

19. Uchida Y, Fujimori Y, Hirose J, Oshima T. Percutaneous coronary angioscopy. *Jpn Heart J.* 1992; 33:271-294

20. Casscells W, Hathorn B, David M, Krabach T, Vaughn W K, McAllister H A, Bearman G, Willerson J T. Thermal detection of cellular infiltrates in living atherosclerotic plaques: Possible implications for plaque rupture and thrombosis. *Lancet.* 1996; 347:1447-1451

21. Moreno P R, Lodder R A, Purushothaman K R, Charash W E, O'Connor W N, Muller J E. Detection of lipid pool, thin fibrous cap, and inflammatory cells in human aortic atherosclerotic plaques by near-infrared spectroscopy. *Circulation.* 2002; 105:923-927

22. Waxman S, Dixon S, P LA, JW M, JL P, D C, J T, RW N, al e. In vivo validation of a catheter-based near-infrared spectroscopy system for detection of lipid core coronary plaques: Initial results and exploratory analysis of the spectroscopic assessment of coronary lipid (spectacl) multicenter study. *J Am Coll Cardiol Img.* 2009; 2:858-868.

23. Ishibashi F, Yokoyama S, Miyahara K, Dabreo A, Weiss E R, Iafrati M, Takano M, Okamatsu K, Mizuno K, Waxman S. Quantitative colorimetry of atherosclerotic plaque using the l*a*b* color space during angioscopy for the detection of lipid cores underneath thin fibrous caps. *Int J Cardiovasc Imaging.* 2007; 23:679-691

24. Madjid M, Willerson J T, Casscells S W. Intracoronary thermography for detection of high-risk vulnerable plaques. *J Am Coll Cardiol.* 2006; 47:C80-85

25. Arbab-Zadeh A, Hoe J. Quantification of coronary arterial stenoses by multidetector ct angiography in comparison with conventional angiography methods, caveats, and implications. *JACC Cardiovasc Imaging.* 2011; 4:191-202

26. Chang H, Chung N. Clinical perspective of coronary computed tomographic angiography in diagnosis of coronary artery disease. Circ J. 2011; 75:246-252

27. Arbustini E, Grasso M, Diegoli M, Pucci A, Bramerio M. Coronary atherosclerotic plaques with and without thrombus in ischemic heart syndromes: A morphologic, immunohistochemical and biochemical study. *Am J Cardiol.* 1991; 68:36B-50B 28. Cheruvu P K, Finn A V, Gardner C, Caplan J, Goldstein J. Frequency and distribution of thin-cap fibroatheroma and ruptured plaques in human coronary arteries. *J Am Coll Cardiol.* 2007; 50:940-949

29. Serruys P W, Garcia-Garcia H M, Regar E. From postmortem characterization to the in vivo detection of thin capped fibroatheromas: The missing link towards percutaneous treatment. *J Am Coll Cardiol.* 2007; 50:950-952

30. Mizukoshi M, Imanishi T, Tanaka A, Kubo T, Liu Y, Takarada S, Kitabata H, Tanimoto T, Komukai K, Ishibashi K, Akasaka t. Clinical classification and plaque morphology determined by optical coherence tomography in unstable angina pectoris. *Am J Cardiol.* 2010; 106:323-328

31. Tanaka A, Imanishi T, Kitabata H, kubo T, Takarada S, Tanimoto T, Kuroi A, Tsujioka H, al e. Lipid rich plaque and myocardial perfusion after successful stenting in patients with non-st segment elevation acure coronary syndrome: An optical coherence tomography study. *Eur Heart J.* 2009; 30

32. Lee R. Atherosclerotic lesion mechanics versus biology. *Z Kardiol.* 2000; 89:80-84

33. Richardson P D, Davies M J, Born G V. Influence of plaque configuration and stress distribution on fissuring of coronary atherosclerotic plaques. *Lancet.* 1989; 2:941-944

34. Williamson S D, Lam Y, Younis H F, Huang H. On the sensitivity of wall stresses in diseased arteries to variable material properties. *J Biomech Eng.* 2003; 125:147-155

35. Shah P K. Mechanisms of plaque vulnerability and rupture. J Am Coll Cardiol. 2003; 41:15S-22S 36. Arroyo L, Lee R. Mechanisms of plaque rupture: Mechanical and biologic interactions. *Cardiovasc Res.* 1999; 41:369-375

37. Richardson P D. Biomechanics of plaque rupture: Progress, problems, and new frontiers. *Ann Biomed Eng.* 2002; 30:524-536

38. Finet G, Ohayon J, Rioufol G, Lefloch S, Tracqui P, Dubreuil O, Tabib A. Morphological and biomechanical aspects of vulnerable coronary plaque. *Arch Mal Coeur Vaiss.* 2007; 100:547-553

39. Ohayon J, Dubreuil O, Tracqui P, Le Floc'h S, Rioufol G, Chalabreysse L, Thivolet F, Pettigrew R I, Finet G. Influence of residual stress/strain on the biomechanical stability of vulnerable coronary plaques: Potential impact for evaluating the risk of plaque rupture. *Am J Physiol Heart Circ Physiol.* 2007; 293:H1987-1996

40. Sadat U, Teng Z, Gillard J H. Biomechanical structural stresses of the atherosclerotic plaque. *Expert Rev Cardiovasc Ther.* 2010; 8:1469-1481

41. Finet G, Ohayon J, Rioufol G. Biomechanical interaction between cap thickness, lipid core composition and blood pressure in vulnerable coronary plaque: Impact on stability or instability. *Coron Artery Dis.* 2004; 15:13-20

42. Nadkarni S K, Bouma B E, Helg T, Chan R, Halpern E, Chau A, Minsky M S, Motz J T, Houser S L, Tearney G J. Characterization of atherosclerotic plaques by laser speckle imaging. *Circulation.* 2005; 112:885-892

43. Nadkarni S K, Bilenca A, Bouma B E, Tearney G J. Measurement of fibrous cap thickness in atherosclerotic plaques by spatiotemporal analysis of laser speckle images. *J Biomed Opt.* 2006; 11:21006

44. Nadkarni S K, Bouma B E, D Y, Tearney G, J. Laser speckle imaging of atherosclerotic plaques through optical fiber bundles. *J Biomed Opt.* 2008; 13:054016

45. Nadkarni S K, Bouma B E, de Boer J, Tearney G J. Evaluation of collagen in atherosclerotic plaques: The use of two coherent laser-based imaging methods. *Lasers Med Sci.* 2009; 24:439-445

46. Hajjarian Z, Xi J Q, Jaffer F A, Tearney G J, Nadkarni S K. Intravascular laser speckle imaging for the mechanical evaluation of the arterial wall. *J Biomed Opt.* 2011; [epub ahead of print]
47. Koskinas K, Feldman C, Chatzizisis Y, Coskun A, Jonas M, Maynard C, Baker A, Papafaklis M, Edelman E, Stone P. Natural history of experimental coronary atherosclerosis and vascular remodeling in relation to endothelial shear stress: A serial, in vivo intravascular ultrasound study. *Circulation.* 2010; 121:2092-2101
48. Papafaklis M, Koskinas K, Chatzizisis Y, Stone P, Feldman C. In-vivo assessment of the natural history of coronary atherosclerosis: Vascular remodeling and endothelial shear stress determine the complexity of atherosclerotic disease progression. *Curr Opin Cardiol.* 2010; 25:627-638
49. Kolodgie F, Burke A N, G, Cheng Q, Xu X, Virmani R. Free cholesterol in atherosclerotic plaques: Where does it come from? *Curr Opin Lipidol.* 2007; 18:500-507
50. Loree H M, Tobias B J, Gibson L J, Kamm R D, Small D M, Lee R T. Mechanical properties of model atherosclerotic lesion lipid pools. *Arterioscler Thromb.* 1994; 14:230-234
51. Bauriedel G, Hutter R, Welsch U, Bach R, Sievert H, Luderitz B. Role of smooth muscle cell death in advanced coronary primary lesions: Implications for plaque instability. *Cardiovasc Res.* 1999; 41:480-488
52. Newby A C, Zaltsman A B. Fibrous cap formation or destruction—the important importance of vascular smooth muscle cell proliferation, migration and matrix formation. *Cardiovasc Res.* 1999; 41:345-360
53. Rekhter M D, Hicks G W, Brammer D W, Hallak H, Kindt E, Chen J, Rosebury W S, Anderson M K, Kuipers P J, Ryan M J. Hypercholesterolemia causes mechanical weakening of rabbit atheroma: Local collagen loss as a prerequisite of plaque rupture. *Circ Res.* 2000; 86:101-108
54. Chau A H, Chan R C, Shishkov M, MacNeill B. Mechanical analysis of atherosclerotic plaques based on optical coherence tomography. *Annals of Biomedical Engineering.* 2004; 32:1494-1503
55. Tang D, Yang C, Kobayashi S, Ku D N. Effect of a lipid pool on stress/strain distributions in stenotic arteries: 3-d fluid-structure interactions (fsi) models. *J Biomech Eng.* 2004; 126:363-370
56. Stone G, Lansky A, Carlier S, al e. A prospective, natural history study of multimodality invasive imaging to characterize vulnerable plaque: First report of the baseline findings from the prospect trial. *Journal of the American College of Cardiology* 2007; 49:19B
57. Stone G W, Serryus P W, de Bruyne B. The prospect trial: An imaging study in patients with unstable atherosclerotic lesions. www.clinicaltrials.gov. 2009
58. Motoyama S S M, Harigaya H, Anno H, Inoue K, Hara T, Naruse H, Ishii J, Hishida H, Wong N D, Virmani R, Kondo T, Ozaki Y, Narula J. Computed tomographic angiography characteristics of atherosclerotic plaques subsequently resulting in acute coronary syndrome. *J Am Coll Cardiol.* 2009; 54:49-57
59. Manka R J C, Kozerke S, Vitanis V, Crelier G, Gebker R, Schnackenburg B, Boesiger P, Fleck E, Paetsch I. Dynamic 3-dimensional stress cardiac magnetic resonance perfusion imaging: Detection of coronary artery disease and volumetry of myocardial hypoenhancement before and after coronary stenting. *J Am Coll Cardiol.* 2011; 57:437-444
60. Tearney G J, Waxman S, Shishkov M, Vakoc B J, Suter M J. Three-dimensional coronary artery microscopy by intracoronary optical frequency domain imaging. *JACC Cardiovac Imaging.* 2008; 1:752-761
61. Jang I K, Tearney G J, MacNeill B, Takano M, Moselewski F. In vivo characterization of coronary atherosclerotic plaque by use of optical coherence tomography. *Circulation.* 2005; 111:1551-1556
62. MacNeill B D, Jang I K, Bouma B E, Iftimia N, Takano M, Yabushita H, Shishkov M, Kauffman C R, Houser S L, Aretz H T, DeJoseph D, Halpern E F, Tearney G J. Focal and multi-focal plaque macrophage distributions in patients with acute and stable presentations of coronary artery disease. *J Am Coll Cardiol.* 2004; 44:972-979
63. Baldewsing R A, Schaar J A, de Korte C L, Mastik F, Serruys P W, van der Steen A F. Intravascular ultrasound elastography: A clinician's tool for assessing vulnerability and material composition of plaques. *Stud Health Technol Inform.* 2005; 113:75-96
64. Schaar J A, De Korte C L, Mastik F, Strijder C, Pasterkamp G, Boersma E, Serruys P W, Van Der Steen A F. Characterizing vulnerable plaque features with intravascular elastography. *Circulation.* 2003; 108:2636-2641
65. Chan R C, Chau A H, Karl W C, Nadkarni S K, Khalil A S. Oct-based arterial elastography: Rocust estimation exploiting tissue biomechanics. *Optics Express.* 2004; 12:4558-4572
66. Baldewsing R, Danilouchkine M, Mastik F, Schaar J, Serruys P, van der Steen A. An inverse method for imaging the local elasticity of atherosclerotic coronary plaques. *IEEE Trans Inf Technol Biomed.* 2008; 12:277-289
67. Baldewsing R, Schaar J A, Mastik F, Van der Steen A F. Local elasticity imaging of vulnerable atherosclerotic coronary plaques. *Adv Cardiol.* 2007; 44:35-61
68. Ong W. Laser speckle imaging for the mechanical evaluation of cartilage. *Biomedical Science.* 2010; MSc
69. Hajjarian Z, and Nadkarni S K. Are preparing a manuscript titled 'measurement of substrate viscoelastic properties from laser speckle fluctuations.' 2010
70. Hajjarian Z, Jaffer F A, Tearney G J, Nadkarni S K. Intracoronary laser speckle imaging for the mechanical evaluation of the arterial wall. submitted to *J Biomed Opt.* 2010
71. Goodman J W. Statistical optics. Wiley Interscience; 2000:347-356.
72. Lewis J C. On the einstein-stoke diffusion coefficient for brownian motion in two dimensions. *Phys Letts.* 1973; 44:245-247
73. Mason T G, Weitz D A. Optical measurements of frequency-dependent linear viscoelasticity moduli of complex fluids. *Physical Review Letters.* 1995; 74:1250-1253
74. Dasgupta B R, Weitz D A. Microrheology of cross-linked polyacrylamide networks. *Phys Rev E Stat Nonlin Soft Matter Phys.* 2005; 71:021504
75. Hajjarian Z, Nadkarni S K. Are preparing a manuscript titled 'measurement of substrate mechanical properties from laser speckle fluctuations.' 2011
76. de Korte C L, Schaar J A, Mastik F, Serruys P W, van der Steen A F. Intravascular elastography: From bench to bedside. *J Intery Cardiol.* 2003; 16:253-259
77. Lee R T, Richardson S G, Loree H M, Grodzinsky A J, Gharib S A, Schoen F J, Pandian N. Prediction of mechanical properties of human atherosclerotic tissue by high-frequency intravascular ultrasound imaging. An in vitro study. *Arterioscler Thromb.* 1992; 12:1-5

78. Gonik M M, Mishin A B, Zimnyakov D A. Visualization of blood microcirculation parameters in human tissues by time-integrated dynamic speckles analysis. *Ann N Y Acad Sci.* 2002; 972:325-330
79. Wang L, Jacques S L, Zheng L. Mcml—monte carlo modeling of light transport in multi-layered tissues. *Comput Methods Programs Biomed.* 1995; 47:131-146
80. Sadhwani A, Schomacker K, T., Tearney G, J., Nishioka N S. Determination of teflon thickness with laser speckle. 1. Potential for burn depth diagnosis. *Applied Optics.* 1996; 35:5727-5735
81. Boas D A, Nishimura G, Yodh A G. Diffusing temporal light correlation for burn diagnosis. *SPIE.* 1999; 2979: 468-474
82. Waxman S, Khabbaz K, Connolly R, Tang J, Dabreo A, Egerhei L, Ishibashi F, Muller J E, Tearney G M. Intravascular imaging of atherosclerotic human coronaries in a porcine model: A feasibility study. *The International Journal of Cardiovascular Imaging.* 2008; 24:37-44
83. Chau A H, Motz J T, Gardecki J A, Waxman S, Bouma B E, Tearney G J. Fingerprint and high-wavenumber raman spectroscopy in a human-swine coronary xenograft in vivo. *Journal of Biomedical Optics.* 2008; 13:040501
84. Tearney G J, Waxman S, Shishkov M, Vakoc B J, Suter M J, Freilich M I, Desjardins A E, Oh W Y, Bartlett L A, Rosenberg M, Bouma B E. Three-dimensional coronary artery microscopy by intracoronary optical frequency domain imaging. *JACC Cardiovasc Imaging.* 2008; 1:752-761
85. Tearney G, J., Boppart S A, Bouma B E, Brezinski M, Weissman N J. Scanning single mode fiber optic catheter-endoscope for optical coherence tomograpphy. *Optics Letters.* 1996; 21:543-545
86. Pratt W. *Digital image processing.* John Wiley and Sons, Inc.
87. Desai R A, Yang M T, Sniadecki N J, Legant W R, Chen C S. Microfabricated post array detectors (mpads): An approach to isolate mechanical forces. *Journal of Visualized Experiments.* 2007
88. Tan J L, Tien J, Pirone D M, Gray D S, Bhadrirahu K, Chen C S. Cells lying on a bed of microneedles: An approach to isolate mechanical force. *Proc Natl Acad Sci USA.* 2003; 100:1484-1489
89. Irimia D. Microfluidic technologies for temporal perturbations of chemotaxis. *Annu Rev Biomed Eng.* 2010; 12:259-284
90. Bonnema GT, O. Cardinal K, Williams S K, Barton J K. A concentric three element radial scanning optical coherence tomography endoscope. *J of Biophotonics.* 2009; 2:353-356
91. Smith-Vaughan H, Byun R, Halpin S, Nadkarni M A, Jacques N A, Hunter N, Morris P S, Leach A J. Interventions for prevention of otitis media may be most effective if implemented in the first weeks of life. *Int J Pediatr Otorhinolaryngol.* 2008; 72:57-61
92. Marenzi G, Assanelli E, Campodonico J, Lauri G, Marana I, De Metrio M, Moltrasio M, Grazi M, Rubino M, Veglia F, Fabbiocchi F, Bartorelli A L. Contrast volume during primary percutaneous coronary intervention and subsequent contrast-induced nephropathy and mortality. *Ann Intern Med.* 2009; 150:170-177
93. Barlis P, Gonzalo N, Di Mario C, Prati F, Buellesfeld L, Rieber J, Dalby M C, Ferrante G, Cera M, Grube E, Serruys P W, Regar E. A multicentre evaluation of the safety of intracoronary optical coherence tomography. *EuroIntervention.* 2009; 5:90-95
94. Tearney G J, Yabushita H, Houser S L, Aretz H T, Jang I K, Schlendorf K H, Kauffman C R, Shishkov M, Halpern E F, Bouma B E. Quantification of macrophage content in atherosclerotic plaques by optical coherence tomography. *Circulation.* 2003; 107:113-119
95. Nadkarni S K, Pierce M C, Park B H, de Boer J F, Whittaker P, Bouma B E, Bressner J E, Halpern E, Houser S L, Tearney G J. Measurement of collagen and smooth muscle cell content in atherosclerotic plaques using polarization-sensitive optical coherence tomography. *Journal of the American College of Cardiology.* 2007; 49:1474-1481
96. J. C. Dainty, Laser Speckle and Related Phenomena, 2nd enl. (Springer-Verlag, 1984), Vol. v. 9, p. xv, 342 p.
97. J. W. Goodman, Speckle Phenomena in Optics: Theory and Applications (Roberts & Company Publishers, 2007), p. xvi, 387 p.
98. D. a Boas and A. K. Dunn, "Laser speckle contrast imaging in biomedical optics," J. Biomed. Opt. 15, 011109 (2010).
99. S. K. Nadkarni, B. E. Bouma, T. Helg, R. Chan, E. Halpern, A. Chau, M. S. Minsky, J. T. Motz, S. L. Houser, and G. J. Tearney, "Characterization of atherosclerotic plaques by laser speckle imaging," Circulation 112, 885-92 (2005).
100. S. Nadkarni, "Laser speckle imaging of atherosclerotic plaques through optical fiber bundles," J. Biomed. Opt. 13, 1-14 (2008).
102. Z. Hajjarian, J. Xi, F. a Jaffer, G. J. Tearney, and S. K. Nadkarni, "Intravascular laser speckle imaging catheter for the mechanical evaluation of the arterial wall," J. Biomed. Opt. 16, 026005 (2011).
103. Z. Hajjarian and S. K. Nadkarni, "Evaluating the viscoelastic properties of tissue from laser speckle fluctuations," Sci. Rep. 2, 316 (2012).
104. K. Dunn, H. Bolay, M. a Moskowitz, and D. a Boas, "Dynamic imaging of cerebral blood flow using laser speckle," J. Cereb. Blood Flow Metab. 21, 195-201 (2001).
105. L. Song and D. Elson, "Endoscopic laser speckle contrast imaging system using a fibre image guide," Proc. SPIE 7907, 79070E-79070E-9 (2011).
106. D. A. Zimnyakov, A. P. Sviridov, L. V. Kuznetsova, S. A. Baranov, and N. Y. Ignatieva, "Monitoring of tissue thermal modification with a bundle-based full-field speckle analyzer," Appl. Opt. 45, 4480 (2006).
107. H. Zhang, P. Li, N. Feng, J. Qiu, B. Li, W. Luo, and Q. Luo, "Correcting the detrimental effects of nonuniform intensity distribution on fiber-transmitting laser speckle imaging of blood flow," Opt. Express 20, 508-17 (2012).
108. A. F. Gmitro and D. Aziz, "Confocal microscopy through a fiber-optic imaging bundle," Opt. Lett. 18, 565-567 (1993).
109. T. Xie, D. Mukai, S. Guo, M. Brenner, and Z. Chen, "Fiber-optic-bundle-based optical coherence tomography," Opt. Lett. 30, 1803-1805 (2005).
110. V. Dubaj, A. Mazzolini, A. Wood, and M. Harris, "Optic fibre bundle contact imaging probe employing a laser scanning confocal microscope," J. Microsc. 207, 108-117 (2002).
111. W. G. bel, J. N. D. Kerr, A. Nimmerjahn, and F. Helmchen, "Miniaturized two-photon microscope based on a flexible coherent fiberbundle and a gradient-index lens objective," Opt. Lett. 29, 2521-2523 (2004).
112. R. Juskattis, T. Wilson, and T. F. Watson, "Real-time white light reflection confocal microscopy using a fibre-optic bundle," Scanning 19, 15-19 (1997).

113. R. Juskattis, T. Wilson, and T. Watson, "Real-time white light reflection confocal microscopy using a fibre-optic bundle," Scanning 19, 15-19 (1997).
114. Jia-ming Liu, Photonic Devices (Cambridge University Press, 2005).
115. K. L. Reichenbach and C. Xu, "Numerical analysis of light propagation in image fibers or coherent fiber bundles," Opt. Express 15, 2151-65 (2007).
116. X. Chen, K. L. Reichenbach, and C. Xu, "Experimental and theoretical analysis of core-to-core coupling on fiber bundle imaging," Opt. Express 16, 21598-607 (2008).
117. N. Ortega-Quijano, F. Fanjul-Velez, and J. L. Arce-Diego, "Optical crosstalk influence in fiber imaging endoscopes design," Opt. Commun. 283, 633-638 (2010).
118. A. Saglam, H. Ford, and R. Tatam, "Numerical modelling of imaging fibre bundles and their application in Optical Coherence Tomography," Proc. SPIE 7753, 775350 (2011).
119. J.-H. Han and J. U. Kang, "Effect of multimodal coupling in imaging micro-endoscopic fiber bundle on optical coherence tomography," Appl. Phys. B. 106, 635-643 (2012).
120. A. W. SNYDER, "Coupled-Mode Theory for Optical Fibers," J. Opt. Soc. Am. 62, 1267-1277 (1972).
121. A. Snyder and J. Love, Optical Waveguide Theory (1983).
122. A. Hardy and W. Streifer, "Coupled mode theory of parallel waveguides," J. Light. Technol. LT-3, 1135 (1985).
123. J. Goodman, Statistical Optics (New York, Wiley-Interscience, 2000).
124. M. Skorobogatiy, K. Saitoh, and M. Koshiba, "Full-vectorial coupled mode theory for the evaluation of macro-bending loss in multimode fibers. application to the hollow-core photonic bandgap fibers," Opt. Express 16, 14945-53 (2008).
125. M. Koshiba, K. Saitoh, K. Takenaga, and S. Matsuo, "Multi-core fiber design and analysis: coupled-mode theory and coupled-power theory," Opt. Express 19, B102-11 (2011).
126. C.-Y. Lee and J.-H. Han, "Integrated spatio-spectral method for efficiently suppressing honeycomb pattern artifact in imaging fiber bundle microscopy," Opt. Commun. 306, 67-73 (2013).
127. D. a Boas and A. K. Dunn, "Laser speckle contrast imaging in biomedical optics," J. Biomed. Opt. 15, 011109 (2010).
128. S. J. Kirkpatrick, K. Khaksari, D. Thomas, and D. D. Duncan, "Optical vortex behavior in dynamic speckle fields," J. Biomed. Opt. 17, 050504 (2012).

What is claimed is:

1. A catheter system for obtaining information regarding at least one biological structure, comprising:
    at least one fiber through which light is propagated to the biological structure when a portion of the catheter system is arranged within the biological structure;
    a reflector having multiple surfaces and arranged with respect to the at least one fiber to simultaneously receive the light at each of the multiple surfaces and deliver reflected light that induces speckle patterns in the biological structure that are directed back to the reflector;
    a fiber bundle configured to receive, from the reflector, the speckle patterns induced by the reflected light that includes the speckle patterns induced by the reflected light from the multiple surfaces of the reflector, wherein the fiber bundle is further configured to deliver the reflected light obtained, via the multiple surfaces of the reflector, from the biological structure at multiple illumination locations to a detector to image the speckle patterns from the biological structure at the multiple illumination locations based on the reflected light without a rotation of the at least one fiber, the reflector, or the fiber bundle; and
    a pullback arrangement which, during delivery of the reflected light to the multiple illumination locations, is configured to pull back the at least one of the at least one fiber and the fiber bundle to adjust a position of the multiple illumination location across the biological structure.

2. The system of claim 1, wherein the multiple surfaces of the reflector includes more than two surfaces.

3. The system of claim 1, wherein the reflector forms a shape of at least one of a cone, a polygon, or a pyramid.

4. The system of claim 1, wherein the at least one biological structure is an in-vivo vessel and the fiber bundle is configured to deliver the reflected light over a circumference of the in-vivo vessel.

5. The system of claim 4, wherein the pullback arrangement is configured to pull back the at least one of the at least one fiber or the fiber bundle during delivery of the reflected light over the circumference of the in-vivo vessel to obtain information about the circumference and along a length of the in-vivo vessel without rotation of the at least one fiber, the reflector, or the fiber bundle.

6. The system of claim 1, further comprising at least one splitter coupled to the at least one fiber to split the light at different wavelengths before arriving at the reflector, and wherein the fiber bundle is further configured to receive the reflected light at the different wavelengths.

7. The system of claim 1, further comprising at least one of a lens, a GRIN lens, a ball lens, or an imaging lens coupled to the at least one fiber to receive the light before being propagated to or from the biological structure.

8. The system of claim 1, wherein the reflector having multiple surfaces is further configured to deliver reflected light that includes speckle patterns having an intensity that varies in time.

9. The system of claim 8, wherein the reflector having multiple surfaces is further configured to deliver reflected light while maintaining variations of the intensity of the speckle patterns to provide information regarding mechanical properties of the at least one biological structure.

10. A catheter system for obtaining information regarding an in-vivo vessel, comprising:
    at least one fiber through which light is propagated to the in-vivo vessel;
    a reflector having multiple surfaces and arranged with respect to the at least one fiber to simultaneously receive the light at each of the multiple surfaces and simultaneously deliver reflected light that induces speckle patterns in the in-vivo vessel that are directed back to the reflector;
    a fiber bundle configured to receive, from the reflector, the speckle patterns induced by the reflected light that includes the speckle patterns induced by the reflected light from the multiple surfaces of the reflector, wherein the fiber bundle is further configured to deliver the reflected light obtained, via the multiple surfaces of the reflector, from over a circumference of the in-vivo vessel to a detector to image the speckle patterns from the circumference of the in-vivo vessel based on the reflected light without a rotation of the at least one fiber, the reflector, or the fiber bundle; and a pullback arrangement configured to pull back at least one of the at least one fiber or the fiber bundle during delivery of the reflected light over the circumference of the in-vivo vessel to obtain information about the circumference and along a length of the in-vivo vessel.

11. The system of claim 10, wherein the fiber bundle is further configured to deliver light reflected by the in-vivo vessel to the detector to image both the circumference and the length of the in-vivo vessel.

12. The system of claim 11, wherein the image forms a cylindrical map of the in-vivo vessel.

13. The system of claim 12, wherein the cylindrical map of the in-vivo vessel indicates a viscoelasticity distribution over the circumference and the length of the in-vivo vessel.

14. The system of claim 10, wherein the reflector has a shape of a cone, a polygon, or a pyramid.

15. The system of claim 10, wherein the multiple surfaces of the reflector includes more than two surfaces.

16. The system of claim 10, further comprising at least one splitter coupled to the at least one fiber to split the light at different wavelengths before arriving at the reflector, and wherein the fiber bundle is further configured to receive the reflected light at the different wavelengths.

17. The system of claim 10, further comprising at least one of a lens, a GRIN lens, a ball lens, or an imaging lens coupled to the at least one fiber to receive the light before being propagated to or from the in-vivo vessel.

18. The system of claim 10, wherein the reflector having multiple surfaces is further configured to deliver reflected light that includes speckle patterns having an intensity that varies in time.

19. The system of claim 18, wherein the reflector having multiple surfaces is further configured to deliver reflected light while maintaining variations of the intensity of the speckle patterns to provide information regarding mechanical properties of the in-vivo vessel.

* * * * *

UNITED STATES PATENT AND TRADEMARK OFFICE
CERTIFICATE OF CORRECTION

PATENT NO. : 11,129,535 B2
APPLICATION NO. : 15/428012
DATED : September 28, 2021
INVENTOR(S) : Seemantini K. Nadkarni Page 1 of 1

It is certified that error appears in the above-identified patent and that said Letters Patent is hereby corrected as shown below:

In the Specification

Column 11, Line 16, "References 2, 28, 31" should be --References 2, 28, 30-31--.

Column 13, Line 14, "("MM")" should be --("MRI")--.

Column 17, Line 45, "plaque ti" should be --plaque τ--.

Column 20, Line 5, "inti" should be --in τ--.

Column 31, Line 15, "the strength" should be --the coupling strength--.

Column 38, Line 30, "$H_{NF}(u,v) = \prod_{k=1}^{N} H_k(u,v)$" should be --  --.

Column 41, Line 38, "the interne," should be --the internet,--.

Column 42, Line 20, "Suppl:5141-149" should be --Suppl:S141-149--.

Column 48, Line 42, "79070E-9" should be --79070F-9--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*